United States Patent
Britton et al.

(10) Patent No.: US 7,868,014 B2
(45) Date of Patent: Jan. 11, 2011

(54) 1-(HETERO)ARYL-3-AMINO-PYRROLIDINE DERIVATIVES FOR USE AS MGLUR3 ANTAGONISTS

(75) Inventors: Thomas Charles Britton, Carmel, IN (US); Veronique Dehlinger, Basingstoke (GB); Colin Peter Dell, Basingstoke (GB); Bruce Anthony Dressman, Indianapolis, IN (US); Jason Kenneth Myers, Indianapolis, IN (US); Eric Samuel Nisenbaum, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 917 days.

(21) Appl. No.: 11/576,960

(22) PCT Filed: Oct. 13, 2005

(86) PCT No.: PCT/US2005/036665

§ 371 (c)(1),
(2), (4) Date: Apr. 10, 2007

(87) PCT Pub. No.: WO2006/044454

PCT Pub. Date: Apr. 27, 2006

(65) Prior Publication Data

US 2008/0300266 A1 Dec. 4, 2008

Related U.S. Application Data

(60) Provisional application No. 60/619,789, filed on Oct. 18, 2004.

(51) Int. Cl.
C07D 401/04 (2006.01)
C07D 409/04 (2006.01)
A61K 31/506 (2006.01)

(52) U.S. Cl. .................. 514/275; 514/342; 514/343; 514/370; 514/422; 514/426; 544/330; 546/271.1; 546/279.1; 548/198; 548/527; 548/557

(58) Field of Classification Search .................. 544/330; 546/271.1, 279.1; 548/198, 527, 557; 514/275, 514/342, 343, 370, 422, 426
See application file for complete search history.

(56) References Cited

U.S. PATENT DOCUMENTS

| 4,785,119 A | 11/1988 | Hojo et al. |
| 5,232,929 A | 8/1993 | Desai et al. |
| 5,292,738 A | 3/1994 | Stokbroekx et al. |
| 5,332,817 A | 7/1994 | Desai et al. |
| 5,604,252 A | 2/1997 | O'Neill |
| 5,891,889 A | 4/1999 | Anthony et al. |
| 5,972,947 A | 10/1999 | Tsaklakidis et al. |
| 2001/0006972 A1 | 7/2001 | Williams |
| 2001/0018429 A1 | 8/2001 | Kozlkowski et al. |
| 2005/0032800 A1 | 2/2005 | Bigot et al. |

FOREIGN PATENT DOCUMENTS

| WO | WO 9109844 | 7/1991 |
| WO | WO 9301170 | 1/1993 |
| WO | WO97/28128 | 8/1997 |
| WO | WO99/64396 | 12/1999 |
| WO | WO9964396 | 12/1999 |
| WO | WO02091988 | 11/2002 |
| WO | WO2004072025 | 8/2004 |
| WO | WO2004110995 | 12/2004 |
| WO | WO2005/042542 | 5/2005 |
| WO | WO2005/115975 | 12/2005 |

OTHER PUBLICATIONS

Peroutka S J: "Dopamine and migraine", *Neurology*, vol. 49, No. 3, pp. 650-656, Sep. 1997.

*Primary Examiner*—Deepak Rao
(74) *Attorney, Agent, or Firm*—Mark A. Winter; David M. Stemerick

(57) ABSTRACT

The present invention relates to compounds of the Formula (I) which are useful for treating conditions associated with mGluR3 receptors, such as depression, schizophrenia and migraine, pharmaceutical compositions thereof, and methods of using the same.

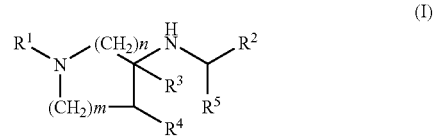

(I)

15 Claims, No Drawings

1-(HETERO)ARYL-3-AMINO-PYRROLIDINE DERIVATIVES FOR USE AS MGLUR3 ANTAGONISTS

This is a 371 of International Application No. PCT/US2005/036665 filed Oct. 13, 2005 which claims priority to U.S. Provisional Application No. 60/619,789 filed Oct. 18, 2004.

L-Glutamate is the major excitatory neurotransmitter in the central nervous system and is referred to as an excitatory amino acid. Glutamate receptors are composed of two major subtypes: the ligand-gated ion-channel ionotropic receptors, and the G protein-coupled seven-transmembrane-domain metabotropic receptors (mGluRs). The metabotropic family is sub-divided into three groups based on sequence similarity, signal transduction, and pharmacology. Group I consists of $mGluR_1$, and $mGluR_5$ (and their splice variants) and mediate stimulation of phospholipase C and the generation of an intracellular calcium signal. Group II, consisting of $mGluR_2$ and $mGluR_3$, and Group III, consisting of $mGluR_4$, $mGluR_6$, $mGluR_7$, and $mGluR_8$, regulate cyclic AMP levels by indirectly inhibiting adenylyl cyclase activity.

The mGlu receptor subtypes have unique expression patterns in the central nervous system, which can be targeted with new and selective agents. The compounds of the present invention are antagonists of mGlu receptors, particularly $mGluR_3$ receptors. As such they are useful for the treatment of conditions associated with metabotropic glutamate receptors.

The present invention provides compounds of formula I, which include aminopyrrolidines and aminopiperidines. Certain aminopyrrolidines and aminopiperidines, useful as substance P antagonists, are described in WO 91/09844, WO 93/01170, and U.S. Pat. No. 5,232,929.

Certain aminopyrrolidines which interact with dopamine receptor subtypes are described in WO 99/64396. Certain aminopyrrolidine intermediates are disclosed in WO 02/091988 and WO 04/110995.

BRIEF SUMMARY OF THE INVENTION

The present invention provides compounds of formula I:

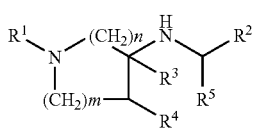

(I)

wherein $R^1$ is selected from the group consisting of phenyl, optionally substituted with from 1 to 3 substituents independently selected from the group consisting of hydroxy, alkyl, substituted alkyl, alkenyl, alkynyl, alkoxy, cycloalkoxy, cycloalkyl, trifluoromethoxy, halogen, cyano, and nitro; and heteroaryl selected from the group consisting of thienyl, pyridyl, pyrimidyl, thiazolyl, quinolyl, and isoquinolyl, each heteroaryl optionally substituted with from 1 to 2 substituents independently selected from the group consisting of alkyl, alkenyl, alkynyl, alkanonyl, alkoxy, phenyl, trifluoromethyl, halogen, cyano, and nitro;

$R^2$ is selected from the group consisting of phenyl, optionally substituted with from 1 to 3 substituents independently selected from the group consisting of alkyl, substituted alkyl, alkoxy, cycloalkyl, methylenedioxy, halogen, cyano, and nitro; naphthyl, optionally substituted with from 1 to 2 substituents independently selected from the group consisting of hydroxy, alkyl, substituted alkyl, alkynyl, alkoxy, phenyl, halogen, cyano, and nitro; and heteroaryl selected from the group consisting of pyridyl, furyl, thienyl, isothiazolyl, and benzothienyl, each heteroaryl optionally substituted with from 1 to 2 substituents independently selected from the group consisting of alkyl, alkoxy, trifluoromethyl, halogen, cyano, and nitro;

$R^3$ is selected from the group consisting of hydrogen and methyl;

$R^4$ is selected from the group consisting of hydrogen, methyl, hydroxy, oxo, and fluoro;

$R^5$ is selected from the group consisting of hydrogen and methyl;

n is 1 or 2; and m is 1 or 2;

and the pharmaceutically acceptable salts thereof;

excluding the compounds (S)-benzyl-[1-(5-trifluoromethylpyrid-2-yl)-pyrrolidin-3-yl]-amine, 4-chlorobenzyl-[1-quinol-2-yl-pyrrolidin-3-yl]-amine, 4-bromobenzyl-[1-quinol-2-yl-pyrrolidin-3-yl]-amine, and 4-methylbenzyl-[1-quinol-2-yl-pyrrolidin-3-yl]-amine.

The present invention also provides pharmaceutical compositions, comprising: a compound of the formula I and a pharmaceutically acceptable excipient.

Because the compounds of formula I are antagonists of $mGluR_3$ receptors, the compounds of formula I are useful for the treatment of a variety conditions associated with metabotropic glutamate receptors, such as neurological and mental disorders. The present invention also provides methods of treating conditions associated with metabotropic glutamate receptors comprising administering to a patient in need thereof an effective amount of a compound of formula I.

It is understood that the present invention provides compounds of formula I for use as a medicament. Further, the present invention provides compounds of formula I for use in the manufacture of a medicament for the treatment of conditions associated with metabotropic glutamate receptors, including each condition specifically mentioned herein.

DETAILED DESCRIPTION OF THE INVENTION

As used herein, the following terms have the meanings indicated:

The term "alkyl" refers to a straight or branched alkyl chain having from one to six carbon atoms, and includes methyl, ethyl, propyl, isopropyl, butyl, iso-butyl, sec-butyl, t-butyl, pentyl, hexyl, and the like.

The term "substituted alkyl" refers to a straight or branched alkyl chain having from one to six carbon atoms, and includes methyl, ethyl, propyl, isopropyl, butyl, iso-butyl, sec-butyl, t-butyl, pentyl, hexyl, and the like having from 1 to 3 substituents selected from the group consisting of hydroxy, halogen, alkoxy, carboxy, alkoxycarbonyl, amido, and phenyl. Specifically included within the scope of this term is trifluoromethyl.

The term "alkenyl" refers to a straight or branched alkenyl chain having from two to six carbon atoms and one or more carbon-carbon double bonds, and includes ethylene, propylene, iso-propylene, butylene, iso-butylene, sec-butylene, pentylene, hexylene, and the like.

The term "alkynyl" refers to a straight or branched alkynyl chain having from two to four carbon atoms and one or more carbon-carbon triple bonds, and includes ethynyl, propynyl, and the like.

The term "alkanonyl" refers to a straight or branched alkyl chain having from one to four carbon atoms and an oxo group, and includes ethanonyl, i.e., —C(O)—CH$_3$.

The term "alkoxy" refers to a straight or branched alkyl chain having from one to four carbon atoms attached to an oxygen atom, and includes methoxy, ethoxy, n-propoxy, iso-propoxy, n-butoxy, iso-butoxy, sec-butoxy, and t-butoxy.

The term "halogen" refers to a chloro, fluoro, bromo or iodo atom.

The term "cycloalkyl" refers to a cyclic alkyl chain having from three to seven carbon atoms, and includes cyclopropyl, cyclobutyl, cyclopentyl, cyclohexyl, and the like.

The term "cycloalkoxy" refers to a cyclic alkyl chain having from three to seven carbon atoms attached to an oxygen atom, and includes cyclopropyloxy, cyclobutyloxy, cyclopentyloxy, cyclohexyloxy, and the like.

The term "oxo" refers to a doubly bonded oxygen, for example, where $R^4$ is oxo $R^4$ together with the carbon atom to which it is attached form a carbonyl (C=O).

The term "pharmaceutically acceptable salt" as used herein, refers to salts of pharmaceutically acceptable organic acids or inorganic acids. Such salts include those known to the skilled artisan, such as those described in Journal of Pharmaceutical Science, 66, 2-19 (1977). Examples of such pharmaceutically acceptable salts are the hydrochloride, fumarate, and mesylate salts.

The skilled artisan will appreciate that certain of the compounds of the present invention exist as stereoisomers. All mixtures of stereoisomers, in any ratio, and specific stereoisomers of the compounds of formula I are contemplated to be within the scope of the present invention. Typically, the Cahn-Ingold-Prelog designations of (R)- and (S)- are used herein to refer to specific stereoisomers. Where a chiral compound is resolved into its isomers, but absolute configurations or optical rotations are not determined, the isomers may be arbitrarily designated, such as isomer 1, isomer 2, etc.

The specific stereoisomers of compounds of formula I can be prepared by a variety of methods known to the skilled person, such as resolution of racemic mixtures and stereoselective synthesis or by using enantiomerically pure starting materials. The specific stereoisomers of either starting materials or compounds of formula I can be obtained by techniques well known in the art, such as those found in Asymmetric Synthesis, edited by James P. Morrison (Academic Press 1983), Stereochemistry of Organic Compounds, E. I. Eliel and S. H. Wilen (Wiley 1994) and Enantiomers, Racemates, and Resolutions, J. Jacques, A. Collet, and S. H. Wilen (Wiley 1991), and those found in PCT Publication Nos. WO 97/25983, published 24 Jul. 1997; and WO 99/04778, published 4 Feb. 1999, including chromatography on chiral stationary phases, enzymatic resolutions, or resolution of diastereomers formed for that purpose, such as fractional crystallization of diastereomeric salts.

As with any group of pharmaceutically active compounds, in the compounds of formula I some groups are preferred in their end use application. As is readily understood, in the preferred embodiments, unless otherwise indicated, the mention of phenyl or particular heteroaryls includes optionally substitution as described in formula I. For example, the mention of pyrimidyl includes optionally substitution with from 1 to 2 substituents independently selected from the group consisting of alkyl, alkenyl, alkynyl, alkanonyl, alkoxy, phenyl, trifluoromethyl, halogen, cyano, and nitro.

Compounds wherein $R^4$ is selected from the group consisting of hydrogen, methyl, hydroxy, and fluoro are preferred.

Compounds wherein $R^4$ is other than quinol-2-yl are preferred.

Compounds wherein $R^4$ is selected from the group consisting of hydrogen, methyl, hydroxy, and fluoro and $R^1$ is other than quinol-2-yl are more preferred.

Compounds wherein $R^3$ is hydrogen are preferred.
Compounds wherein $R^4$ is hydrogen are preferred.
Compounds wherein $R^5$ is hydrogen are preferred.
Compounds wherein $R^3$ is hydrogen, $R^4$ is hydrogen, and $R^5$ is hydrogen are even more preferred.
Compounds wherein n is 1 and m is 1 are preferred.
Compounds wherein $R^3$ is hydrogen, $R^4$ is hydrogen, $R^5$ is hydrogen, n is 1, and m is 1 are even more preferred.

Compounds wherein $R^1$ is heteroaryl selected from the group consisting of thienyl, pyridyl, pyrimidyl, and thiazolyl are preferred.

Compounds wherein $R^1$ is pyrimidyl are more preferred.
Where $R^1$ is pyrimidyl attachment at the 2-position is preferred.

Compounds wherein $R^2$ is phenyl are preferred.
Where $R^2$ is phenyl substitution with 1 to 3 substituents independently selected from the group consisting of alkyl, alkoxy, trifluoromethyl, halogen, cyano, and nitro are even more preferred.

Where $R^2$ is phenyl substitution with 1 to 2 substituents independently selected from the group consisting of trifluoromethyl and halogen are even more preferred.

Compounds wherein $R^3$ is hydrogen, $R^4$ is hydrogen, $R^5$ is hydrogen, n is 1, and m is 1, $R^1$ is pyrimidyl, and $R^2$ is phenyl are preferred. Such compounds wherein the $R^1$ pyrimidyl is substituted with from 1 to 2 substituents independently selected from the group consisting of alkynyl, trifluoromethyl, halogen, cyano, and nitro, and the $R^2$ phenyl is optionally substituted with from 1 to 3 substituents independently selected from the group consisting of alkyl, substituted alkyl, alkoxy, cycloalkyl, halogen, cyano, and nitro are more preferred. Such compounds wherein the $R^1$ pyrimidyl is substituted with from 1 to 2 substituents independently selected from the group consisting of alkynyl, trifluoromethyl, and halogen, and the $R^2$ phenyl is optionally substituted with from 1 to 2 substituents independently selected from the group consisting of trifluoromethyl and halogen are more preferred.

Compounds wherein $R^1$ is pyridyl are preferred.
Where $R^1$ is pyridyl substituted with from 1 to 2 substituents independently selected from the group consisting of alkynyl, trifluoromethyl, halogen, cyano, and nitro are preferred.

Where $R^1$ is pyridyl attachment in the 2- or 3-positions are preferred.

Compounds wherein $R^3$ is hydrogen, $R^4$ is hydrogen, $R^5$ is hydrogen, n is 1, m is 1 $R^1$ is pyridyl, and $R^2$ is phenyl are preferred.

Compounds wherein $R^3$ is hydrogen, $R^4$ is hydrogen, $R^5$ is hydrogen, n is 1, m is 1 $R^1$ is pyrid-2-yl or pyrid-3-yl, and $R^2$ is phenyl are preferred.

Where $R^1$ is pyrid-2-yl or pyrid-3-yl optional substitution with 1 to 2 substituents independently selected from the group consisting of alkynyl, trifluoromethyl, halogen, cyano, and nitro are more preferred.

Compounds when $R^2$ is 4-chlorophenyl, 4-bromophenyl, or 4-methylphenyl then $R^1$ is other than quinolin-2-yl are preferred. Stated more broadly, when $R^2$ is 4-halophenyl or 4-alkylphenyl then $R^1$ is other than quinolin-2-yl. Also, when $R^2$ is phenyl optionally having one substituent, then $R^1$ is other than quinolin-2-yl optionally having one substituent. Stated more broadly, when $R^2$ is phenyl then $R^1$ is other than quinolyl. Stated even more broadly, when $R^2$ is phenyl then $R^1$ is other than quinolyl or isoquinolyl.

Compounds having the stereochemical configuration shown below are preferred:

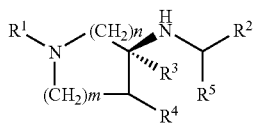

For the compounds described herein, such compounds having the stereochemical configuration shown above are more preferred.

Illustrative compounds of the invention include: 1-(5-chloropyrimidin-2-yl)-pyrrolidin-3-yl]-(2,4-dichlorobenzyl)-amine, and 1-(5-bromopyrimidin-2-yl)-pyrrolidin-3-yl]-(2,4-dichlorobenzyl)-amine. Further illustrative compounds of the invention include: benzyl-[1-(5-trifluoromethylpyrid-2-yl)-pyrrolidin-3-yl]-amine, benzyl-[1-(3-trifluoromethylphenyl)-pyrrolidin-3-yl]-amine, 2-chlorobenzyl-1-phenyl-pyrrolidin-3-yl-amine, and 4-chlorobenzyl-1-phenyl-pyrrolidin-3-yl-amine.

The compounds of formula I can be prepared by a variety of procedures, some of which are described below. In Scheme A all substituents, unless otherwise indicated, are as previously defined, and all reagents are well known and appreciated in the art. The products of each step in Scheme A can be recovered by conventional methods including extraction, evaporation, precipitation, chromatography, filtration, trituration, crystallization, and the like.

Scheme A

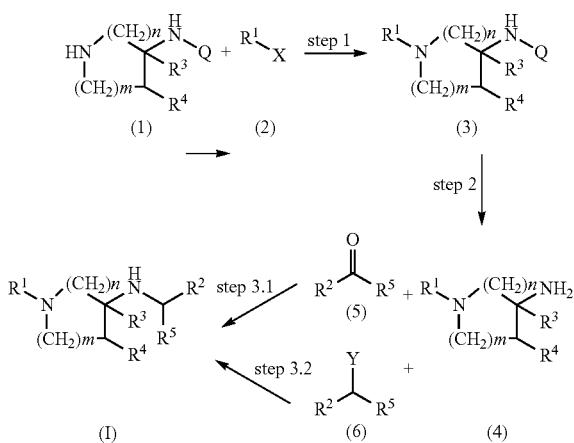

In Scheme A, step 1, depicts the reaction of an appropriate compound of formula (1) with an appropriate compound of formula (2) to give a compound of formula (3). In this step 1 an appropriate compound of formula (1) is one in which n, m, $R^3$ are defined for formula I, $R^4$ is hydrogen, fluoro, and hydroxy, and Q is an amine protecting group. The selection and use of suitable protecting groups is well known and appreciated in the art (see for example, *Protecting Groups in Organic Synthesis*, Theodora Greene (Wiley-Interscience)). While the compound of formula (1) is drawn for convenience to depict the protected amine as —NHQ it is understood that with some suitable protecting groups, for example phthalamide, there may not be a hydrogen attached to the amine nitrogen. While the products of each step in Scheme A can be resolved to give a particular stereochemistry, it is convenient to introduce a desired configuration in step 1 by the use of resolved compounds of formula (1). Therefore, an appropriate compound of formula (1) may be one having a particular stereochemistry. Particular isomers of the compounds of formula (1) can be obtained by methods well known in the art and by methods described herein to give enantiomerically pure compounds. Further processing of resolved compounds of formula (1), via steps described infra, results in enantiomerically pure compounds of formula I. As used herein the term "enantiomerically pure" refers to greater than 80%, preferably greater than 90%, more preferably greater than 95%, most preferably greater than 97% of a particular isomer. Appropriate compounds of formula (1) are readily obtained by the skilled person using methods known in the art and methods described herein and by analogy thereto. An appropriate compound of formula (2) is one in which $R^1$ is as defined for formula I or gives rise to $R^1$ as desired in formula I and X is a suitable leaving group, such as a halide, particularly bromo and iodo, triflate, boronic acid, and the like. Appropriate compounds of formula (2) are well known in the art.

For example, a compound of formula (1) is reacted with a compound of formula (2) in a suitable solvent, such as dimethyl sulfoxide, dimethylformamide, acetonitrile, toluene, dioxane, ethylene glycol, isopropanol, and the like and with the use of a base, such as cesium carbonate, sodium t-butoxide, potassium phosphate, potassium carbonate, sodium carbonate, diisopropyethylamine, and the like. Such reactions generally are carried out at temperature of from about 50° C. to the reflux temperature of the chosen solvent and use from about 1 to 6 equivalents of the compound of formula (2) and typically require 1 to 72 hours to be complete. Such reactions can also be carried out in the presence of a catalyst, such as palladium or copper catalysts. While a variety of catalysts can by used, typical catalysts include palladium acetate, palladium tetrakistriphenylphosphine, ((tris(dibenzylidineacetone)palladium (0) and rac-2,2'-bis(diphenylphospino)-1,1'-binaphthyl (BINAP) or tri-tert-butylphosphine. When a catalyst is used, typically from about 1 to 1.5 equivalents of the compound of formula (2) are used.

Alternately, in Scheme A, step 1, an appropriate compound of formula (1) can be an unprotected compound of formula (1), that is, a compound as depicted in formula (1) in which n, m, and $R^3$ are defined for formula I, and $R^4$ is hydrogen, fluoro, and hydroxy, and Q represents hydrogen. When such a compound of formula (1) is reacted with an appropriate compound of formula (2) the reaction gives a compound of formula (4) directly.

For example, a compound of formula (1) in which Q represents hydrogen is reacted with a compound of formula (2) in a suitable solvent, such as dimethyl sulfoxide, dimethylformamide, ethanol, isopropanol, water, and the like. A base, such as sodium carbonate, sodium bicarbonate, diisopropyethylamine, and the like can be used. Such reactions generally are carried out at temperature of from about 50° C. to the reflux temperature of the chosen solvent and use from about 1 to 6 equivalents of the compound of formula (2) and typically require 1 to 24 hours to be complete.

In Scheme A, step 2, a compound of formula (3) is deprotected to give a compound of formula (4). The removal of suitable protecting groups is well known and appreciated in the art (see for example, *Protecting Groups in Organic Synthesis*, Theodora Greene (Wiley-Interscience)).

In Scheme A, step 3.1, depicts the reductive amination of a compound of formula (4) with an appropriate compound of formulas (5) to give a compound or formula I. An appropriate compound of formula (5) is one in which R² and R⁵ are as desired in the final compound of formula I.

For example, reductive aminations are carried out under a variety of conditions using reducing agents, such as sodium borohydride, sodium triacetoxyborohydride, zinc/hydrochloric acid, zinc borohydride, and the like. A particularly useful reagent for such reactions is sodium cyanoborohydride. When using sodium cyanoborohydride the reaction is carried out in a solvent, such as methanol, ethanol, isopropanol, and water or mixtures thereof. As is well known in the art, it may be advantageous to monitor and adjust the pH during such reactions. Typically the reaction is carried out at temperatures of from about 0° C. to about 60° C. and typically require from about 1 to about 24 hours.

Alternately, such reactions can be carried out by hydrogenation over a catalyst. A variety of catalysts are suitable for this purpose, including palladium, platinum, and nickel catalysts. Such hydrogenations are carried out in a suitable solvent such as ethyl acetate, ethanol, methanol, isopropanol, and the like and are carried out at pressure ranging from atmospheric to about 300 psi (2068 kPascals) and temperatures of from room temperature to about 100° C.

In Scheme A, step 3.2, depicts the alkylation of a compound of formula (4) with an appropriate compound of formula (6) to give a compound or formula I. An appropriate compound of formula (6) is one in which R² and R⁵ are as desired in the final compound of formula I and Y is a leaving group, such as a halogen, particularly chlorine, bromine or iodine, or a sulfonate, such as methanesulfonate or p-toluenesulfonate For example, a compound of formula (4) is reacted with a compound of formula (6) in a suitable solvent, such as ethyl acetate, tetrahydrofuran, dimethylformamide, or acetonitrile and a base, such as potassium carbonate, sodium carbonate, sodium bicarbonate, triethylamine, or diisopropyethylamine. Such reactions generally are carried out at a temperature of from room temperature to the reflux temperature of the chosen solvent and typically use from about 1 to 3 equivalents of the compound of formula (6). Such reactions typically require 1 to 24 hours to be complete.

It will be recognized by one of skill in the art that the steps in Scheme A may be varied to provide compounds of formula I. In particular, the order of the steps required to produce the compounds of formula I is dependent upon the particular compound being synthesized, the starting compound, and the relative lability of the substituted moieties. For example, it is readily understood that compounds of formula I are prepared from an appropriate compound of formula (7), shown below

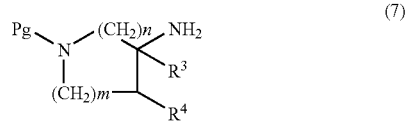

(7)

by carrying out the procedures of steps 3.2 or 3.1, 2, and 1. It is also readily understood that an appropriate compound of formula (7) is one in which n, m, R³, are defined for formula I, and R⁴ hydrogen, fluoro, or hydroxy, and Pg is an amine protecting group and such a compound may be one having a particular stereochemistry.

In addition, it will be readily understood that compounds of formula I (or an intermediate thereof) can be further elaborated to give rise to a compound of formula I. For example, a compound of formula I in which R¹ is substituted with halogen, such as iodo and bromo, can give rise to compounds of formula I in which R¹ is substituted with alkenyl, alkynyl, cyano, and the like or a compound in which R⁴ is hydroxy can be oxidized to give a compound in which R⁴ is oxo. Such reactions are well known in the art. Also, Scheme A can give rise to protected compounds, such as protected hydroxy or protected alkynyl compounds of formula I, which are deprotected in an optional step to give a compound of formula I. Also in Scheme A, in an optional step, an acid addition salt of a compound of formula I is formed using a pharmaceutically-acceptable acid. The formation of acid addition salts is well known and appreciated in the art.

The present invention is further illustrated by the following examples and preparations. These examples and preparations are illustrative only and are not intended to limit the invention in any way.

The terms used in the examples and preparations have their normal meanings unless otherwise designated. For example, "mL" refers milliliter or milliliters; "mp" refers to melting point; "brine" refers to a saturated aqueous sodium chloride solution; etc.

Preparation 1

(S)-(2,4-Dichlorobenzyl)-pyrrolidin-3-ylamine

Stir a mixture of (S)-3-amino-pyrrolidine-1-carboxylic acid tert-butyl ester (15.07 g, 81.0 mmol) and 2,4-dichlorobenzaldehyde (13.46 g, 76.9 mmol) in dry methanol (250 mL) at room temperature under nitrogen overnight. Add slowly sodium borohydride (4.74 g, 125.4 mmol) and stir for 10 min. Concentrate and add 2 N NaOH (150 mL) and extract with diethyl ether. Combine the organic layers, wash with saturated aqueous sodium chloride, dry (magnesium sulfate) and concentrate to give (S)-3-(2,4-dichlorobenzylamino)-pyrrolidine-1-carboxylic acid tert-butyl ester which may be used without further purification (26.9 g, 100%).

Alternatively, add sodium triacetoxyborohydride (1.6 g, 7.6 mmol) to a mixture of (S)-3-aminopyrrolidine-1-carboxylic acid tert-butyl ester (1 g, 5.4 mmol) and 2,4-dichlorobenzaldehyde (2.8 g, 16.2 mmol) in 1,2-dichloroethane (10 mL) and stir overnight at room temperature. Dilute with dichloromethane and wash with saturated aqueous sodium chloride, dry (magnesium sulfate) concentrate and chromatograph on silica gel to give (S)-3-(2,4-dichlorobenzylamino)-pyrrolidine-1-carboxylic acid tert-butyl ester (865 mg, 33%). ¹H NMR (400 MHz, CDCl₃) δ7.33-7.38 (2H, m), 7.23 (1H, d, J=7.82 Hz), 3.85 (2H, d, J=1.96 Hz), 3.45-3.56 (2H, m), 3.30-3.40 (2H, m), 3.19-3.10 (1H, m), 2.04 (1H, m), 1.74 (1H, m), 1.46 (9H, s), MS (ES): m/z=345 [M+].

Stir (S)-3-(2,4-dichlorobenzylamino)-pyrrolidine-1-carboxylic acid tert-butyl ester (1.08 g, 3.13 mmol) in 20% trifluoroacetic acid in dichloromethane (10 mL) overnight. Concentrate and dissolve the residue in methanol (2 mL) and deposit onto an SCX-cartridge; eluting with methanol, then with 2 N ammonia in methanol. Concentrate the ammonia washing to give the title compound (630 mg, 82%).

¹H NMR (400 MHz, CDCl₃) δ 7.32-7.37 (2H, m), 7.22 (1H, dd, J=8.07, 2.20 Hz), 3.81 (2H, s), 3.25-3.31 (1H, m), 3.07-3.13 (1H, m), 2.96 (1H, m), 2.89 (1H, m), 2.81 (1H, m), 2.05-2.15 (2H, m), 1.94-2.04 (1H, m), 1.52-1.60 (1H, m), MS (ES): m/z=245 [M+].

The following compounds are prepared essentially as described in Preparation 1: (S)-(2-Chloro-4-fluorobenzyl)-pyrrolidin-3-ylamine, ¹H NMR (400 MHz, CDCl₃) δ 7.65 (1H, dd, J=8.67, 5.84 Hz), 7.33 (1H, dd, J=8.57, 2.54 Hz), 7.14 (1H, td, J=8.29, 2.64 Hz), 3.85 (2H, s), 3.25-3.31 (1H, m), 3.07-3.13 (1H, m), 2.96 (1H, m), 2.89 (1H, m), 2.81 (1H, m), 2.05-2.15 (2H, m), 1.94-2.07 (1H, m), 1.52-1.63 (1H, m), MS (ES): m/z=229 [M+H].

(S)-(4-Fluoro-2-trifluoromethylbenzyl)-pyrrolidin-3-ylamine, $^1$H NMR (300 MHz, CDCl$_3$) δ 7.62 (1H, dd, J=8.37, 5.54 Hz), 7.36 (1H, dd, J=9.02, 2.60 Hz), 7.20-7.26 (1H, m), 3.80 (2H, s), 3.25-3.31 (1H, m), 3.05-3.11 (1H, m), 2.96 (1H, m), 2.89 (1H, m), 2.81 (1H, m), 2.05-2.15 (2H, m), 1.94-2.02 (1H, m), 1.52-1.60 (1H, m), MS (ES): m/z=263 [M+H].

Preparation 2

5-Chloro-2-trifluoromethylbenzaldehyde

Add borane-THF complex (3.34 mL, 3.34 mmol) slowly to an ice-methanol cooled bath solution of 5-chloro-2-trifluoromethyl-benzoic acid (500 mg, 2.23 mmol) in THF (2 mL). Stir overnight at room temperature. Add water (1 mL) and solid potassium carbonate. Filter and concentrate to give an oil residue. Chromatograph on silica gel, eluting with 10:90 to 1:1 ethyl acetate:hexanes to give (5-chloro-2-trifluoromethylphenyl)-methanol as a white solid (347 mg, 75%). $^1$H NMR (400 MHz, MeOH-d4) δ 7.84 (s, 1H), 7.68 (d, 1H, J=8.4 Hz), 7.48 (d, 1H, J=8.4 Hz), 4.81 (s, 2H).

Dissolve (5-chloro-2-trifluoromethylphenyl)-methanol (347 mg, 1.66 mmol) in dichloromethane (10 mL). Add pyridinium chlorochromate (717 mg, 3.32 mmol) and stir for 2 h. Dilute with diethyl ether and stir for 1 h. Filter and concentrate. Chromatograph on silica gel eluting with 10% ethyl acetate in hexane to give the title compound as a clear oil (285 mg, 82%). $^1$H NMR (400 MHz, MeOH-d4) δ 10.33 (s, 1H), 7.90 (s, 1H), 7.69 (d, 1H, J=8.4 Hz), 7.54 (d, 1H, J=8.4 Hz).

Preparation 3

Trans-4-(2,4-Dichlorobenzylamino)-pyrrolidin-3-ol

Stir a mixture of 2,5-dihydropyrrole-1-carboxylic acid tert-butyl ester (2 g, 11.8 mmol), 3-chloroperoxybenzoic acid (77%, 3.1 g, 14.2 mmol) and 3-tert-butyl-4-hydroxy-5-methylsulfide (254 mg, 0.7 mmol) in 1,2-dichloroethane (50 mL) at 85° C. for 4 h under nitrogen. Add extra 3-chloroperoxybenzoic acid (77%, 1.16 g, 4.7 mmol) and stir at 85° C. for 5 h. Allow to cool to room temperature and add dichloromethane (120 mL), wash with 5% aqueous sodium bisulfate, then with saturated aqueous sodium hydrogen carbonate and finally with saturated aqueous sodium chloride, dry (magnesium sulfate), concentrate and chromatograph on silica gel, eluting with 0:100 to 40:60 ethyl acetate:cyclohexane to give 6-oxa-3-azabicyclo[3.1.0]hexane-3-carboxylic acid tert-butyl ester (1.55 g, 71%). $^1$H NMR (400 MHz, CDCl$_3$) δ 3.82 (1H, d, J=13.20 Hz), 3.74 (1H, d, J=12.72 Hz), 3.67 (2H, d, J=3.42 Hz), 3.31 (2H, dd, J=13.45, 5.14 Hz), 1.44 (9H, s).

Stir a mixture of 6-oxa-3-azabicyclo[3.1.0]hexane-3-carboxylic acid tert-butyl ester (800 mg, 4.3 mmol) and 2,4-dichlorobenzylamine (2.8 mL, 21.6 mmol) in ethanol (5 mL) at 80° C. for 48 h. Concentrate and dissolve in dichloromethane, add polymer supported 4-benzaldehyde (20 g) and stir for 48 h. Filter, concentrate and chromatograph on silica gel, eluting with 0:100 to 60:40 ethyl acetate:cyclohexane to give trans-3-(2,4-dichlorobenzylamino)-4-hydroxypyrrolidine-1-carboxylic acid tert-butyl (900 mg, 58%). $^1$H NMR (300 MHz, CDCl$_3$) δ 7.38 (1H, d, J=2.07 Hz), 7.26 (1H, s), 7.21-7.25 (1H, m), 4.08-4.16 (1H, m), 3.83-3.90 (2H, m), 3.66 (2H, s), 3.20-3.34 (1H, m), 3.07-3.19 (2H, m), 1.45 (9H, s), MS (ES): m/z 361 [M+].

3-(2,4-Dichlorobenzylamino)-4-hydroxypyrrolidine-1-carboxylic acid tert-butyl ester is treated essentially as described in Preparation 1 to give the title compound. $^1$H NMR (300 MHz, CDCl$_3$) δ 7.37 (1H, d, J=2.07 Hz), 7.29-7.34 (1H, m), 7.19-7.24 (1H, m), 4.01-4.08 (1H, m), 3.84 (2H, s), 3.25 (1H, dd, J=11.49, 6.03 Hz), 3.16 (1H, dd, J=12.06, 4.90 Hz), 3.06 (1H, m), 2.79-2.89 (2H, m), 2.65 (1H, dd, J=11.59, 3.86 Hz), MS (ES): m/z=261 [M+].

Preparation 4

(2,4-Dichlorobenzyl)-(4-fluoropyrrolidin-3-yl)-amine

Stir a mixture of 6-oxa-3-aza-bicyclo[3.1.0]hexane-3-carboxylic acid tert-butyl ester (100 mg, 0.54 mmol) and triethylamine trihydrofluoride (88 µL, 0.54 mmol) at 100° C. for 30 min in a microwave (CEM Discover, 300W). Add saturated aqueous sodium hydrogen carbonate and extract with chloroform. Combine the organic layers and wash with saturated aqueous sodium chloride, dry (magnesium sulfate) and concentrate to give trans-3-fluoro-4-hydroxypyrrolidine-1-carboxylic acid tert-butyl ester which may be used without further purification. $^1$H NMR (300 MHz, CDCl$_3$) δ 4.85 (1H, d, J=50.86 Hz), 4.29 (1H, dd, J=8.01, 2.92 Hz), 3.38-3.65 (4H, m), 1.39 (9H, s).

Cool down a suspension of Dess Martin periodinane (279 mg, 0.65 mmol) in dry dichloromethane (1 mL) under nitrogen with an ice bath and add a solution of trans-3-fluoro-4-hydroxypyrrolidine-1-carboxylic acid tert-butyl ester (90 mg, 0.44 mmol) in dry dichloromethane (1 mL). Stir under nitrogen and allow to warm up to room temperature overnight. Add saturated aqueous sodium hydrogen carbonate, then saturated aqueous sodium thiosulfate and extract with dichloromethane. Combine the organic layers, wash with saturated aqueous sodium chloride, dry (magnesium sulfate) and concentrate to give 3-fluoro-4-oxopyrrolidine-1-carboxylic acid tert-butyl ester which may be used without further purification. Characteristic peaks in the NMR include the proton alpha to the fluorine atom (5.01, 1H, ddd, J=51.52, 7.54, 7.25 Hz).

Add sodium triacetoxyborohydride (156 mg, 0.73 mmol) to a mixture of 3-fluoro-4-oxopyrrolidine-1-carboxylic acid tert-butyl ester (100 mg, 0.5 mmol) and 2,4-dichlorobenzylamine (65 µL, 0.5 mmol) in 1,2-dichloroethane (1.5 mL), followed by 2 drops of glacial acetic acid and stir overnight at room temperature. Pour the crude mixture into 2 N sodium hydroxide and extract with ethyl acetate, wash with water, dry (magnesium sulfate), concentrate and chromatograph on silica gel to give 3-(2,4-dichlorobenzylamino)-4-fluoropyrrolidine-1-carboxylic acid tert-butyl ester (40 mg, 20%). $^1$H NMR (300 MHz, CDCl$_3$) δ 7.36-7.44 (2H, m), 7.20-7.28 (1H, m), 5.03 (1H, d, J=54.07 Hz), 3.21-3.95 (6H, m), 2.99-3.15 (1H, m), 1.45 (9H, s), MS (ES): m/z=363 [M+].

3-(2,4-Dichlorobenzylamino)-4-fluoropyrrolidine-1-carboxylic acid tert-butyl ester is treated essentially as described in Preparation 1 to give the title compound.

$^1$H NMR (300 MHz, CDCl$_3$) δ 7.42 (1H, d, J=8.29 Hz), 7.38 (1H, d, J=2.07 Hz), 7.23 (1H, dd, J=8.19, 2.17 Hz), 4.99 (1H, dt, J=56.33 Hz), 3.85-4.00 (2H, m), 3.14-3.29 (4H, m), 2.67-2.82 (1H, m), MS (ES): m/z=263 [M+].

Preparation 5

(2,4-Dichlorobenzyl)-(4-methylpyrrolidin-3-yl)-amine

Cool down a suspension of copper (I) iodide (1 g, 5.5 mmol) in dry diethyl ether (13 mL) under nitrogen to −10° C.

with a saturated aqueous sodium chloride/ice bath and add methyllithium (1.6 M in diethyl ether, 6.8 mL, 10.9 mmol) dropwise to maintain the temperature at −10° C. Stir for 20 min at this temperature and add a solution of 6-oxa-3-azabicyclo[3.1.0]hexane-3-carboxylic acid tert-butyl ester (430 mg, 2.32 mmol) in dry diethyl ether (5 mL). Stir for 1 h at −10° C. then add water (5 mL) dropwise and dichloromethane (5 mL), filter the resulting mixture through a pad of Celite® and wash thoroughly with dichloromethane. Separate the aqueous and organic phases and extract with 30:70 isopropanol:chloroform and wash with saturated aqueous sodium chloride, dry (magnesium sulfate) and concentrate to give trans-3-hydroxy-4-methylpyrrolidine-1-carboxylic acid tert-butyl ester which can be used without further purification (360 mg, 77%). $^1$H NMR (300 MHz, CDCl$_3$) δ 3.84-3.91 (1H, m), 3.48-3.62 (2H, m), 3.10-3.23 (1H, m), 2.88-3.02 (1H, m), 1.98-2.12 (1H, m), 1.39 (9H, s), 0.95 (3H, d, J=6.97 Hz), MS (ES): m/z=224 [M+Na].

Cool down a suspension of Dess Martin periodinane (1.1 g, 2.6 mmol) in dry dichloromethane (5 mL) under nitrogen with an ice bath and add a solution of trans-3-hydroxy-4-methylpyrrolidine-1-carboxylic acid tert-butyl ester (350 mg, 1.73 mmol) in dry dichloromethane (2 mL). Stir under nitrogen and allow to warm up to room temperature overnight. Add saturated aqueous sodium hydrogen carbonate, then saturated aqueous sodium thiosulfate and extract with dichloromethane. Combine the organic layers and wash with saturated aqueous sodium chloride, dry (magnesium sulfate), concentrate and chromatograph on silica gel, eluting with 0:100 to 40:60 ethyl acetate:2-methylpentane to give 3-methyl-4-oxopyrrolidine-1-carboxylic acid tert-butyl ester (240 mg, 70%). $^1$H NMR (300 MHz, CDCl$_3$) δ 4.06-4.19 (1H, m), 3.84-3.98 (1H, m), 3.61-3.72 (1H, m), 3.17 (1H, dd, J=11.11, 9.04 Hz), 2.56-2.70 (1H, m, J=7.72 Hz), 1.49 (9H, s), 1.18 (3H, d, J=7.16 Hz), MS (ES): m/z=222 [M+Na].

3-Methyl-4-oxopyrrolidine-1-carboxylic acid tert-butyl ester is treated essentially as described in Preparation 4 to give 3-(2,4-dichlorobenzylamino)-4-methylpyrrolidine-1-carboxylic acid tert-butyl ester. $^1$H NMR (300 MHz, CDCl$_3$) δ 7.32-7.41 (2H, m), 7.17-7.25 (1H, m), 3.77-3.91 (2H, m), 3.22-3.50 (5H, m), 2.17-2.47 (1H, m), 1.45 (9H, s), 1.01 (3H, d, J=6.97 Hz), MS (ES): m/z=359 [M+].

3-(2,4-Dichlorobenzylamino)-4-methylpyrrolidine-1-carboxylic acid tert-butyl ester is treated essentially as described in Preparation 1 to give the title compound. MS (ES): m/z=259 [M+].

Preparation 6

(2,4-Dichlorobenzyl)-(3-methylppyrrolidin-3-yl)-amine

Add 1-benzyl-3-pyrrolidinone (10 g, 61.7 mmol) in dry THF (40 mL) to methyl magnesium bromide (3 M in diethyl ether, 44 mL, 132 mmol) at −20° C. Stir for 3 h and allow the reaction to warm up to 0° C. Pour onto crushed ice and extract with diethyl ether. Combine the organic layers and wash with saturated aqueous sodium chloride, dry (magnesium sulfate) and concentrate to give 1-benzyl-3-methylpyrrolidin-3-ol which may be used directly in the next step without further purification (8.6 g, 73%). $^1$H NMR (400 MHz, CDCl$_3$) δ 7.22-7.33 (5H, m), 3.63 (2H, s), 2.92-2.99 (1H, m), 2.71 (1H, d, J=9.29 Hz), 2.28-2.36 (1H, m), 2.22 (1H, d, J=9.78 Hz), 1.84-1.91 (2H, m), 1.33 (3H, s), MS (ES): m/z=192 [M+H].

Add concentrated sulphuric acid (16 mL) dropwise to 1-benzyl-3-methyl-pyrrolidin-3-ol (4.4 g, 23 mmol) in acetonitrile (12 mL) at 0° C. Stir and allow the resulting solution to warm up gradually to room temperature overnight. Pour onto crushed ice and add saturated aqueous potassium carbonate and extract with dichloromethane. Combine the organic layers and wash with saturated aqueous sodium chloride, dry (magnesium sulfate) and concentrate to give N-(1-benzyl-3-methylpyrrolidin-3-yl)-acetamide which may be used in the next step without further purification (4.89 g, 70%). $^1$H NMR (400 MHz, CDCl$_3$) δ 7.22-7.34 (5H, m), 5.62 (1H, s), 3.57-3.66 (2H, m), 2.76-2.84 (2H, m), 2.54 (1H, td, J=8.80, 5.87 Hz), 2.47 (1H, d, J=9.78 Hz), 2.13 (1H, m), 1.90-1.93 (3H, m), 1.84-1.90 (1H, m), 1.49 (3H, s), MS (ES): m/z=233 [M+H].

Add titanium (IV) isopropoxide (2.8 mL, 9.46 mmol) dropwise to a stirred mixture of N-(1-benzyl-3-methylpyrrolidin-3-yl)-acetamide (2 g, 8.6 mmol) and diphenylsilane (10 mL). Stir overnight at room temperature under nitrogen. Pour into saturated aqueous sodium hydrogen carbonate and extract with chloroform. Combine the organic layers and wash with saturated aqueous sodium chloride, dry (magnesium sulfate) and concentrate. Add methanol and filter off the white precipitate. Add bulk Isolute sorbent SCX-2 silica (20 g) and stir for 2 h. Filter off the silica, wash with methanol and with 2 N ammonia in methanol. Concentrate to give 1-benzyl-3-methylpyrrolidin-3-ylamine which may be used in the next step without further purification (1.31 g, 86%). $^1$H NMR (300 MHz, CDCl$_3$) δ 7.22-7.35 (5H, m), 3.59 (2H, d, J=2.26 Hz), 2.83 (1H, td, J=8.67, 5.27 Hz), 2.37-2.51 (2H, m), 2.30 (1H, d, J=9.04 Hz), 1.76-1.86 (1H, m), 1.66-1.74 (3H, m), 1.24 (3H, s), MS (ES): m/z=191 [M+H].

1-Benzyl-3-methylpyrrolidin-3-ylamine is treated essentially as described in Preparation 1 to give (1-benzyl-3-methylpyrrolidin-3-yl)-(2,4-dichlorobenzyl)-amine. $^1$H NMR (300 MHz, CDCl$_3$) δ 7.31 (1H, d, J=8.29 Hz), 7.12-7.26 (6H, m) 7.08-7.12 (1H, m), 3.66 (2H, d, J=4.90 Hz), 3.50 (2H, d, J=6.97 Hz), 2.71 (1H, dt, J=8.67, 4.33 Hz), 2.64 (1H, d, J=9.42 Hz), 2.33-2.43 (1H, m), 2.17 (1H, d, J=9.23 Hz), 1.79-1.91 (1H, m), 1.66 (1H, m), 1.21 (3H, s), MS (ES): m/z=349 [M+].

Add 1-chloroethyl chloroformate (232 μL, 2.14 mmol) to (1-benzyl-3-methylpyrrolidin-3-yl)-(2,4-dichlorobenzyl)-amine (250 mg, 0.71 mmol) in dry dichloromethane (2 mL) at 0° C. Allow to warm slowly to room temperature then heat at 45° C. for 48 h. Cool to 0° C. and add extra 1-chloroethyl chloroformate (232 μL, 2.14 mmol) then heat at 45° C. for 48 h. Concentrate, add methanol (2 mL) and heat at 70° C. overnight. Concentrate and dissolve the residue in chloroform, add saturated aqueous sodium hydrogen carbonate and extract with chloroform. Combine the organic layers and wash with saturated aqueous sodium chloride, dry (magnesium sulfate) and concentrate to give the title compound. MS (ES): m/z=259 [M+].

Preparation 7

(S)-(1-(2,4-Dichlorophenyl)-ethyl)-pyrrolidin-3-ylamine

Stir a mixture of (S)-3-aminopyrrolidine-1-carboxylic acid tert-butyl ester (10.4 g, 55.7 mmol) and 2,4-dichloroacetophenone (10.5 g, 55 mmol) in dry toluene (400 mL) at 110° C. for 48 h. Concentrate and dissolve the residue in methanol (160 mL), add sodium borohydride (3.37 g, 89 mmol) slowly and stir for 20 min. Add 1 N sodium hydroxide (200 mL) and extract with diethyl ether. Combine the organic layers, wash with water, dry (magnesium sulfate), concentrate and chromatograph on silica gel, eluting with 0:100 to 40:60 ethyl acetate:2-methylpentane to give (S)-3-[1-(2,4-dichlorophenyl)-ethylamino]-pyrrolidine-1-carboxylic acid tert-butyl ester (5.6 g, 28%). ¹H NMR (300 MHz, CDCl₃) δ 7.41-7.51 (1H, m), 7.34 (1H, s), 7.24 (1H, dd, J=8.38, 1.98 Hz), 4.21-4.36 (1H, m), 3.42-3.57 (2H, m), 3.21-3.33 (1H, m), 3.04-3.15 (1H, m), 2.88-3.03 (1H, m), 1.96-2.05 (1H, m), 1.63-1.72 (1H, m), 1.37-1.47 (9H, m), 1.30 (3H, dd, J=6.59, 1.51 Hz), MS (ES): m/z=359[M+].

(S)-3-[1-(2,4-Dichlorophenyl)-ethylamino]-pyrrolidine-1-carboxylic acid tert-butyl ester is treated essentially as described in Preparation 1 to give the title compound. ¹H NMR (300 MHz, CDCl₃) δ 7.41-7.50 (1H, m), 7.34 (1H, d, J=1.88 Hz), 7.22-7.27 (1H, m), 4.27 (1H, m), 3.00-3.13 (2H, m), 2.78-2.94 (2H, m), 2.19 (2H, s), 1.84-1.99 (1H, m), 1.54-1.65 (1H, m), 1.41-1.52 (1H, m), 1.30 (3H, dd, J=6.59, 1.13 Hz), MS (ES): m/z=259 [M+].

Preparation 8

6-(3-Aminopyrrolidin-1-yl)-nicotinonitrile

Stir a solution of diisopropylethylamine (9.5 mL, 54.3 mmol), 6-chloronicotinonitrile (5 g, 36.2 mmol) and 3-tert-butyloxycarbonylpyrrolidine (10 g, 54.3 mmol) in DMF (10 mL). After 3 days, dilute with dichloromethane and an aqueous saturated solution of sodium bicarbonate and separate the layers. Extract the aqueous layer once with dichloromethane, dry (sodium sulfate), filter and concentrate. Filter through a plug of silica gel, wash with dichloromethane and concentrate to give [1-(5-cyanopyridin-2-yl)-pyrrolidin-3-yl]-carbamic acid tert-butyl ester as a white solid (8.13 g, 78%). ¹H NMR (400 MHz, CDCl₃) δ 8.38 (dd, 1H, J=2.4 Hz, 1.0 Hz), 7.58-7.55 (m, 1H), 6.33 (dd, 1H, J=9.8 Hz, 1.0 Hz), 4.85-4.7 (m, 1H), 4.40-4.25 (m, 1H), 3.85-3.30 (m, 4H), 2.35-2.25 (m, 1H), 2.08-1.90 (m, 1H), 1.43 (s, 9H); MS (ES): m/z=289 [M+H]+.

Add trifluoroacetic acid (30 mL) to [1-(5-cyanopyridin-2-yl)-pyrrolidin-3-yl]-carbamic acid tert-butyl ester (7.95 g, 27.6 mmol) in dichloromethane (200 mL) and stir for 2 h. Concentrate, add toluene (100 mL) and reconcentrate to give a residue. Partition the residue between dichloromethane and an saturated aqueous solution of sodium bicarbonate and separate the layers. Extract the aqueous layer 5 times with 15:85 isopropyl alcohol:chloroform, combine the organic layers, dry (sodium sulfate), filter, and concentrate to give the title compound as a yellow oil (5.25 g). ¹H NMR (400 MHz, CDCl₃) δ 8.34 (d, 1H, J=2.5 Hz), 7.53-7.50 (m, 1H), 6.29 (d, 1H, J=8.8 Hz), 3.80-3.10 (m, 5H), 2.25-2.15 (m, 1H), 1.90-1.75 (m, 3H); MS (ES): m/z=189 [M+H]+.

Example 1

(S)-(2,4-Dichlorobenzyl)-[1-(5-nitropyridin-2-yl)-pyrrolidin-3-yl]-amine

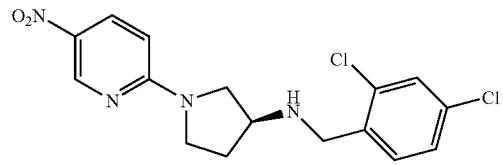

Degas a mixture of (S)-(2,4-dichlorobenzyl)-pyrrolidin-3-ylamine (245 mg, 1 mmol), 2-bromo-5-nitropyridine (168 mg, 0.83 mmol) and cesium carbonate (404 g, 1.24 mmol) in dry toluene (2 mL) by bubbling nitrogen for 15 min. Add tris(dibenzylideneacetone)dipalladium (0) (15 mg, 0.016 mmol) and (S)-(−)-2,2'-bis(diphenylphosphino)-1,1'-binaphthyl (18 mg, 0.024 mmol). Stir the resulting mixture at 90° C. overnight. Chromatograph on silica gel and concentrate to give the title compound (280 mg, 92%).

Dissolve (S)-(2,4-dichlorobenzyl)-[1-(5-nitropyridin-2-yl)-pyrrolidin-3-yl]-amine (280 mg, 0.76 mmol) in ethanol (1 mL), add trimethylsilylchloride (95 μl, 0.76 mmol.), and add diethyl ether (1 mL) and triturate. Concentrate and dry in a vacuum oven overnight to give the title compound as its hydrochloride salt. ¹H NMR (300 MHz, MeOH-d4) δ 8.91 (1H, d, J=2.64 Hz), 8.29 (1H, dd, J=9.51, 2.73 Hz), 7.58-7.62 (2H, m), 7.40 (1H, dd, J=8.29, 2.07 Hz), 6.68 (1H, d, J=9.42 Hz), 4.41 (2H, s), 4.03-4.18 (2H, m), 3.87 (2H, m), 3.60-3.69 (1H, m), 2.55-2.66 (1H, m), 2.36 (1H, m), MS (ES): m/z=367 [M+].

The following compounds are prepared essentially as described in Example 1. In the tables below the bond on the various groups indicates the point of attachment.

| EX | Compound | R¹ | R² |
|----|----------|----|----|
| 2 | (S)-4-[3-(2,4-Dichlorobenzylamino)-pyrrolidin-1-yl]-benzonitrile hydrochloride ¹H NMR (300 MHz, MeOH-d4) δ 7.52-7.63 (2H, m), 7.44 (2H, d, J=8.85 Hz), 7.37-7.42 (1H, m), 6.64 (2H, d, J=8.85 Hz), 4.39 (2H, s), 4.06-4.18 (1H, m), 3.75 (1H, dd, J=11.30, 6.97 Hz), 3.51-3.64 (2H, m), 3.33-3.45 (1H, m), 2.48-2.61 (1H, m), 2.28 (1H, td, J=13.89, 6.50 Hz), MS (ES): m/z = 346 [M+]. | 4-CN-phenyl | 2,4-diCl-phenyl |

-continued

| EX | Compound | R¹ | R² |
|---|---|---|---|
| 3 | (S)-[1-(4-Chlorophenyl)-pyrrolidin-3-yl]-(2,4-dichlorobenzyl)-amine hydrochloride<br>¹H NMR (300 MHz, MeOH-d4) δ 7.52-7.59 (2H, m), 7.40 (1H, dd, J=8.29, 2.07 Hz), 7.07-7.12 (2H, m), 6.53-6.58 (2H, m), 4.37 (2H, s), 4.06 (1H, m), 3.47-3.60 (3H, m), 3.22-3.28 (1H, m), 2.45-2.57 (1H, m), 2.16-2.28 (1H, m), MS (ES): m/z = 355 [M+]. | 4-chlorophenyl | 2,4-dichlorophenyl |
| 4 | (S)-(2,4-Dichlorobenzyl)-[1-(4-trifluoromethylphenyl)-pyrrolidin-3-yl]-amine hydrochloride<br>¹H NMR (300 MHz, MeOH-d4) δ 7.53-7.59 (2H, m), 7.40 (3H, dt, J=8.48, 2.26 Hz), 6.66 (2H, d, J=8.67 Hz), 4.39 (2H, s), 4.06-4.15 (1H, m), 3.67-3.74 (1H, m), 3.53-3.62 (2H, m), 3.31-3.40 (1H, m), 2.48-2.60 (1H, m), 2.20-2.32 (1H, m), MS (ES): m/z = 389 [M+]. | 4-trifluoromethylphenyl | 2,4-dichlorophenyl |
| 5 | (S)-4-[3-(2,4-Dichlorobenzylamino)-pyrrolidin-1-yl]-2-fluorobenzonitrile hydrochloride<br>¹H NMR (300 MHz, MeOH-d4) δ 7.53-7.59 (2H, m), 7.38-7.44 (2H, m), 6.45-6.49 (1H, m), 6.43 (1H, dd, J=8.76, 1.98 Hz), 4.38 (2H, s), 4.06-4.15 (1H, m), 3.76 (1H, m,), 3.51-3.61 (2H, m), 3.40 (1H, m), 2.48-2.60 (1H, m), 2.20-2.32 (1H, m), MS (ES): m/z = 364 [M+]. | 3-fluoro-4-cyanophenyl | 2,4-dichlorophenyl |
| 6 | (S)-1-{5-[3-(2,4-Dichlorobenzylamino)-pyrrolidin-1-yl]-thiophen-2-yl}-ethanone<br>¹H NMR (300 MHz, CDCl₃) δ 7.44 (1H, d, J=4.33 Hz), 7.33-7.43 (2H, m), 7.18-7.26 (1H, m), 5.74 (1H, d, J=4.33 Hz), 3.89 (2H, s), 3.48-3.61 (3H, m), 3.38 (1H, m), 3.16-3.26 (1H, m), 2.40 (3H, s), 2.18-2.32 (1H, m), 1.98 (1H, m), MS (ES): m/z = 369 [M+]. | 5-methyl-2-acetylthiophene | 2,4-dichlorophenyl |
| 7 | (S)-2-Chloro-4-[3-(2,4-dichlorobenzylamino)-pyrrolidin-1-yl]-benzonitrile<br>¹H NMR (300 MHz, CDCl₃) δ 7.36-7.43 (2H, m), 7.33 (1H, s), 7.21-7.25 (1H, m), 6.53 (1H, d, J=2.26 Hz), 6.39 (1H, dd, J=8.76, 2.35 Hz), 3.90 (2H, s), 3.48-3.57 (3H, m), 3.32-3.41 (1H, m), 3.13-3.22 (1H, m), 2.17-2.31 (1H, m), 1.91-2.03 (1H, m), MS (ES): m/z = 380 [M+]. | 2-chloro-4-cyanophenyl | 2,4-dichlorophenyl |
| 8 | (S)-4-[3-(2,4-Dichlorobenzylamino)-pyrrolidin-1-yl]-3-methyl-benzonitrile hydrochloride<br>¹H NMR (300 MHz, MeOH-d4) δ 7.57 (1H, s), 7.56 (1H, d, J=5.09 Hz), 7.39 (2H, dd, J=8.48, 2.07 Hz), 7.35 (1H, s), 6.88 (1H, d, J=9.04 Hz), 4.36 (2H, s), 3.97-4.06 (1H, m), 3.47-3.56 (3H, m), 3.22-3.29 (1H, m), 2.42-2.54 (1H, m), 2.29 (3H, s), 2.08-2.19 (1H, m), MS (ES): m/z = 360 [M+]. | 3-methyl-4-cyanophenyl | 2,4-dichlorophenyl |
| 9 | (S)-3-[3-(2,4-Dichlorobenzylamino)-pyrrolidin-1-yl]-benzonitrile hydrochloride<br>¹H NMR (300 MHz, MeOH-d4) δ 7.68-7.66 (2H, m), 7.51 (1H, dd, J=8.29, 2.07 Hz), 7.35-7.45 (1H, m), 6.94-7.07 (3H, m), 4.46 (2H, s), 4.17 (1H, m), 3.68-3.80 (1H, m), 3.62 (2H, m), 3.37-3.46 (1H, m), 2.62 (1H, m), 2.35 (1H, m), MS (ES): m/z = 346 [M+]. | 3-cyanophenyl | 2,4-dichlorophenyl |

-continued

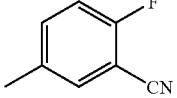

| EX Compound | R¹ | R² |
|---|---|---|
| 10 (S)-5-[3-(2,4-Dichlorobenzylamino)-pyrrolidin-1-yl]-2-fluorobenzonitrile hydrochloride<br>¹H NMR (300 MHz, MeOH-d4) δ 7.51-7.62 (2H, m), 7.39 (1H, dd, J=8.19, 2.17 Hz), 7.12 (1H, t, J=9.04 Hz), 6.89 (1H, dt, J=9.14, 3.72 Hz), 6.82 (1H, dd, J=4.90, 3.20 Hz), 4.37 (2H, s), 4.03-4.13 (1H, m), 3.58-3.65 (1H, m), 3.52 (2H, m), 3.23-3.31 (1H, m), 2.46-2.58 (1H, m), 2.25 (1H, m), MS (ES): m/z = 364 [M+]. | 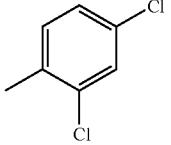 | 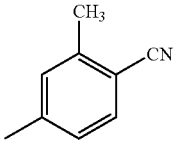 |
| 11 (S)-4-[3-(2,4-Dichlorobenzylamino)-pyrrolidin-1-yl]-2-methylbenzonitrile hydrochloride<br>¹H NMR (300 MHz, MeOH-d4) δ 7.64 (1H, d, J=8.29 Hz), 7.54 (1H, d, J=2.26 Hz), 7.38 (1H, dd, J=8.29, 2.07 Hz), 7.33 (1H, d, J=8.67 Hz), 6.49-6.53 (1H, m), 6.43-6.49 (1H, m), 4.40 (2H, s), 4.07-4.17 (1H, m), 3.69-3.80 (1H, m), 3.52-3.63 (2H, m), 3.31-3.42 (1H, m), 2.48-2.61 (1H, m), 2.25-2.40 (4H, m), MS (ES): m/z = 360 [M+]. | 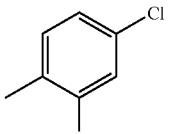 | 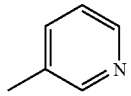 |
| 12 (S)-2,4-Dichlorobenzyl-(1-pyridin-3-yl-pyrrolidin-3-yl)-amine<br>¹H NMR (300 MHz, MeOH-d4) δ 7.87 (1H, s), 7.81 (1H, d, J=4.33 Hz), 7.51 (2H, dd, J=5.18, 3.11 Hz), 7.34 (1H, dd, J=8.29, 2.07 Hz), 7.26 (1H, dd, J=8.38, 4.80 Hz), 7.11 (1H, dd, J=8.38, 1.98 Hz), 4.21 (2H, s), 3.85-3.94 (1H, m), 3.48-3.64 (2H, m), 3.38-3.46 (1H, m), 3.25-3.36 (1H, m), 2.37-2.49 (1H, m), 2.15 (1H, m), MS (ES): m/z = 322 [M+]. | 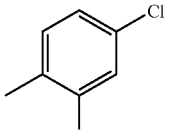 | 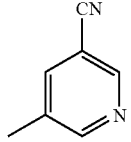 |
| 13 (S)-5-[3-(2,4-Dichlorobenzylamino)-pyrrolidin-1-yl]-nicotinonitrile<br>¹H NMR (300 MHz, CDCl₃) δ 8.07-8.16 (2H, m, J=11.68, 2.26 Hz), 7.30-7.41 (2H, m), 7.23 (1H, dd, J=8.29, 2.07 Hz), 6.93 (1H, dd, J=2.83, 1.70 Hz), 3.91 (2H, s), 3.45-3.59 (3H, m), 3.28-3.42 (1H, m), 3.10-3.21 (1H, m), 2.18-2.31 (1H, m), 1.91-2.04 (1H, m), MS (ES): m/z = 347 [M+]. | 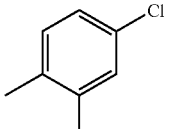 | 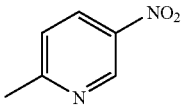 |
| 14 (S)-(2-Chloro-4-fluorobenzyl)-[1-(5-nitropyridin-2-yl)-pyrrolidin-3-yl]-amine hydrochloride<br>¹H NMR (300 MHz, MeOH-d4) δ 8.89 (1H, d, J=2.45 Hz), 8.25 (1H, dd, J=9.42, 2.64 Hz), 7.65 (1H, dd, J=8.67, 5.84 Hz), 7.33 (1H, dd, J=8.57, 2.54 Hz), 7.14 (1H, td, J=8.29, 2.64 Hz), 6.64 (1H, d, J=9.42 Hz), 4.40 (2H, d, J=2.64 Hz), 4.01-4.17 (1H, m), 3.74-3.90 (2H, m), 3.57-3.70 (1H, m), 2.53-2.65 (1H, m), 2.34 (1H, m), MS (ES): m/z = 351 [MH]. | 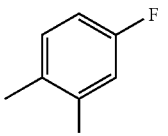 | 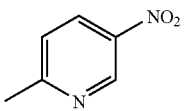 |
| 15 (S)-(4-Fluoro-2-trifluoromethylbenzyl)-[1-(5-nitropyridin-2-yl)-pyrrolidin-3-yl]-amine hydrochloride<br>¹H NMR (300 MHz, MeOH-d4) δ 8.91 (1H, d, J=2.64 Hz), 8.21 (1H, dd, J=9.32, 2.73 Hz), 7.80 (1H, dd, J=8.57, 5.18 Hz), 7.57 (1H, dd, J=8.85, 2.64 Hz), 7.47 (1H, td, J=8.24, 2.73 Hz), 6.55 (1H, d, J=9.42 Hz), 4.41 (2H, s), 4.15 (1H, m), 4.04 (1H, m), 3.71-3.87 (2H, m), 3.55-3.69 (1H, m), 2.52-2.67 (1H, m), 2.24-2.39 (1H, m), MS (ES): m/z = 385 [M + H]. | 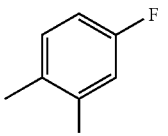 | 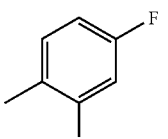 |

-continued

| EX | Compound | R¹ | R² |
|---|---|---|---|
| 16 | (S)-[1-(5-Bromothiazol-2-yl)-pyrrolidin-3-yl]-(2-chloro-4-fluorobenzyl)-amine hydrochloride<br>¹H NMR (300 MHz, MeOH-d4) δ 7.69 (1H, dd, J=8.67, 5.84 Hz), 7.43 (1H, s), 7.33 (1H, dd, J=8.57, 2.54 Hz), 7.14 (1H, td, J=8.38, 2.64 Hz), 4.39 (2H, d, J=3.01 Hz), 4.19-4.28 (1H, m), 3.95-4.04 (1H, m), 3.74-3.85 (2H, m), 3.62 (1H, m), 2.58-2.70 (1H, m), 2.39-2.51 (1H, m), MS (ES): m/z = 391 [M + H]. | 2-methyl-5-bromothiazol-2-yl | 2-chloro-4-fluorophenyl |
| 17 | (S)-[1-(4-Bromothiazol-2-yl)-pyrrolidin-3-yl]-(4-fluoro-2-trifluoromethylbenzyl)-amine<br>¹H NMR (300 MHz, CDCl₃) δ 7.64 (1H, dd, J=8.38, 5.56 Hz), 7.35 (1H, dd, J=9.04, 2.64 Hz), 7.18-7.25 (1H, m), 6.34 (1H, s), 3.94 (2H, s), 3.67 (1H, m), 3.52-3.63 (2H, m), 3.46 (1H, m), 3.32 (1H, m), 2.18-2.30 (1H, m), 1.94 (1H, m), MS (ES): 425 = [M + H]. | 2-methyl-4-bromothiazol-2-yl | 4-fluoro-2-trifluoromethylphenyl |
| 18 | (S)-(4-Fluoro-2-trifluoromethylbenzyl)-[1-(5-nitrothiazol-2-yl)-pyrrolidin-3-yl]-amine<br>¹H NMR (300 MHz, CDCl₃) δ 8.17 (1H, s), 7.62 (1H, dd, J=8.38, 5.56 Hz), 7.36 (1H, dd, J=9.04, 2.64 Hz), 7.20-7.26 (1H, m), 3.96 (2H, s), 3.60-3.8 (5H, m), 2.24-2.35 (1H, m), 1.99-2.09 (1H, m), MS (ES): m/z = 391 [M + H]. | 2-methyl-5-nitrothiazol-2-yl | 4-fluoro-2-trifluoromethylphenyl |
| 19 | (S)-[1-(5-Bromothiazol-2-yl)-pyrrolidin-3-yl]-(4-fluoro-2-trifluoromethylbenzyl)-amine hydrochloride<br>¹H NMR (300 MHz, MeOH-d4) δ 7.82 (1H, dd, J=8.57, 5.18 Hz), 7.58 (1H, dd, J=8.85, 2.64 Hz), 7.48 (1H, td, J=8.19, 2.45 Hz), 7.15 (1H, s), 4.40 (2H, s), 4.18 (1H, ddd, J=11.68, 6.59, 6.40 Hz), 3.89 (1H, dd, J=11.59, 6.88 Hz), 3.59-3.69 (2H, m), 3.44-3.54 (1H, m), 2.53-2.65 (1H, m), 2.32 (1H, m), MS (ES): m/z = 425 [M + H]. | 2-methyl-5-bromothiazol-2-yl | 4-fluoro-2-trifluoromethylphenyl |
| 20 | (S)-(2,4-Dichlorobenzyl)-[1-(5-nitrothiazol-2-yl)-pyrrolidin-3-yl]-amine hydrochloride<br>¹H NMR (300 MHz, MeOH-d4) δ 8.15 (1H, s), 7.52-7.62 (2H, m), 7.41 (1H, dd, J=8.38, 2.17 Hz), 4.40 (2H, d, J=2.07 Hz), 4.11-4.22 (1H, m), 3.97-4.05 (1H, m), 3.66-3.82 (2H, m), 3.54-3.63 (1H, m), 2.56-2.68 (1H, m), 2.36 (1H, m), MS (ES): m/z = 373 [M+]. | 2-methyl-5-nitrothiazol-2-yl | 2,4-dichlorophenyl |
| 21 | (S)-(2-Chloro-4-fluorobenzyl)-[1-(5-nitrothiazol-2-yl)-pyrrolidin-3-yl]-amine hydrochloride<br>¹H NMR (300 MHz, MeOH-d4) δ 8.15 (1H, s), 7.64 (1H, dd, J=8.67, 5.84 Hz), 7.35 (1H, dd, J=8.67, 2.64 Hz), 7.16 (1H, td, J=8.38, 2.64 Hz), 4.40 (2H, d, J=1.88 Hz), 4.11-4.23 (1H, m), 3.97-4.06 (1H, m), 3.79 (1H, m), 3.56-3.72 (2H, m), 2.61 (1H, m), 2.31-2.44 (1H, m), MS (ES): m/z = 357 [M + H]. | 2-methyl-5-nitrothiazol-2-yl | 2-chloro-4-fluorophenyl |
| 22 | (S)-(2,4-Dichlorobenzyl)-[1-(3-nitropyridin-2-yl)-pyrrolidin-3-yl]-amine hydrochloride<br>¹H NMR (300 MHz, MeOH-d4) δ 8.28 (1H, dd, J=4.71, 1.70 Hz), 8.09 (1H, dd, J=8.01, 1.60 Hz), 7.52-7.59 (2H, m), 7.38 (1H, dd, J=8.29, 2.07 Hz), 6.78 (1H, dd, J=8.10, 4.52 Hz), 4.36 (2H, d, J=5.84 Hz), 3.99-4.09 (1H, m), 3.63-3.77 (2H, m), 3.45-3.59 (2H, m), 2.49 (1H, m), 2.12-2.25 (1H, m), MS (ES): m/z = 367 [M+]. | 3-nitropyridin-2-yl | 2,4-dichlorophenyl |

-continued

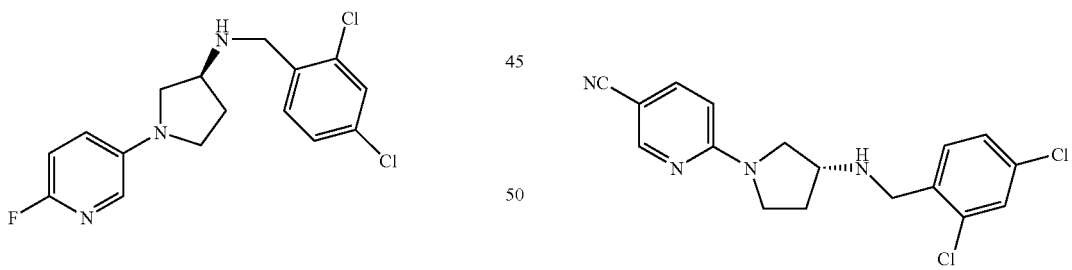

| EX | Compound | R¹ | R² |
|---|---|---|---|
| 23 | (S)-(2,4-Dichlorobenzyl)-[1-(5-iodopyridin-2-yl)-pyrrolidin-3-yl]-amine hydrochloride<br>¹H NMR (300 MHz, MeOH-d4) δ 8.13 (1H, d, J= 1.70 Hz), 7.85 (1H, dd, J=9.04, 2.07 Hz), 7.51-7.65 (2H, m), 7.39 (1H, dd, J=8.38, 1.98 Hz), 6.59 (1H, d, J=9.23 Hz), 4.32-4.46 (2H, m), 4.06-4.18 (1H, m), 3.83-3.97 (1H, m), 3.64-3.79 (2H, m), 3.45-3.56 (1H, m), 2.50-2.63 (1H, m), 2.35 (1H, m), MS (ES): m/z = 447 [M − H], 449 [M + H]. | 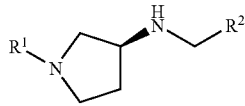 |  |
| 24 | (S)-2,4-Dichlorobenzyl)-[1-(6-fluoro-5-methylpyridin-3-yl)-pyrrolidin-3-yl]-amine hydrochloride<br>¹H NMR (300 MHz, MeOH-d4) δ 7.57 (2H, dd, J=5.18, 3.11 Hz), 7.40 (1H, dd, J=8.29, 2.07 Hz), 7.23-7.26 (1H, m), 7.06 (1H, dd, J=8.29, 2.45 Hz), 4.38 (2H, s), 4.04-4.13 (1H, m), 3.49-3.61 (3H, m), 3.22-3.29 (1H, m), 2.46-2.58 (1H, m), 2.19-2.30 (1H, m), 2.16 (3H, s), MS (ES): m/z = 354 [M+]. |  | 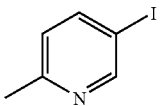 |
| 25 | (S)-(2,4-Dichlorobenzyl)-[1-(2-fluoropyridin-3-yl)-pyrrolidin-3-yl]-amine hydrochloride<br>¹H NMR (300 MHz, CDCl₃) δ 7.92 (1H, d, J= 8.29 Hz), 7.52-7.57 (1H, m), 7.47 (1H, d, J= 1.88 Hz), 7.32 (1H, dd, J=8.29, 1.88 Hz), 6.90-7.04 (2H, m), 4.24 (2H, s), 3.85-3.93 (1H, m), 3.63-3.78 (3H, m), 3.31-3.40 (1H, m), 2.30-2.44 (2H, m), MS (ES): m/z = 340 [M+]. | 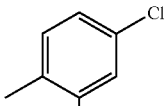 |  |

Example 26

(S)-(2,4-Dichlorobenzyl)-[1-(6-fluoropyridin-3-yl)-pyrrolidin-3-yl]-amine

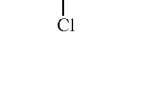

The title compound is prepared essentially as described in Example 1 using 10 mol % of tris(dibenzylideneacetone) dipalladium (0) and 15 mol % of (S)-(−)-2,2'-bis(diphenylphosphino)-1,1'-binaphthyl. The hydrochloride salt of the title compound gives ¹H NMR (300 MHz, MeOH-d4) δ 7.48-7.54 (2H, m), 7.37-7.42 (1H, m), 7.33-7.37 (1H, m), 7.16 (1H, ddd, J=9.09, 6.36, 3.20 Hz), 6.85 (1H, dd, J=8.85, 2.83 Hz), 4.20 (2H, s), 3.84-3.93 (1H, m), 3.44-3.58 (2H, m), 3.35-3.43 (1H, m), 3.23-3.29 (1H, m), 2.42 (1H, m), 2.12 (1H, m), MS (ES): m/z=340 [M+].

Example 27

(R)-6-[3-(2,4-Dichlorobenzylamino)-pyrrolidin-1-yl]-nicotinonitrile

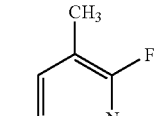

The title compound is prepared essentially as described in Example 1 starting with (R)-3-aminopyrrolidine-1-carboxylic acid tert-butyl ester. The hydrochloride salt of the title compound gives ¹H NMR (300 MHz, CDCl₃) δ 8.40 (1H, d, J=1.88 Hz), 7.58 (1H, dd, J=9.04, 2.26 Hz), 7.33-7.39 (2H, m), 7.20-7.24 (1H, m), 6.33 (1H, d, J=8.85 Hz), 3.90 (2H, s), 3.60-3.75 (2H, m), 3.45-3.57 (2H, m), 3.29-3.45 (1H, m), 2.22 (1H, m), 1.91-2.02 (1H, m), MS (ES): m/z=347 [M+].

Example 28

(S)-[1-(5-Bromopyrimidin-2-yl)-pyrrolidin-3-yl]-(2,4-dichlorobenzyl)-amine

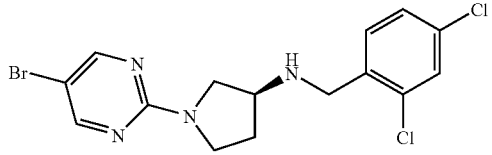

Stir a mixture of (S)-(2,4-dichlorobenzyl)-pyrrolidin-3-ylamine (313 mg, 1.28 mmol), 2-chloro-5-bromopyrimidine (248 mg, 1.28 mmol) and diisopropylethylamine (335 μL, 1.91 mmol) in acetonitrile (2 mL) at 80° C. overnight. Concentrate and chromatograph on SCX-2 column to give the title compound (450 mg, 87%). Form the hydrochloride by essentially the procedure in Example 1 to give $^1$H NMR (400 MHz, MeOH-d4) δ 8.41 (2H, s), 7.62-7.67 (2H, m), 7.49 (1H, dd, J=8.31, 1.96 Hz), 4.46 (2H, d, J=5.62 Hz), 4.16 (1H, m), 3.99-4.05 (1H, m), 3.79-3.86 (2H, m), 3.65 (1H, m), 2.60 (1H, m), 2.28-2.37 (1H, m), MS (ES): m/z=402 [M+].

The following compounds are prepared essentially as described in Example 28.

| EX | Compound | R$^1$ | R$^2$ |
|---|---|---|---|
| 29 | (S)-2-[3-(2,4-Dichlorobenzylamino)-pyrrolidin-1-yl]-thiazole-5-carbonitrile oxalate $^1$H NMR (300 MHz, DMSO-d6) δ 8.05 (1H, s), 7.53-7.65 (2H, m), 7.45 (1H, dd, J=8.38, 2.17 Hz), 4.04 (2H, s), 3.66-3.72 (2H, m), 3.41-3.65 (3H, m), 2.25-2.41 (1H, m), 2.08-2.21 (1H, m), MS (ES): m/z = 353 [M+]. | 2-methyl-thiazole-5-carbonitrile | 2,4-dichlorophenyl |
| 30 | [1-(4-Chloropyridin-2-yl)-pyrrolidin-3-yl]-(2,4-dichlorobenzyl)-amine hydrochloride $^1$H NMR (400 MHz, MeOH-d4) δ 6.74-6.82 (1H, m), 6.52-6.62 (1H, m), 6.44 (1H, s), 6.24-6.33 (1H, m), 6.11-6.19 (1H, m), 5.84-5.92 (1H, m), 3.30 (2H, s), 3.08-3.17 (1H, m), 2.90-3.00 (1H, m), 2.72-2.83 (2H, m), 2.52-2.62 (1H, m), 1.46-1.57 (1H, m), 1.29-1.40 (1H, m), MS (ES): m/z = 356 [M+]. | 4-chloro-pyridin-2-yl | 2,4-dichlorophenyl |
| 31 | (S)-(2,4-Dichlorobenzyl)-(1-pyrimidin-2-yl-pyrrolidin-3-yl)-amine hydrochloride $^1$H NMR (400 MHz, DMSO-d6) δ 8.41 (2H, d, J=4.65 Hz), 7.86 (1H, d, J=8.56 Hz), 7.77 (1H, d, J=2.20 Hz), 7.58 (1H, dd, J=8.44, 2.08 Hz), 6.71 (1H, t, J=4.77 Hz), 4.33 (2H, s), 3.98-4.06 (1H, m), 3.89-3.95 (1H, m), 3.80-3.85 (1H, m), 3.72-3.78 (1H, m), 3.51-3.58 (1H, m), 2.34-2.44 (2H, m), MS (ES): m/z = 323 [M+ | pyrimidin-2-yl | 2,4-dichlorophenyl |
| 32 | (S)-(2,4-Dichloro-benzyl)-[1-(4-methoxypyrimidin-2-yl)-pyrrolidin-3-yl]-amine hydrochloride $^1$H NMR (400 MHz, DMSO-d6) δ 8.16 (1H, d, J=6.36 Hz), 7.92 (1H, d, J=8.31 Hz), 7.76 (1H, d, J=1.96 Hz), 7.57 (1H, dd, J=8.31, 1.96 Hz), 6.34 (1H, s), 4.33 (2H, s), 3.93-4.04 (5H, m), 3.84-3.93 (2H, m), 3.58-3.68 (1H, m), 2.40-2.49 (2H, m), MS (ES): m/z = 353 [M+]. | 4-methoxy-pyrimidin-2-yl | 2,4-dichlorophenyl |
| 33 | (S)-[1-(5-Bromopyrimidin-2-yl)-pyrrolidin-3-yl]-(4-fluoro-2-trifluoromethylbenzyl)-amine hydrochloride (stir the coupling reaction at room temperature) $^1$H NMR (400 MHz, DMSO-d$_6$) δ 8.50 (2H, s), 8.24 (1H, dd, J=8.44, 5.50 Hz), 7.73 (2H, m), 4.32 (2H, s), 3.99-4.08 (1H, m), 3.88-3.95 (1H, m), 3.70-3.82 (2H, m), 3.46-3.54 (1H, m), 2.34-2.45 (2H, m), MS (ES): m/z = 419 [M+]. | 5-bromo-pyrimidin-2-yl | 4-fluoro-2-trifluoromethylphenyl |

Example 34

(S)-6-[3-(2,4-Dichlorobenzylamino)-pyrrolidin-1-yl]-nicotinonitrile

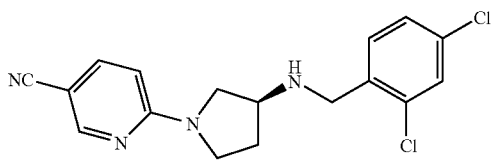

Stir a mixture of (S)-(2,4-dichlorobenzyl)-pyrrolidin-3-ylamine (200 mg, 0.82 mmol), 6-chloronicotinonitrile (75 mg, 0.54 mmol) and diisopropylethylamine (140 µl, 0.82 mmol) in DMF (5 mL) at room temperature overnight. Concentrate and chromatograph on silica gel to give the title compound. Form the hydrochloride by essentially the procedure in Example 1 to give $^1$H NMR (300 MHz, MeOH-d4) δ 8.44 (1H, d, J=1.51 Hz), 7.95 (1H, dd, J=9.23, 2.07 Hz), 7.56-7.68 (2H, m), 7.40 (1H, dd, J=8.38, 2.17 Hz), 6.97 (1H, d, J=9.42 Hz), 4.42 (2H, d, J=3.01 Hz), 4.16-4.25 (1H, m), 4.04-4.13 (1H, m), 3.82-3.96 (2H, m), 3.63-3.77 (1H, m), 2.56-2.69 (1H, m), 2.43 (1H, m), MS (ES): 347 [M+].

The following compounds are prepared essentially as described in Example 34.

Example 37

(S)-[1-(5-Chloropyridin-2-yl)-pyrrolidin-3-yl]-(4-fluoro-2-trifluoromethylbenzyl)-amine

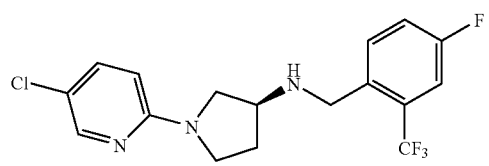

Stir a mixture of (S)-4-fluoro-2-trifluoromethylbenzyl)-pyrrolidin-3-ylamine (200 mg, 0.76 mmol), 2,5-dichloropyridine (80 mg, 0.51 mmol) and diisopropylethylamine (130 µL, 0.76 mmol) at 105° C. for 35 min. in a microwave (CEM Discover, 300W). Concentrate and chromatograph using preparative mass guided chromatography (61 mg, 33%) to give the title compound. Form the hydrochloride by essentially the procedure in Example 1 to give $^1$H NMR (300 MHz, MeOH-d4) δ8.02 (1H, d, J=2.07 Hz), 7.86-7.93 (2H, m), 7.58 (1H, dd, J=8.95, 2.73 Hz), 7.48 (1H, td, J=8.29, 2.64 Hz), 7.01 (1H, d, J=9.42 Hz), 4.43 (2H, s), 4.19-4.27 (1H, m), 3.99-4.06 (1H, m), 3.78-3.86 (2H, m), 3.59-3.68 (1H, m), 2.57-2.69 (1H, m), 2.34-2.46 (1H, m), MS (ES): m/z=374 [M+H].

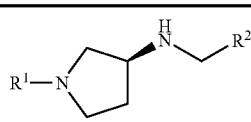

| EX | Compound | R$^1$ | R$^2$ |
|---|---|---|---|
| 35 | (S)-6-[3-(2-Chloro-4-fluorobenzylamino)-pyrrolidin-1-yl]-nicotinonitrile hydrochloride $^1$H NMR (300 MHz, MeOH-d4) δ 8.44 (1H, d, J=1.32 Hz), 7.97 (1H, dd, J=9.42, 2.07 Hz), 7.69 (1H, dd, J=8.67, 5.84 Hz), 7.33 (1H, dd, J=8.57, 2.54 Hz), 7.14 (1H, td, J=8.38, 2.64 Hz), 7.01 (1H, d, J=9.42 Hz), 4.41 (2H, d, J=3.01 Hz), 4.15-4.25 (1H, m), 4.04-4.13 (1H, m), 3.83-3.95 (2H, m), 3.63-3.75 (1H, m), 2.56-2.68 (1H, m), 2.36-2.48 (1H, m), MS (ES): m/z = 331 [M + H]. | 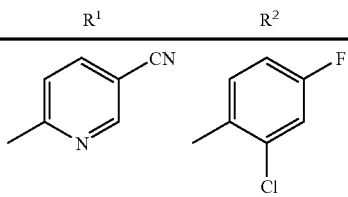 | |
| 36 | (S)-6-[3-(4-Fluoro-2-trifluoromethyl-benzylamino)-pyrrolidin-1-yl]-nicotinonitrile hydrochloride $^1$H NMR (300 MHz, MeOH-d4) δ 8.46 (1H, d, J=1.88 Hz), 7.98 (1H, dd, J=9.32, 1.98 Hz), 7.92 (1H, dd, J=8.67, 5.27 Hz), 7.54-7.60 (1H, m), 7.47 (1H, td, J=8.24, 2.54 Hz), 7.00 (1H, d, J=9.23 Hz), 4.44 (2H, s), 4.17-4.30 (1H, m), 4.05-4.17 (1H, m), 3.84-3.98 (2H, m), 3.64-3.77 (1H, m), 2.57-2.70 (1H, m), 2.36-2.49 (1H, m), MS (ES): m/z = 365 [M + H]. | 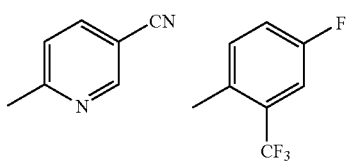 | |

The following compounds are prepared essentially as described in Example 37.

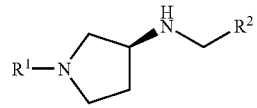

| EX | Compound | R¹ | R² |
|---|---|---|---|
| 38 | (S)-[1-(5-Bromopyridin-2-yl)-pyrrolidin-3-yl]-(4-fluoro-2-trifluoromethylbenzyl)-amine hydrochloride<br>¹H NMR (300 MHz, MeOH-d4) δ 8.04 (2H, td, J= 10.08, 2.07 Hz), 7.92 (1H, dd, J=8.67, 5.09 Hz), 7.58 (1H, dd, J=8.95, 2.73 Hz), 7.48 (1H, td, J=8.29, 2.64 Hz), 7.00 (1H, d, J=9.04 Hz), 4.43 (2H, s), 4.20-4.28 (1H, m), 4.00-4.07 (1H, m), 3.79-3.88 (2H, m), 3.64 (1H, m), 2.58-2.69 (1H, m), 2.41 (1H, m), MS (ES): m/z = 418 [M+]. | 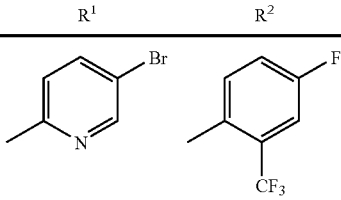 | |
| 39 | (S)-(2-Chloro-4-fluorobenzyl)-[1-(5-trifluoromethylpyridin-2-yl)-pyrrolidin-3-yl]-amine hydrochloride<br>¹H NMR (300 MHz, MeOH-d4) δ 8.27 (1H, s), 8.13 (1H, dd, J=9.51, 2.17 Hz), 7.74 (1H, dd, J= 8.67, 5.84 Hz), 7.32 (1H, dd, J=8.48, 2.64 Hz), 7.23 (1H, d, J=9.61 Hz), 7.14 (1H, td, J=8.38, 2.64 Hz), 4.43 (2H, d, J=3.01 Hz), 4.20-4.33 (1H, m), 4.10-4.20 (1H, m), 3.90-4.04 (2H, m), 3.70-3.82 (1H, m), 2.59-2.72 (1H,m), 2.42-2.55 (1H, m), MS (ES): m/z = 374 [M + H]. | 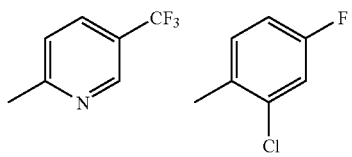 | |
| 40 | (S)-(4-Fluoro-2-trifluoromethylbenzyl)-[1-(5-trifluoromethylpyridin-2-yl)-pyrrolidin-3-yl]-amine hydrochloride<br>¹H NMR (300 MHz, MeOH-d4) δ 8.28 (1H, s), 8.14 (1H, dd, J=9.51, 2.17 Hz), 7.98 (1H, dd, J= 8.57, 5.18 Hz), 7.57 (1H, dd, J=8.85, 2.64 Hz), 7.47 (1H, td, J=8.19, 2.64 Hz), 7.23 (1H, d, J= 9.61 Hz), 4.46 (2H, s), 4.24-4.36 (1H, m), 4.10-4.22 (1H, m), 3.92-4.04 (2H, m), 3.71-3.83 (1H, m), 2.61-2.73 (1 H, m), 2.42-2.55 (1H, m), MS (ES): m/z = 408 [M + H]. | 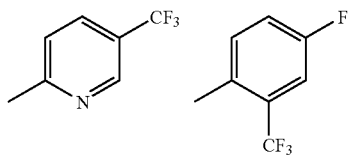 | |
| 41 | (S)-[1-(5-Bromopyridin-2-yl)-pyrrolidin-3-yl]-(2,4-dichlorobenzyl)-amine hydrochloride<br>¹H NMR (300 MHz, MeOH-d4) δ 7.99-8.12 (2H, m), 7.70 (1H, d, J=8.29 Hz), 7.56 (1H, d, J= 2.07 Hz), 7.39 (1H, dd, J=8.38, 2.17 Hz), 7.04-7.15 (1H, m), 4.44 (2H, d, J=3.39 Hz), 4.20-4.31 (1H, m), 4.03-4.13 (1H, m), 3.82-3.97 (2H, m), 3.64-3.75 (1H, m), 2.58-2.71 (1H, m), 2.41-2.56 (1H, m), MS (ES): m/z = 401 [M+]. | 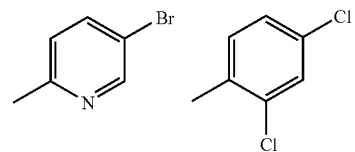 | |
| 42 | (S)-(2-Chloro-4-fluorobenzyl)-[1-(5-chloropyridin-2-yl)-pyrrolidin-3-yl]-amine hydrochloride<br>¹H NMR (300 MHz, MeOH-d4) δ 7.94-8.03 (2H, m), 7.71 (1H, dd, J=8.67, 6.03 Hz), 7.34 (1H, dd, J=8.67, 2.64 Hz), 7.15 (1H, td, J=8.38, 2.64 Hz), 7.09 (1H, d, J=9.61 Hz), 4.42 (2H, d, J= 3.77 Hz), 4.18-4.27 (1H, m), 4.01-4.11 (1H, m), 3.80-3.92 (2H, m), 3.62-3.72 (1H, m), 2.57-2.70 (1H, m), 2.38-2.50 (1H, m), MS (E S): m/z = 340 [M+]. | 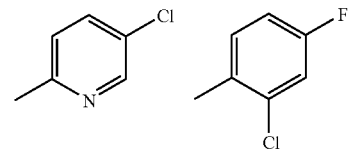 | |
| 43 | (S)-[1-(5-Bromopyridin-2-yl)-pyrrolidin-3-yl]-(2-chloro-4-fluorobenzyl)-amine hydrochloride<br>¹H NMR (300 MHz, MeOH-d4) δ 7.99-8.12 (2H, m), 7.65 (1H, dd, J=8.67, 5.84 Hz), 7.33 (1H, dd, J=8.57, 2.54 Hz), 7.14 (1H, td, J=8.29, 2.64 Hz), 7.04-7.15 (1H, m), 4.42 (2H, d, J=3.77 Hz), 4.18-4.27 (1H, m), 4.01-4.11 (1H, m), 3.80-3.92 (2H, m), 3.62-3.72 (1H, m), 2.57-2.70 (1H, m), 2.38-2.50 (1H, m), MS (ES): m/z = 384 [M+]. | 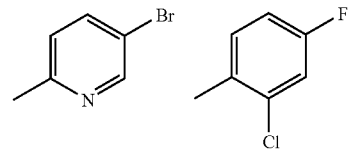 | |

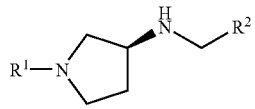

| EX Compound | R¹ | R² |
|---|---|---|
| 44 (S)-(2,4-Dichlorobenzyl)-[1-(5-trifluoromethylpyridin-2-yl)-pyrrolidin-3-yl]-amine hydrochloride<br>¹H NMR (300 MHz, MeOH-d4) δ 8.27 (1H, s), 8.10 (1H, dd, J=9.51, 2.17 Hz), 7.66 (1H, d, J= 8.29 Hz), 7.56 (1H, d, J=2.07 Hz), 7.39 (1H, dd, J=8.29, 2.07 Hz), 7.18 (1H, d, J=9.61 Hz), 4.42 (2H, d, J=3.20 Hz), 4.20-4.29 (1H, m), 4.08-4.16 (1H, m), 3.88-4.00 (2H, m), 3.69-3.78 (1H, m), 2.59-2.71 (1H, m), 240- 252 (1H, m), MS (ES): m/z = 390 [M+]. | 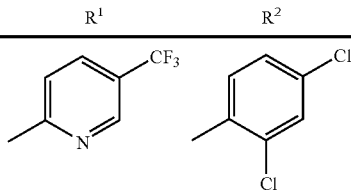 | |
| 45 (S)-[1-(5-Chloropyridin-2-yl)-pyrrolidin-3-yl]-(2,4-dichlorobenzyl)-amine hydrochloride<br>¹H NMR (300 MHz, MeOH-d4) δ 8.00 (1H, d, J= 1.88 Hz), 7.92 (1H, dd, J=9.61, 2.45 Hz), 7.64 (1H, d, J=8.29 Hz), 7.56 (1H, d, J=2.07 Hz), 7.39 (1H, dd, J=8.29, 2.07 Hz), 7.05 (1H, d, J= 9.80 Hz), 4.41 (2H, d, J=3.58 Hz), 4.17-4.25 (1H, m), 3.98-4.11 (1H, m), 3.78-3.90 (2H, m), 3.59-3.74 (1H, m), 2.56-2.68 (1H , m), 2.36-2.49 (1H, m), MS (ES): m/z = 356 [M+]. | 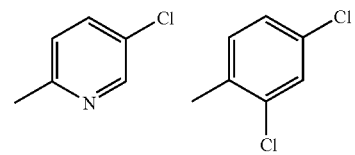 | |
| 46 (S)-(2,4-Dichlorobenzyl)-[1-(4-nitropyridin-2-yl)-pyrrolidin-3-yl]-amine hydrochloride<br>¹H NMR (300 MHz, CDCl₃) δ 8.34 (1H, d, J= 5.46 Hz), 7.32-7.41 (2H, m), 7.22 (1H, dd, J= 8.29, 2.07 Hz), 7.18 (1H, dd, J=5.65, 1.88 Hz), 7.02 (1H, d, J=1.88 Hz), 3.92 (2H, s), 3.63-3.78 (2H, m), 3.48-3.59 (2H, m), 3.42 (1H, m), 2.18-2.31 (1H, m), 1.98 (1H, m), MS (ES): m/z = 367 [M+]. | 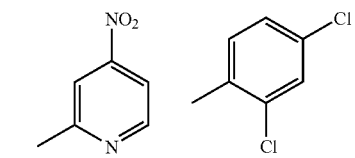 | |
| 47 (S)-[1-(2-Chloropyridin-4-yl)-pyrrolidin-3-yl]-(2,4-dichlorobenzyl)-amine hydrochloride<br>¹H NMR (300 MHz, MeOH-d4) δ 7.90 (1H, d, J= 6.40 Hz), 7.55-7.65 (2H, m), 7.40 (1H, dd, J= 8.29, 2.07 Hz), 6.70 (1H, d, J=2.26 Hz), 6.62 (1H, dd, J=6.40, 2.45 Hz), 4.39 (2H, s), 4.09-4.19 (1H, m), 3.86 (1H, m), 3.58-3.72 (2H, m), 3.43-3.55 (1H, m), 2.50-2.62 (1H, m), 2.26-2.39 (1H, m), MS (ES): m/z = 356 [M+]. | 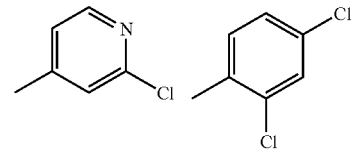 | |

Example 48

[1-(6-Chloropyridin-3-yl)-pyrrolidin-3-yl]-(2,4-dichlorobenzyl)-amine

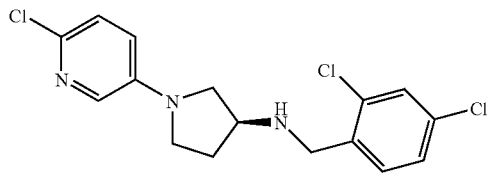

Add 2-chloro-5-iodopyridine (193 mg, 0.84 mmol) to a mixture of potassium carbonate (344 mg, 1.61 mmol) and copper iodide (7 mg, 5% mol) and purge with nitrogen for 10 min. Add a solution of (S)-(2,4-dichlorobenzyl)-pyrrolidin-3-ylamine (238 mg, 0.97 mmol) in ethylene glycol (0.09 mL, 1.61 mmol) and isopropanol (1 mL). Stir at 80° C. for 4 days. Add water (2 mL) and extract with ethyl acetate, wash with saturated aqueous sodium chloride, dry (magnesium sulfate), concentrate and chromatograph using preparative mass guided chromatography to give the title compound. Form the hydrochloride by essentially the procedure in Example 1 to give ¹H NMR (400 MHz, MeOH-d4) δ 7.79 (1H, d, J=2.69 Hz), 7.63-7.70 (2H, m), 7.49 (1H, dd, J=8.31, 1.96 Hz), 7.34 (1H, d, J=8.80 Hz), 7.21 (1H, dd, J=8.80, 2.93 Hz), 4.48 (2H, s), 4.17-4.24 (1H, m), 3.72-3.79 (1H, m), 3.61-3.68 (2H, m), 3.38-3.44 (1H, m), 2.59-2.69 (1H, m), 2.32-2.33 (1H, m), 2.32-2.40 (1H, m), MS (ES): m/z=356 [M+].

Example 49

(2,4-Dichlorobenzyl)-[1-(4-iodopyridin-2-yl)-pyrrolidin-3-yl]-amine

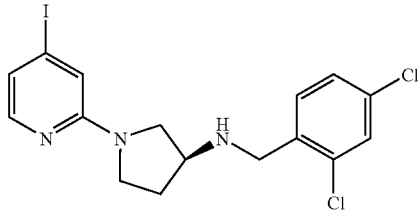

The title compound is prepared essentially as described in Example 48. The hydrochloride salt gives $^1$H NMR (400 MHz, MeOH-d4) δ 7.71 (1H, d, J=8.56 Hz), 7.66-7.69 (2H, m), 7.62 (1H, s), 7.50 (1H, dd, J=8.31, 1.96 Hz), 7.36 (1H, d, J=6.60 Hz), 4.50 (2H, d, J=5.14 Hz), 4.24-4.33 (1H, m), 4.09 (1H, dd, J=11.62, 6.97 Hz), 3.84-3.93 (2H, m), 3.67-3.74 (1H, m), 2.65-2.74 (1H, m), 2.44-2.53 (1H, m), MS (ES): m/z=448 [M+H].

Alternatively, dissolve (S)-2-chloro-4-iodopyridine (500 mg, 2.09 mmol) and (2,4-dichlorobenzyl)-pyrrolidin-3-ylamine dihydrochloride (665 mg, 2.09 mmol) in DMF (10 mL). Add potassium carbonate (1.44 g, 10.4 mmol). Heat the mixture to 125° C. overnight. Cool to room temperature, concentrate and chromatograph on silica gel, eluting with 10:90 to 1:1 ethyl acetate:hexanes, to give the title compounds as an oil. Dissolve the oil in methanol and add 1 N HCl (1 mL) in methanol. Concentrate and dry in a vacuum oven at 60° C. to give the title compound as the hydrochloride salt as a white solid (220 mg, 22%).

Example 50

(S)-[1-(5-Bromopyrimidin-2-yl)-pyrrolidin-3-yl]-(2,4-dichlorobenzyl)-amine

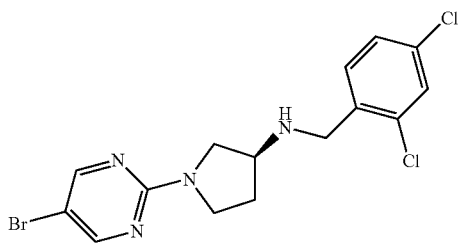

Add to a solution of (S)-3-aminopyrrolidine-1-carboxylic acid tert-butyl ester (10 g, 53.7 mmol) in methanol (100 mL) in one portion to 2,4-dichlorobenzaldehyde (9.6 g, 54.85 mmol). Stir for 22 h., add sodium borohydride (3 g, 79.3 mmol) portionwise (10×0.3 g portions) to the solution maintaining the temperature at about 15° C. to 20° C. and stir for 1 h. Quench the mixture by a dropwise addition of 0.5 N NaOH (110 mL) during 10 min between 17° C.-20° C. and stir for 20 min. Add toluene (100 mL) and extract. Decant the aqueous layer and extract again with toluene (100 mL). Combine the organic layers and use the solution of (S)-3-(2,4-dichlorobenzylamimo)-pyrrolidine-1-carboxylic acid tert-butyl ester directly in the following step.

Heat the toluene solution obtained above at 60° C. Add dropwise aqueous 37% hydrochloric acid (23 mL, 0.27 mol). Stir 30 min until the end of gas emission. Cool to room temperature and extract the organic phase at pH=1. Recover the aqueous layer and add with an aqueous solution of 10 N NaOH (24 mL) in the presence of toluene (50 mL). Extract the product at pH=14. Wash the organic layer with water (25 mL) and concentrate to give (2,4-dichlorobenzyl)-(S)-pyrrolidin-3-ylamine as a yellow oil (12.45 g, 91%).

Add to a solution of (2,4-dichlorobenzyl)-(S)-pyrrolidin-3-ylamine (300 g, 1.22 mol) in acetonitrile (2.25 L) at room temperature diisopropylethylamine (237 g, 1.83 mol) and 5-bromo-2-chloropyrimidine (237 g, 1.23 mol). Reflux for 1 hour. Cool the mixture to 20° C. Add water (45 mL, 2.5 mol) dropwise to give a solid. Stir for 17 h., filter the suspension, and wash the cake with acetonitrile (250 mL), and dry under vacuum at room temperature to give the title compound as a tan solid (377 g, 83%).

Heat a suspension of (S)-1-(5-bromopyrimidin-2-yl)-pyrolidin-3-yl)-(2,4-dichlorobenzyl)-amine (350 g, 0.87 mol) in isopropyl alcohol at 60° C. and add methanesulfonic acid (85 g, 0.875 mol, 1 equiv) dropwise. Heat to reflux. After 1 hour, cool to about 20° C. and stir for 2 hours to give a solid. Filter, wash with isopropyl alcohol (350 mL), and dry under vacuum at 40° C. for 18 hours to give the mesylate salt of the title compound as a white solid (424.6 g, 98%). m.p.=216.5° C.

Alternately, heat a suspension of [(S)-1-(5-bromopyrimidin-2-yl)-pyrrolidin-3-yl]-(2,4-dichlorobenzyl)-amine (1 g, 2.49 mmol) in isopropyl alcohol (10 mL) with water (50 µL) at 60° C. and add methanesulfonic acid (0.165 µL, 2.50 mmol) dropwise. Heat to 60° C. After 30 min, cool to 20° C. and stir for 2 hours to give a solid. Filter, wash with isopropyl alcohol (1 mL), and dry under vacuum at 40° C. for 2 hours to give the title compound as the hydrate of its mesylate salt (1.17 g, 95%).

Example 51

(S)-[1-(6-Fluoropyridin-3-yl)-pyrrolidin-3-yl]-(4-trifluoromethylbenzyl)-amine

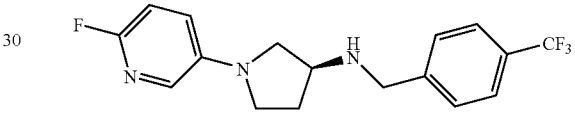

Dissolve (S)-pyrrolidin-3-yl-carbamic acid tert-butyl ester (1.49 g, 8 mmol) in toluene (20 mL). Heat to 110° C. and add 5-bromo-2-fluoropyridine (824 µL, 8 mmol), cesium carbonate (3.9 g, 12 mmol), rac-2,2'-bis(diphenylphosphino)-1,1'-binaphthyl (748 mg, 1.2 mmol) and tris(dibenzylidineacetone)dipalladium(0) (733 mg, 0.8 mmol). Place a nitrogen inlet and condenser on the flask and heat at reflux overnight. Cool and filter the reaction mixture through a pad of Celite® and wash the pad with dichloromethane. Concentrate and chromatograph twice on silica gel, eluting with 0:100 to 25:75 ethyl acetate:dichloromethane, then 10:90 to 40:60 ethylacetate:hexanes, to give (S)-[1-(6-fluoropyridin-3-yl)-pyrrolidin-3-yl]-carbamic acid tert-butyl ester as a brown solid (1.54 g, 68%).

Add trifluoroacetic acid (5 mL) to a solution of [1-(6-fluoropyridin-3-yl)-pyrrolidin-3-yl]-carbamic acid tert-butyl ester (840 mg, 3.0 mmol) in dichloromethane (5 mL). Stir for 1 h then concentrate to dryness. Dissolve the residue in methanol and pass through a column of Dowex® 1x2-200 (Cl$^-$ form). Concentrate the residue and crystallize from methanol and acetone to give (S)-1-(6-fluoropyridin-3-yl)-pyrrolidin-3-ylamine hydrochloride as a tan solid (453 mg, 70%).

Add 4-(trifluoromethyl)benzaldehyde (30 µL, 0.22 mmol) to a solution of 1-(6-fluoropyridin-3-yl)-pyrrolidin-3-ylamine hydrochloride (43 mg, 0.2 mmol) and triethylamine (90 µL, 0.66 mmol) in methanol (1 mL). Vortex the resulting mixture and allow to sit for 18 h. Add sodium borohydride (12-15 mg, 0.3-0.4 mmol). When the bubbling begins to subside, vortex and allow to sit for 1 h. Dilute the reaction mixture with methanol (2 mL) and pour onto a column of Dowex® 50Wx2 (H$^+$ form). Rinse the column with methanol, elute the product with 5% triethylamine in methanol and concentrate. Redissolve the residue in methanol, dilute with acetonitrile and concentrate to dryness to give the title compound as a residue.

Dissolve the residue in methanol and add 1 N HCl (600 μL, 0.6 mmol) in methanol. Concentrate to dryness to give the hydrochloride salt of the title compound as a tan solid (25 mg, 39%). $^1$H NMR (400 MHz, DMSO-d6) δ 9.89 (br s, 2H), 7.87 (d, J=8.5 Hz, 2H), 7.83 (d, J=8.6 Hz, 2H), 7.50 (br, 1H), 7.20 (ddd, J=3.1, 7.0, 8.8 Hz, 1H), 7.03 (dd, J=9.0, 3.2 Hz, 1H), 4.35 (br, 2H), 3.94 (m, J=5.9 Hz, 1H), 3.60 (d, J=6.3 Hz, 2H), 3.50 (m, 1H), 3.28 (m, 1H), 2.37 (m, 2H), MS (ES): m/z=340 [M+1].

The following compounds are prepared essentially as described in Example 51.

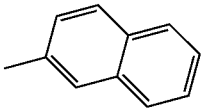

| EX | Compound | R$^2$ |
|---|---|---|
| 52 | (S)-[1-(6-Fluoropyridin-3-yl)-pyrrolidin-3-yl]-naphthalen-2-ylmethylamine<br>$^1$H NMR (400 MHz, DMSO-d$_6$) δ 9.69 (br, 2H), 8.13 (s, 1H), 8.01 (d, J=8.1 Hz, 1H), 7.96 (m, 2H), 7.75 (dd, J=8.5, 1.5 Hz, 1H), 7.58 (m, 2H), 7.52 (br, 1H), 7.22 (ddd, J=8.8, 7.0, 3.2 Hz, 1H), 7.04 (dd, J=9.0, 3.4 Hz, 1H), 4.43 (br, 2H), 4.00 (br, 1H), 3.63 (m, 2H), 3.52 (m, 1H), 3.30 (m, 1H), 2.93 (m, 2H), MS (ES): m/z = 322 [M + H]. | 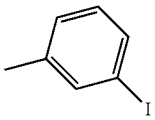 |
| 53 | (S)-[1-(6-Fluoropyridin-3-yl)-pyrrolidin-3-yl]-(3-iodobenzyl)-amine hydrochloride<br>$^1$H NMR (400 MHz, DMSO-d6) δ 9.35 (br, 2H), 8.00 (s, 1H), 7.79 (d, J=8 Hz, 1H), 7.59 (d, J=8 Hz, 1H), 7.52 (br, 1H), 7.26 (t, J=8 Hz, 1H), 7.24 (ddd, J=8.9, 6.7, 3.1 Hz, 1H), 7.04 (dd, J=8.8, 3.1 Hz, 1H), 4.22 (br, 2H), 3.96 (br, 1H), 3.56 (m, 2H), 3.48 (m, 1H), 3.27 (m, 1H), 2.38 (m, 1H), 2.28 (m, 1H), MS (ES): m/z = 398 [M + H]. | 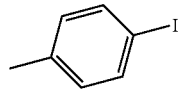 |
| 54 | (S)-[1-(6-Fluoropyridin-3-yl)-pyrrolidin-3-yl]-(4-iodobenzyl)-amine hydrochloride<br>$^1$H NMR (400 MHz, DMSO-d6) δ 9.58 (br, 2H), 7.83 (d, J=8.5 Hz, 2H), 7.50 (br, 1H), 7.40 (d, J=8.5 Hz, 2H), 7.21 (ddd, J= 8.9, 6.7, 3.3 Hz, 1H), 7.03 (dd, J=8.9, 3.3 Hz, 1H), 4.20 (br, 2H), 3.91 (br, 1H), 3.56 (m, 2H), 3.48 (m, 1H), 3.27 (m, 1H), 2.37 (m, 1H), 2.29 (m, 1H), MS (ES): m/z = 398 [M + H]. | 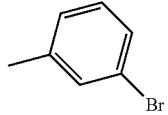 |
| 55 | (S)-[1-(6-Fluoropyridin-3-yl)-pyrrolidin-3-yl]-(3-bromobenzyl)-amine hydrochloride<br>$^1$H NMR (400 MHz, DMSO-d6) δ 9.54 (br, 2H), 7.89 (t, J=1.6 Hz, 1H), 7.66 (m, 1H), 7.62 (d, J=7.7 Hz, 1H), 7.53 (br, 1H), 7.44 (t, J=7.7 Hz, 1H), 7.24 (ddd, J=8.8, 6.8, 3.3 Hz, 1H), 7.06 (dd, J=8.8, 3.1 Hz, 1H), 4.27 (br, 2H), 3.97 (br, 1H), 3.59 (m, 2H), 3.51 (m, 1H), 3.30 (m, 1H), 2.40 (m, 1H), 2.32 (m, 1H), MS (ES): m/z = 398 [M + H]. | 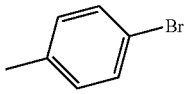 |
| 56 | (S)-[1-(6-Fluoropyridin-3-yl)-pyrrolidin-3-yl]-(4-bromobenzyl)-amine hydrochloride<br>$^1$H NMR (400 MHz, DMSO-d6) δ 9.50 (br, 2H), 7.68 (d, J=8.4 Hz, 2H), 7.55 (d, J=8.4 Hz, 2H), 7.51 (br, 1H), 7.22 (ddd, J= 8.9, 6.9, 3.1 Hz, 1H), 7.04 (dd, J=8.8, 3.1 Hz, 1H), 4.23 (br, 1H), 3.93 (br, 1H), 3.56 (m, 2H), 3.48 (m, 1H), 3.27 (m, 1H), 2.37 (m, 1H), 2.29 (m, 1H), MS (ES): m/z = 350 [M + H]. | 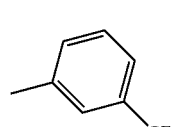 |
| 57 | (S)-[1-(6-Fluoropyridin-3-yl)-pyrrolidin-3-yl]-(3-trifluoromethylbenzyl)-amine hydrochloride<br>$^1$H NMR (400 MHz, DMSO-d6) δ 9.66 (s, 1H), 8.05 (s, 1H), 7.93 (d, J=7.8 Hz, 1H), 7.80 (d, J=7.8 Hz, 1H), 7.69 (t, J=7.8 Hz, 1H), 7.51 (br, 1H), 7.22 (ddd, J=8.9, 7.0, 3.2 Hz, 1H), 7.04 (dd, J=8.7, 3.2 Hz, 1H), 4.36 (br, 2H), 3.99 (m, 1H), 3.60 (d, J= 5.8 Hz, 2H), 3.50 (m, 1H), 3.29 (m, 1H), 2.38 (m, 2H), MS (ES): m/z = 340 [M + H]. | 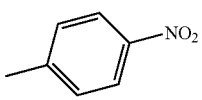 |
| 58 | (S)-[1 (6-Fluoropyridin-3-yl)-pyrrolidin-3-yl]-(4-nitrobenzyl)-amine hydrochloride<br>$^1$H NMR (400 MHz, DMSO-d6) δ 9.80 (br, 2H), 8.32 (d, J=8.8 Hz, 2H), 7.90 (d, J=8.8 Hz, 2H), 7.51 (br, 1H), 7.22 (ddd, J= 8.8, 7.1, 3.1 Hz, 1H), 7.04 (dd, J=8.8, 3.4 Hz, 1H), 4.41 (br, 2H), 3.98 (br, 1H), 3.60 (d, J=5.9 Hz, 2H), 3.50 (m, 1H), 3.28 (m, 1H), 2.38 (m, 2H), MS (ES): m/z = 317 [M + H]. | |

-continued

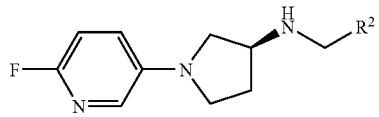

| EX | Compound | R² |
|---|---|---|
| 59 | (S)-[1-(6-Fluoropyridin-3-yl)-pyrrolidin-3-yl]-(2-iodobenzyl)-amine hydrochloride<br>¹H NMR (400 MHz, DMSO-d6) δ 9.64 (br, 2H), 7.97 (dd, J=8.0, 1.4 Hz, 1H), 7.75 (dd, J=7.6, 1.4 Hz, 1H), 7.51 (m, 2H), 7.20 (m, 2H), 7.03 (dd, J=8.8, 3.1 Hz, 1H), 4.31 (br, 2H), 4.08 (br, 2H), 3.68 (dd, J=10.5, 6.7 Hz, 1H), 3.59 (dd, J=10.4, 4.5 Hz, 1H), 3.52 (m, 1H), 3.30 (m, 1H), 2.45 (m, 1H), 2.36 (m, 1H), MS (ES): m/z = 398 [M + H]. | 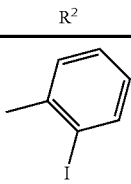 |
| 60 | (S)-[1-(6-Fluoropyridin-3-yl)-pyrrolidin-3-yl]-(2-trifluoromethylbenzyl)-amine hydrochloride<br>¹H NMR (400 MHz, DMSO-d6) δ 9.84 (br, 1H), 9.73 (br, 1H), 8.01 (d, J=7.6 Hz, 1H), 7.82 (m, 2H), 7.66 (t, J = 7.6 Hz, 1H), 7.51 (br, 1H), 7.22 (ddd, J=8.9, 6.9, 3.1 Hz, 1H), 7.04 (dd, J=8.7, 3.3 Hz, 1H), 4.38 (br, 2H), 4.11 (br, 1H), 3.66 (m, 1H), 3.52 (m, 2H), 3.29 (m, 1H), 2.44 (m, 1H), 2.33 (m, 1H), MS (ES): m/z = 340 [M + H]. | 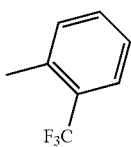 |
| 61 | (S)-(6-Chlorobenzo-[1,3]dioxol-5-yl-methyl)-[1-(6-fluoropyridin-3-yl)-pyrrolidin-3-yl]-amine hydrochloride<br>¹H NMR (400 MHz, MeOH-d4) δ 7.52 (1H, s), 7.30 (1H, ddd, J= 9.11, 6.54, 3.18 Hz), 7.13 (1H, s), 7.05 (1H, s), 6.96 (1H, dd, J=9.05, 2.69 Hz), 6.07 (2H, s), 4.38 (2H, s), 4.11-4.18 (1H, m), 3.59-3.71 (3H, m), 3.31-3.38 (1H, m), 2.61 (1H, m), 2.33 (1H, m), MS (ES): m/z. = 350 [M + H]. | 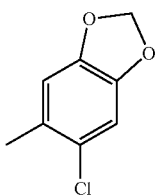 |
| 62 | (S)-2,5-Dichlorothiophen-3-yl-methyl)-[1-(6-fluoropyridin-3-yl)-pyrrolidin-3-yl]-amine hydrochloride<br>¹H NMR (400 MHz, CDCl₃) δ 7.35-7.40 (1H, m), 7.33 (1H, s), 6.96 (1H, ddd, J=9.05, 6.36, 3.18 Hz), 6.74 (1H, dd, J=8.93, 3.06 Hz), 4.04 (2H, s), 3.59-3.69 (2H, m), 3.54 (2H, m), 3.19-3.26 (1H, m), 2.34-2.40 (2H, m), MS (ES): m/z = 346 [M+]. | 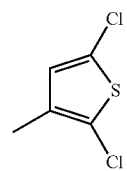 |

Example 63

(S)-Benzo[b]thiophen-3-yl-methyl-[1-(6-fluoropyridin-3-yl)-pyrrolidin-3-yl]-amine

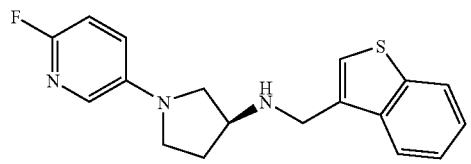

Mix an aliquot (1 mL) of a 0.25 M solution of (S)-[1-(6-fluoropyridin-3-yl)-pyrrolidin-3-yl]-amine (0.25 mmol) in toluene, an aliquot (1 mL) of a 1.0 M solution of benzo[b]thiophene-3-carboxaldehyde (1.0 mmol) in toluene and add a single activated 4 Å molecular sieve. Stir the reactants at room temperature in air. After 16 h add PS-Trisamine (1.5 mmol) and another single activated 4 Å molecular sieve. Stir the reactants at room temperature in air. After 24 h filter the reaction solution to remove the PS-Trisamine, and add an aliquot (2 mL) of a 0.25 M solution of sodium borohydride (0.5 mmol) in ethanol. Stir the reactants at room temperature in air. After 48 h add methanol (2 mL) to the reactants and agitate vigorously. Remove the excess reactants by ion-exchange chromatography using a 5 g SCX-2 cartridge (0.5 mmol/g SO₃H) by wetting it with one column volume of methanol. Apply the mixture to the cartridge and allow it to percolate through the stationary phase (under gravity) into a vial. Wash the cartridge with one column volume of methanol such that these washings also pass into the vial. Replace with a second vial and elute with 3.5N ammonia in methanol (10 mL). Evaporate the solvents from the ammonia washings on a heating block under a stream of nitrogen to give the title compound. ¹H NMR (400 MHz, DMSO-d₆) δ 7.90-7.98 (2H, m), 7.57 (1H, s), 7.39-7.42 (1H, m), 7.35-7.39 (2H, m), 7.08-7.13 (1H, m), 6.96 (1H, dd, J=8.93, 3.30 Hz), 4.01 (2H, s), 3.43-3.50 (2H, m), 3.20-3.27 (1H, m), 3.17 (1H, d, J=5.14 Hz), 3.07-3.13 (1H, m), 2.10-2.18 (1H, m), 1.87-1.95 (1H, m), MS (ES): m/z=328 [M+H].

The following compounds are prepared essentially as described in Example 63.

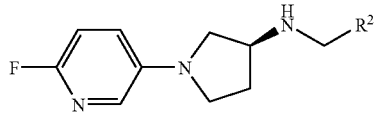

| EX | Compound | R² |
|---|---|---|
| 64 | (S)-(3-Bromo-4-fluorobenzyl)-[1-(6-fluoropyridin-3-yl)-pyrrolidin-3-yl]-amine<br>¹H NMR (400 MHz, DMSO-d₆) δ 7.69 (1H, dd, J=7.09, 1.96 Hz), 7.36-7.41 (2H, m), 7.28-7.33 (1H, m), 7.06-7.12 (1H, m), 6.95 (1H, dd, J=8.80, 3.42 Hz), 3.73 (2H, s), 3.38-3.43 (1H, m), 3.16-3.25 (2H, m), 3.00-3.08 (1H, m), 2.50-2.55 (1H, m), 2.04-2.13 (1H, m), 1.80-1.89 (1H, m), MS (ES): m/z = 368 [M+]. | 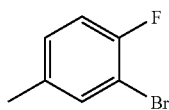 |
| 65 | (S)-[1-(6-Fluoropyridin-3-yl)-pyrrolidin-3-yl]-(4-methoxy-2,5-dimethylbenzyl)-amine<br>¹H NMR (400 MHz, DMSO-d₆) δ 7.37-7.43 (1H, m), 7.01-7.15 (2H, m), 6.95 (1H, dd, J=8.80, 3.42 Hz), 6.71 (1H, s), 3.74 (3H, s), 3.57-3.65 (2H, m), 3.37-3.46 (2H, m), 3.16-3.26 (2H, m), 3.00-3.10 (1H, m), 2.27 (3H, s), 2.08-2.16 (1H, m), 2.07 (3H, s), 1.80-1.94 (1H, m), MS (ES): m/z = 330 [M + H]. | 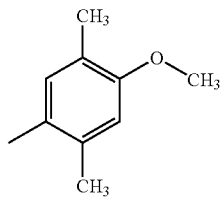 |
| 66 | (S)-[1-(6-Fluoropyridin-3-yl)-pyrrolidin-3-yl]-(3-fluoro-4-trifluoromethylbenzyl)-amine<br>¹H NMR (400 MHz, DMSO-d₆) δ 7.71 (1H, t, J=7.83 Hz), 7.49 (1H, d, J=12.23 Hz), 7.38-7.42 (2H, m), 7.05-7.13 (1H, m), 6.95 (1H, dd, J=8.93, 3.30 Hz), 3.84 (2H, s), 3.42 (1H, dd, J=9.17, 6.24 Hz), 3.27-3.37 (1H, m), 3.15-3.25 (2H, m), 3.00-3.09 (1H, m), 2.05-2.14 (1H, m), 1.81-1.90 (1H, m), MS (ES): m/z = 358 [M + H]. | 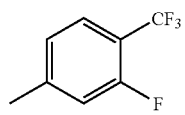 |
| 67 | (S)-(6-Bromobenzo-[1,3]dioxol-5-yl-methyl)-[1-(6-fluoropyridin-3-yl)-pyrrolidin-3-yl]-amine<br>¹H NMR (400 MHz, DMSO-d₆) δ 7.37-7.41 (1H, m), 7.03-7.21 (3H, m), 6.95 (1H, dd, J=8.93, 3.30 Hz), 6.04 (2H, d, J=2.93 Hz), 3.70 (2H, s), 3.36-3.44 (2H, m), 3.15-3.26 (2H, m), 3.05 (1H, dd, J=9.05, 4.16 Hz), 2.05-2.15 (1H, m), 1.81-1.90 (1H, m), MS (ES): m/z = 394 [M+]. | 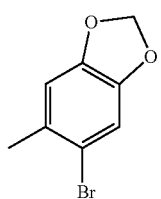 |
| 68 | (S)-(2-Chloro-5-nitrobenzyl)-[1-(6-fluoropyridin-3-yl)-pyrrolidin-3-yl]-amine<br>¹H NMR (400 MHz, DMSO-d₆) δ 8.42 (1H, d, J=2.93 Hz), 8.09-8.13 (1H, m), 7.73 (1H, d, J=8.56 Hz), 7.37-7.42 (1H, m), 7.07-7.14 (1H, m), 6.95 (1H, dd, J=8.93, 3.30 Hz), 3.90 (2H, s), 3.25-3.49 (4H, m), 3.06-3.12 (1H, m), 2.10-2.20 (1H, m), 1.87-1.95 (1H, m), MS (ES): m/z = 351 [M + H]. | 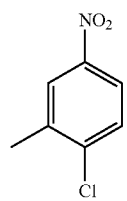 |
| 69 | (S)-(4-Chloro-3-nitrobenzyl)-[1-(6-fluoropyridin-3-yl)-pyrrolidin-3-yl]-amine<br>¹H NMR (400 MHz, DMSO-d₆) δ 8.04 (1H, d, J=1.22 Hz), 7.67-7.73 (2H, m), 7.34-7.43 (1H, m), 7.05-7.12 (1H, m), 6.95 (1H, dd, J=8.80, 3.18 Hz), 3.83 (2H, s), 3.12-3.44 (4H, m), 2.99-3.09 (1H, m), 2.05-2.14 (1H, m), 1.80-1.90 (1H, m), MS (ES): m/z = 351 [M + H]. | 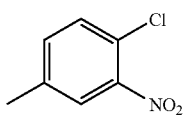 |

Example 70

(S)-4,5-Dichloroisothiazol-3-ylmethyl-[1-(6-fluoro-pyrodin-3-yl)-pyrrolidin-3-yl]-amine

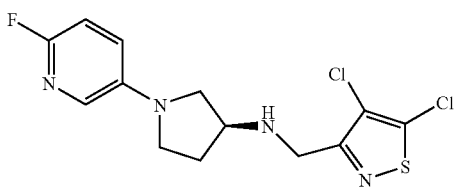

Add sodium borohydride (76 mg, 2.0 mmol) to methyl 4,5-dichloroisothiazole-3-carboxylate (212 mg, 1.0 mmol) in ethanol (10 mL) at room temperature and stir overnight. Add water, extract with dichloromethane three times. Combine the organic layers and wash with saturated aqueous sodium chloride, dry (magnesium sulfate) and concentrate to give (4,5-dichloroisothiazol-3-yl)-methanol as a white solid (141 mg, 77%). $^1$H NMR (400 MHz, MeOH-d4) δ4.66 (s, 2H).

Dissolve (4,5-dichloroisothiazol-3-yl)-methanol (300 mg, 1.63 mmol) in dichloromethane (10 mL). Add pyridinium chlorochromate (703 mg, 3.26 mmol) and stir for 2 h. Pour the mixture onto a column of silica gel, eluting with dichloromethane and concentrate to give 4,5-dichloroisothiazol-3-carbaldehyde as a white solid (193 mg, 65%). $^1$H NMR (400 MHz, MeOH-d4) δ 9.96 (s, 1H).

Dissolve (S)-1-(6-fluoropyridin-3-yl)-pyrrolidin-3-ylamine hydrochloride (100 mg, 0.46 mmol) in methanol (2 mL). Add triethylamine (70 μL, 0.51 mmol) and 4,5-dichloroisothiazol-3-carbaldehyde (93 mg, 0.46 mmol) and stir overnight at room temperature. Add sodium borohydride (28 mg, 0.74 mmol) and stir 1 h. Dilute the mixture with methanol and pour onto a column of Dowex® 50wx4-200 (3 g). Wash with methanol and discard the washing, then elute with 5% triethylamine in methanol. Concentrate to give the title compound as a residue. Dissolve the residue in methanol, add 1 N HCl in methanol (2 mL). Concentrate to almost dry, add acetonitrile and stir over night to give a solid. Filter the solid, wash with acetonitrile, dry in vacuum oven at 50° C. to give the title compound as its hydrochloride salt (120 mg, 68%). δ $^1$H NMR (400 MHz, MeOH-d4) δ 7.54-7.53 (m, 1H), 7.33-7.28 (m, 1H), 6.97 (dd, 1H, J=8.8, 2.6 Hz), 4.57 (s, 2H), 4.27-4.21 (m, 1H), 3.71-3.62 (m, 3H), 3.39-3.33 (m, 1H), 2.66-2.57 (m, 1H), 2.40-2.31 (m, 1H), MS (ES): m/z=347 [M+H].

Example 71

(S)-4-Chloro-2-fluorobenzyl-[1-(6-fluoropyridin-3-yl)-pyrrolidin-3-yl]-amine

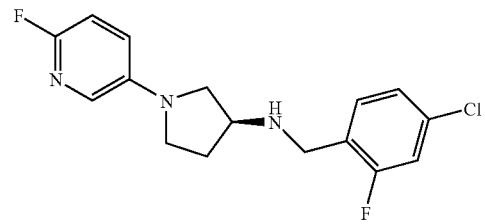

Dissolve 1-(6-fluoropyridin-3-yl)-pyrrolidin-3-ylamine hydrochloride (43 mg, 0.20 mmol) in methanol (1 mL). Add triethylamine (90 μL, 0.65 mmol) and 4-chloro-2-fluorobenzaldehyde (35 mg, 0.22 mmol), vortex and let sit overnight at room temperature. Add sodium borohydride (15 mg, 0.39 mmol) and let sit 1 h. Dilute the mixture with methanol and pour onto a column of Dowex® 50wx4-200 (1.5 g). Wash with methanol and discard the washing, then elute with 5% triethylamine in methanol. Concentrate to give the title compound as a residue. Dissolve the residue in methanol and add 1 N HCl in methanol (0.75 mL). Concentrate and dry in vacuum oven at 50° C. overnight to give the title compound as its hydrochloride salt (53 mg, 74%). $^1$H NMR (400 MHz, MeOH-d4) δ 7.63 (t, 1H, J=8.0 Hz), 7.58-7.57 (m, 1H), 7.45 (dd, 1H, J=9.6, 2.0 Hz), 7.40 (dd, 1H, J=8.0, 2.0 Hz), 7.36-7.32 (m, 1H), 7.00 (dd, 1H, J=8.8, 2.8 Hz), 4.44 (s, 2H), 4.21-4.15 (m, 1H), 3.74-3.61 (m, 3H), 3.42-3.36 (m, 1H), 2.68-2.60 (m, 1H), 2.38-2.29 (m, 1H), MS (ES): m/z=324 [M+H].

The following compounds are prepared essentially as described in Example 71.

| EX | Compound | R² |
|---|---|---|
| 72 | (S)-4-Bromo-2-fluorobenzyl-[1-(6-fluoropyridin-3-yl)-pyrrolidin-3-yl]-amine hydrochloride<br>$^1$H NMR (400 MHz, MeOH-d4) δ 7.61-5.55 (m, 4H), 7.36-7.31 (m, 1H), 7.01 (dd, 1H, J=8.8, 2.4 Hz), 4.42 (s, 2H), 4.18-4.16 (m, 1H), 3.73-3.61 (m, 3H), 3.42-3.36 (m, 1H), 2.68-2.60 (m, 1H), 2.37-2.29 (m, 1H), MS (ES): m/z = 368 ]M + H]. | 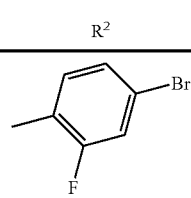 |
| 73 | (S)-2-Chloro-4-fluorobenzyl-[1-(6-fluoropyridin-3-yl)-pyrrolidin-3-yl]-amine hydrochloride<br>$^1$H NMR (400 MHz, MeOH-d4) δ 7.75-7.71 (m, 1H), 7.58-7.57 (m, 1H), 7.48 (dd, 1H, J=8.0, 2.2 Hz), 7.37-7.27 (m, 2H), 7.00 (dd, 1H, J=8.6, 2.6 Hz), 4.51 (s, 2H), 4.26-4.19 (m, 1H), 3.75-3.64 (m, 3H), 3.43-3.37 (m, 1H), 2.71-2.62 (m, 1H), 2.41-2.32 (m, 1H), MS (ES): m/z = 324 ]M + H]. | 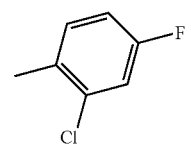 |

-continued

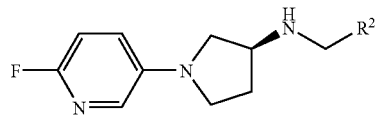

| EX | Compound | R² |
|---|---|---|
| 74 | (S)-5-Bromo-2-fluorobenzyl-[1-(6-fluoropyridin-3-yl)-pyrrolidin-3-yl]-amine hydrochloride<br>¹H NMR (400 MHz, MeOH-d4) δ 7.84 (dd, 1H, J=6.4, 2.2 Hz), 7.75-7.71 (m, 1H), 7.58-7.56 (m, 1H), 7.36-7.31 (m, 1H), 7.30-7.26 (m, 1H), 7.01 (dd, 1H, J=8.8, 2.8 Hz), 4.43 (s, 2H), 4.19-4.16 (m, 1H), 3.74-3.60 (m, 3H), 3.42-3.35 (m, 1H), 2.68-2.60 (m, 1H), 2.37-2.29 (m, 1H), MS (ES): m/z = 368 [M + H]. | 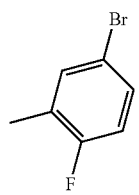 |
| 75 | (S)-3,4-Dichlorobenzyl-[1-(6-fluoropyridin-3-yl)-pyrrolidin-3-yl]-amine hydrochloride<br>¹H NMR (400 MHz, MeOH-d4) δ 7.81 (d, 1H, J=2.0 Hz), 7.70 (d, 1H, J=8.0 Hz), 7.58-7.57 (m, 1H), 7.52 (dd, 1H, J=8.4, 2.4 Hz), 7.36-7.31 (m, 1H), 7.01 (dd, 1H, J=8.8, 2.4 Hz), 4.37 (s, 2H), 4.15-4.13 (m, 1H), 3.72-3.61 (m, 3H), 3.42-3.36 (m, 1H), 2.67-2.58 (m, 1H), 2.37-2.29 (m, 1H), MS (ES): m/z = 340 [M + H]. | 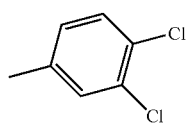 |
| 76 | (S)-3,5-Dichlorobenzyl-[1-(6-fluoropyridin-3-yl)-pyrrolidin-3-yl]-amine hydrochloride<br>¹H NMR (400 MHz, MeOH-d4) δ 7.65-7.61 (m, 3H), 7.58-7.56 (m, 1H), 7.36-7.31 (m, 1H), 7.01 (dd, 1H, J=8.8, 2.0 Hz), 4.38 (s, 2H), 4.16-4.13 (m, 1H), 3.72-3.60 (m, 3H), 3.42-3.36 (m, 1H), 2.64-2.58 (m, 1H), 2.38-2.30 (m, 1H), MS (ES): m/z = 368 [M + H]. | 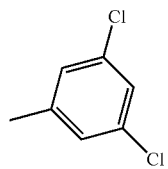 |
| 77 | (S)-2,3-Dichlorobenzyl-[1-(6-fluoropyridin-3-yl)-pyrrolidin-3-yl]-amine hydrochloride<br>¹H NMR (400 MHz, MeOH-d4) δ 7.70 (dd, 1H, J 8.0, 2.0 Hz), 7.61 (dd, 1H, J=8.0, 2.0 Hz), 7.55-7.54 (m, 1H), 7.47-7.43 (m, 1H), 7.34-7.29 (m, 1H), 6.97 (dd, 1H, J=8.4, 2.4 Hz), 4.54 (s, 2H), 4.23-4.19 (m, 1H), 3.73-3.57 (m, 3H), 3.40-3.33 (m, 1H), 2.68-2.59 (m, 1H), 2.38-2.29 (m, 1H), MS (ES): m/z = 340 [M + H]. | 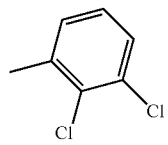 |
| 78 | (S)-2-Chloro-5-trifluoromethylbenzyl-[1-(6-fluoropyridin-3-yl)-pyrrolidin-3-yl]-amine hydrochloride<br>¹H NMR (400 MHz, MeOH-d4) δ 8.02 (s, 1H), 7.84-7.81 (m, 2H), 7.55-7.53 (m, 1H), 7.33-7.28 (m, 1H), 6.96 (dd, 1H, J= 8.8, 2.8 Hz), 4.57 (s, 2H), 4.23-4.20 (m, 1H), 3.72-3.61 (m, 3H), 3.39-3.33 (m, 1H), 2.68-2.59 (m, 1H), 2.38-2.29 (m, 1H), MS (ES): m/z = 374 [M + H]. | 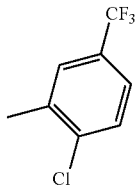 |
| 79 | (S)-(4-Chloro-3-trifluoromethylbenzyl)-[1-(6-fluoropyridin-3-yl)-pyrrolidin-3-yl]-amine hydrochloride<br>¹H NMR (400 MHz, MeOH-d4) δ 8.03 (d, 1H, J=1.6 Hz), 7.81-7.75 (m, 2H), 7.54-7.53 (m, 1H), 7.33-7.28 (m, 1H), 6.97 (dd, 1H, J=8.8, 2.8 Hz), 4.43 (s, 2H), 4.17-4.09 (m, 1H), 3.70-3.60 (m, 3H), 3.39-3.33 (m, 1H), 2.64-2.56 (m, 1H), 2.35-2.27 (m, 1H), MS (ES): (m/e): 374 (M + 1). MS (ES): m/z = 401 [M + H]. | 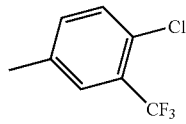 |
| 80 | (S)-(4-Fluoro-3-trifluoromethylbenzyl)-[1-(6-fluoropyridin-3-yl)-pyrrolidin-3-yl]-amine hydrochloride<br>¹H NMR (400 MHz, MeOH-d4) δ 7.96 (dd, 1H, J=6.8, 2.4 Hz), 7.89-7.85 (m, 1H), 7.54-7.46 (m, 2H), 7.33-7.28 (m, 1H), 6.97 (dd, 1H, J=8.8, 2.8 Hz), 4.41 (s, 2H), 4.14-4.11 (m, 1H), 3.69-3.58 (m, 3H), 3.39-3.33 (m, 1H), 2.64-2.55 (m, 1H), 2.37-2.26 (m, 1H), MS (ES): m/z = 358 [M + H]. | 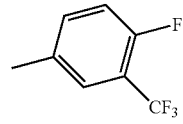 |

-continued

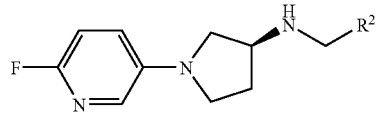

| EX | Compound | R² |
|---|---|---|
| 81 | (S)-(2,5-Dichlorobenzyl)-[1-(6-fluoropyridin-3-yl)-pyrrolidin-3-yl]-amine hydrochloride<br>¹H NMR (400 MHz, MeOH-d4) δ 7.72 (d, 1H, J=2.4 Hz), 7.59-7.51 (m, 3H), 7.33-7.28 (m, 1H), 6.96 (dd, 1H, J=9.2, 2.8 Hz), 4.47 (s, 2H), 4.22-4.15 (m, 1H), 3.71-3.60 (m, 3H), 3.39-3.32 (m, 1H), 2.67-2.58 (m, 1H), 2.37-2.28 (m, 1H), MS (ES): m/z = 340 [M + H]. | 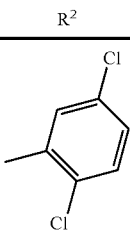 |

Example 82

(S)-(2,4-Dichlorobenzyl)-[1-(5-prop-1-ynyl-pyridin-2-yl)-pyrrolidin-3-yl]-amine

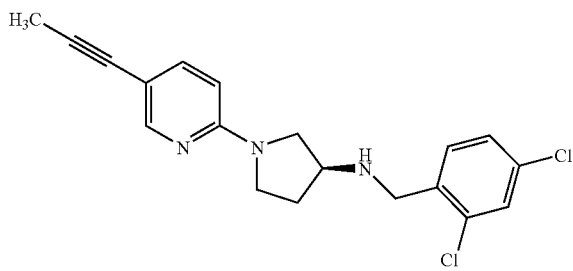

Dissolve (2,4-dichlorobenzyl)-[1-(5-iodopyridin-2-yl)-pyrrolidin-3-yl]-amine hydrochloride (130 mg, 0.27 mmol) in dichloromethane (10 mL) and triethylamine (10 mL). Add trans-dichlorobis(triphenylphosphine)palladium (II) (10 mg, 0.014 mmol) and copper(I) iodide (3 mg, 0.016 mmol). Bubble propyne into the mixture for 1 min. Stir the mixture overnight, filter it through a pad of Celite®, concentrate and chromatograph on silica gel, eluting with 10:90 to 1:1 ethyl acetate:hexanes, to give the title compound as a residue. Dissolve the residue in methanol, add 1 N HCl in methanol (1 mL). Concentrate and dry in vacuum oven at 60° C. to give the title compound as its hydrochloride salt as a light yellow solid (95 mg, 89%). δ ¹H NMR (400 MHz, MeOH-d4) δ 8.03 (d, 1H, J=1.6 Hz), 7.84 (d, 1H, J=8.8 Hz), 7.69-7.68 (m, 2H), 7.49 (dd, 1H, J=8.0, 2.2 Hz), 6.95 (d, 1H, J=9.6 Hz), 4.53-4.45 (m, 2H), 4.28-4.23 (m, 1H), 4.10-4.06 (m, 1H), 3.90-3.83 (m, 2H), 3.72-3.66 (m, 1H), 2.73-2.65 (m, 1H), 2.50-2.41 (m, 1H), 2.03 (s, 3H), MS (ES): m/z=360 [M+H].

Example 83

(S)-[1-(6-Fluoropyridin-3-yl)-pyrrolidin-3-yl]-(2-bromo-4-chlorobenzyl)-amine

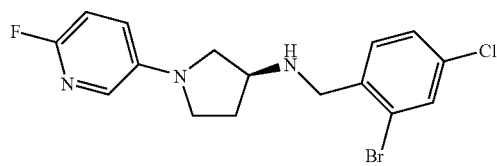

Add borane-THF (1 M in THF, 3.2 mL) complex dropwise to an ice-cooled solution of 2-bromo-4-chlorobenzoic acid (500 mg, 2.1 mmol) in THF (2 mL). Remove the cooling bath and stir overnight. Slowly add water (1 mL) and solid sodium carbonate. Stir 1 h. Filter and wash solids with THF. Chromatograph on silica gel, eluting with 0:100 to 30:70 ethyl acetate:dichloromethane to give 2-bromo-4-chlorobenzyl alcohol as a white solid (378 mg, 80%).

Add pyridinium chlorochromate (432 mg, 2 mmol) to a solution of 2-bromo-4-chlorobenzyl alcohol (200 mg, 0.9 mmol) in dichloromethane (4 mL). Stir the resulting mixture for 2 h. Add diethyl ether (4 mL) and stir for 20-min. Decant the diethyl ether solution. Wash the remaining solids with diethyl ether twice. Combine the diethyl ether solutions and concentrate. Chromatograph on silica gel, eluting with 20:80 to 1:1 ethyl acetate:dichloromethane to give 2-bromo-4-chlorobenzaldehyde as a white solid (167 mg, 85%).

Add 2-bromo-4-chlorobenzaldehyde (159 mg, 0.73 mmol) to a solution of (S)-1-(6-fluoropyridin-3-yl)-pyrrolidin-3-ylamine hydrochloride (144 mg, 0.66 mmol) and triethylamine (292 µL, 2.1 mmol) in methanol (5 mL). Stir the resulting mixture for 18 h. Add sodium borohydride (80 mg, 2.1 mmol). Stir for 1 h. Dilute the reaction mixture with methanol (10 mL) and pour onto a column of Dowex® 50Wx2 (H⁺ form). Rinse the column with methanol then elute the product with 5% triethylamine in methanol. Concentrate and dissolve the residue in methanol. Dilute with acetonitrile and concentrate to give the title compound as a oil. Dissolve the oil in methanol and add excess 1 N HCl in methanol. Concentrate to dryness and crystallize from methanol/acetonitrile to give the title compound as its hydrochloride salt, an off white solid (84 mg, 30%). Elemental analysis calculated for $C_{16}H_{17}BrCl_2FN_3$: C, 45.63; H, 4.07; N, 9.98. Found: C, 45.39; H, 4.02; N, 9.85. MS (ES): m/z=386 [M+H].

Example 84

(S)-[1-(6-Fluoropyridin-3-yl)-pyrrolidin-3-yl]-(4-bromo-2-chlorobenzyl)-amine

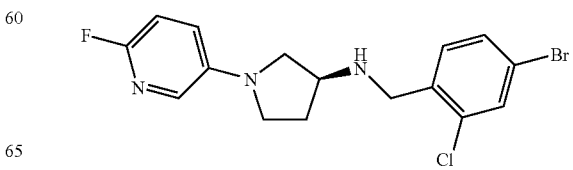

The title compound is prepared essentially as described in Example 82 to give the title compound as its hydrochloride salt, as an off-white solid after crystallization from methanol. Elemental analysis calculated for $C_{16}H_{17}BrCl_2FN_3$: C, 45.63; H, 4.07; N, 9.98. Found: C, 45.78; H, 4.09; N, 9.95. MS (ES): m/z=386 [M+H].

Example 85

(S)-(4-Bromo-2-fluorobenzyl)-[1-(5-bromopyrimidin-2-yl)-pyrrolidin-3-yl]-amine

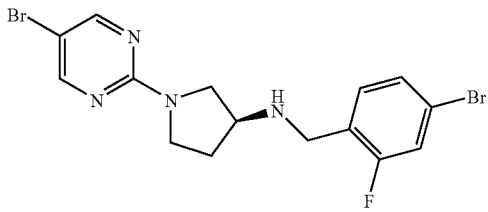

Stir a solution of 5-bromo-2-chloropyrimidine (3.67 g, 19 mmol), (S)-pyrrolidin-3-yl-carbamic acid tert-butyl ester (3.54 g, 19 mmol), and ethyldiisopropylamine (6.6 mL, 38 mmol) in acetonitrile (50 mL) at room temperature for 4 h. Pour into dichloromethane (200 mL) and wash with water (3×). Dry (sodium sulfate) and concentrate to give (S)-[1-(5-bromopyrimidin-2-yl)-pyrrolidin-3-yl]-carbamic acid tert-butyl ester as a tan solid (3.66 g, 71%).

Add trifluoroacetic acid (20 mL) to a solution of (S)-[1-(5-bromopyrimidin-2-yl)-pyrrolidin-3-yl]-carbamic acid tert-butyl ester (3.66 g, 10.7 mmol) in dichloromethane (20 mL). Stir 2 h and concentrate. Dissolve the residue in methanol and pass through a column of Amberjet® 4400 resin (OH-form). Wash the column with methanol and concentrate the eluant. Dissolve the residue in methanol/acetonitrile and add 1 N HCl (25 mL) in methanol. Collect the resulting solid by filtration, wash with acetonitrile and dry the solid to give (S)-1-(5-bromopyrimidin-2-yl)-pyrrolidin-3-ylamine hydrochloride as a tan solid (2.55 g, 85%).

Dissolve 1-(5-bromopyrimidin-2-yl)-pyrrolidin-3-ylamine hydrochloride (60 mg, 0.22 mmol) in methanol (10 mL) and dichloromethane (1 mL). Add triethylamine (100 µL, 0.72 mmol) and 4-bromo-2-fluorobenzaldehyde (87 mg, 0.43 mmol) and stir overnight at room temperature. Add sodium borohydride (25 mg, 0.66 mmol) and stir 1 h. Dilute the mixture with methanol and pour onto a column of Dowex® 50wx4-200. Wash with methanol, then elute with 10% triethylamine in methanol. Concentrate and chromatograph on silica gel, eluting with 20:80 to 1:1 ethyl acetate: hexanes to give the title compound as a residue. Dissolve the residue in methanol and add 1 N HCl in methanol (0.75 mL). Concentrate and dry in a vacuum oven at 60° C. overnight to give the title compound as its hydrochloride salt, as a white solid (80 mg, 80%). $^1$H NMR (400 MHz, MeOH-d4) δ8.45 (s, 2H), 7.57-7.52 (m, 3H), 4.42-4.34 (m, 2H), 4.15-4.09 (m, 1H), 4.04-3.99 (m, 1H), 3.87-3.77 (m, 2H), 3.69-3.62 (m, 1H), 2.63-2.54 (m, 1H), 2.36-2.27 (m, 1H), MS (ES): m/z=429 [M+H].

Example 86

(S)-(1-Bromonaphthalen-2-yl-methyl)-[1-(5-bromopyrimidin-2-yl)-pyrrolidin-3-yl]-amine

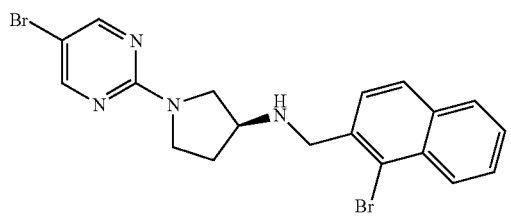

Dissolve 1-(5-bromopyrimidin-3-yl)-pyrrolidin-3-ylamine hydrochloride (60 mg, 0.22 mmol) in methanol (1 mL) and dichloromethane (2 mL). Add triethylamine (100 µL, 0.72 mmol) and 1-bromonaphthalene-2-carbaldehyde (101 mg, 0.43 mmol), vortex and let sit overnight at room temperature. Add sodium borohydride (41 mg, 1.08 mmol) and let sit 20 min. Dilute the mixture with methanol and pour onto a column of Dowex® 50wx4-200. Wash with methanol, then with 5% triethylamine in methanol to give the title compound as a residue. Dissolve the residue in methanol and add 1 N HCl in methanol (1 mL). Concentrate and dry to give the title compound as its hydrochloride salt. Recrystallize from methanol and acetonitrile to give a yellow solid (60 mg, 56%). $^1$H NMR (400 MHz, MeOH-d4) δ8.42 (s, 2H), 8.42-8.37 (m, 1H), 8.05 (d, 1H, J=8.4 Hz), 7.99 (d, 1H, J=7.6 Hz), 7.75-7.65 (m, 3H), 4.78-4.70 (m, 2H), 4.28-4.21 (m, 1H), 4.09-4.04 (m, 1H), 3.91-3.83 (m, 2H), 3.71-3.64 (m, 1H), 2.69-2.60 (m, 1H), 2.43-2.34 (m, 1H), MS (ES): m/z=461 [M+H].

Example 87

(S)-(2,4-Dichlorobenzyl)-[1-(5-ethynylpyridin-2-yl)-pyrrolidin-3-yl]-amine

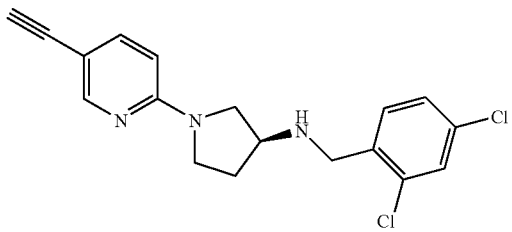

Dissolve (S)-(2,4-dichlorobenzyl)-[1-(5-iodopyridin-2-yl)-pyrrolidin-3-yl]-amine hydrochloride (250 mg, 0.52 mmol) in dichloromethane (15 mL) and triethylamine (10 mL). Add trans-dichlorobis(triphenylphosphine)palladium (II) (24 mg, 0.034 mmol), copper (I) iodide (6 mg, 0.032 mmol) and (trimethylsilyl)acetylene (370 µL, 2.62 mmol). Stir the mixture at room temperature for 1 h, filter through a pad of Celite®, concentrate and chromatograph on silica gel, eluting with a gradient of 20:80 to 1:1 ethyl acetate:hexanes, to give (S)-(2,4-dichlorobenzyl)-[1-(5-trimethylsilanylethynyl-pyridin-2-yl)-pyrrolidin-3-yl]-amine as a yellow oil (190 mg, 88%). MS (ES): m/z=418 [M+H].

Dissolve (S)-(2,4-dichlorbenzyl)-[1-(5-trimethylsilanylethynyl-pyridin-2-yl)-pyrrolidin-3-yl]-amine (190 mg, 0.45 mmol) in THF (10 mL). Add tetrabutylammonium fluoride (1 mL, 1.0 M in THF) dropwise. Stir for 2 h at room temperature. Add water. Extract with ethyl acetate (3×), wash the organic layers with saturated aqueous sodium chloride, dry (magnesium sulfate), concentrate and chromatograph on silica gel, eluting with a 20:80 to 1:1 ethyl acetate:hexanes, to give the title compound as a yellow oil (141 mg, 90%). Dissolve the oil in methanol and add fumaric acid (47 mg, 0.41 mmol) in methanol. Concentrate most of the solvent, add acetonitrile and stir overnight. Filter the solid and dry in a vacuum oven at 60° C. overnight to give the title compound as its fumarate salt (139 mg, 74%). $^1$H NMR (400 MHz, MeOH-d4) δ8.15 (d, 1H, J=2.4 Hz), 7.59-7.54 (m, 3H), 7.39 (dd, 1H, J=8.0, 2.0 Hz), 6.72 (s, 2H), 6.50 (d, 1H, J=8.8 Hz), 4.20-4.12 (m, 2H), 3.83-3.76 (m, 2H), 3.70-3.64 (m, 1H), 3.59-3.47 (m, 2H), 3.44 (s, 1H), 2.46-2.38 (m, 1H), 2.18-2.09 (m, 1H), MS (ES): m/z=346 [M+H].

The following compounds are prepared essentially as described in Example 85.

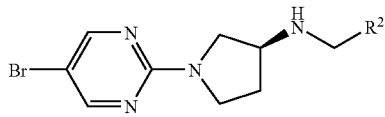

| | | |
|---|---|---|
| 88 | (S)-[1-(5-Bromopyrimidin-2-yl)-pyrrolidin-3-yl]-(2-fluoro-5-trifluoromethylbenzyl)-amine hydrochloride<br>$^1$H NMR (400 MHz, MeOH-d4) δ 8.45 (s, 2H), 8.03-8.01 (m, 1H), 7.91-7.87 (m, 1H), 7.49 (t, 1H, J=8.8 Hz), 4.53-4.46 (m, 2H), 4.19-4.12 (m, 1H), 4.05-4.01 (m, 1H), 3.87-3.79 (m, 2H), 3.69-3.63 (m, 1H), 2.64-2.56 (m, 1H), 2.37-2.29 (m, 1H), MS (ES): m/z = 419 [M + H]. | 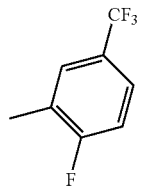 |
| 89 | (S)-[1-(5-Bromopyrimidin-2-yl)-pyrrolidin-3-yl]-(3-fluoro-5-trifluoromethylbenzyl)-amine hydrochloride<br>$^1$H NMR (400 MHz, MeOH-d4) δ 8.43 (s, 2H), 7.77 (s, 1H), 7.66-7.61 (m, 2H), 4.49-4.41 (m, 2H), 4.15-4.09 (m, 1H), 4.04-3.99 (m, 1H), 3.86-3.78 (m, 2H), 3.69-3.62 (m, 1H), 2.62-2.53 (m, 1H), 2.37-2.28 (m, 1H), MS (ES): m/z = 419 [M + H]. | 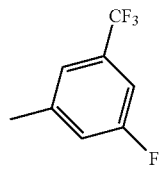 |
| 90 | (S)-[1-(5-Bromopyrimidin-2-yl)-pyrrolidin-3-yl]-(2-fluoro-4-trifluoromethylbenzyl)-amine hydrochloride<br>$^1$H NMR (400 MHz, MeOH-d4) δ 8.44 (s, 2H), 7.82 (d, 1H, J= 8.0 Hz), 7.67-7.65 (m, 2H), 4.53-4.45 (m, 2H), 4.18-4.12 (m, 1H), 4.05-4.00 (m, 1H), 3.87-3.79 (m, 2H), 3.69-3.63 (m, 1H), 2.64-2.55 (m, 1H), 2.37-2.29 (m, 1H), MS (ES): m/z = 419 [M + H]. | 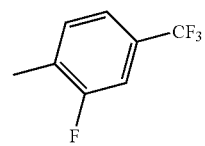 |
| 91 | (S)-[1-(5-Bromopyrimidin-2-yl)-pyrrolidin-3-yl]-(3-chloro-2-fluoro-5-trifluoromethylbenzyl)-amine hydrochloride<br>MS (ES): m/z = 453 [M + H]. | 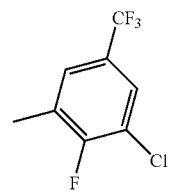 |
| 92 | (S)-[1-(5-Bromopyrimidin-2-yl)-pyrrolidin-3-yl]-(2,3-difluoro-5-trifluoromethylbenzyl)-amine hydrochloride<br>$^1$H NMR (400 MHz, MeOH-d4) δ 8.42 (s, 2H), 7.68-7.57 (m, 2H), 4.56-4.48 (m, 2H), 4.19-4.13 (m, 1H), 4.04-3.99 (m, 1H), 3.86-3.79 (m, 2H), 3.69-3.63 (m, 1H), 2.64-2.55 (m, 1H), 2.37-2.28 (m, 1H), MS (ES): m/z = 437 [M + H]. | 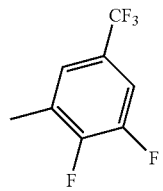 |
| 93 | (S)-[1-(5-Bromopyrimidin-2-yl)-pyrrolidin-3-yl]-(2-chloro-5-trifluoromethylbenzyl)-amine hydrochloride<br>$^1$H NMR (400 MHz, MeOH-d4) δ 8.47 (s, 2H), 8.04 (s, 1H), 7.84-7.78 (m, 2H), 4.62-4.54 (m, 2H), 4.25-4.19 (m, 1H), 4.08-4.03 (m, 1H), 3.90-3.83 (m, 2H), 3.71-3.65 (m, 1H), 2.67-2.59 (m, 1H), 2.42-2.33 (m, 1H), MS (ES): m/z = 435 [M + H]. | 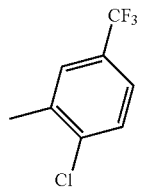 |

-continued

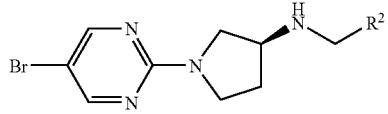

| | | |
|---|---|---|
| 94 | (S)-(2,4-Bis-trifluoromethylbenzyl)-[1-(5-bromopyrimidin-2-yl)-pyrrolidin-3-yl]-amine hydrochloride<br>$^1$H NMR (400 MHz, MeOH-d4) δ 8.43 (s, 2H), 8.16-8.14 (m, 2H), 8.01 (d, 1H, J=8.8 Hz), 4.64-4.55 (m, 2H), 4.28-4.21 (m, 1H), 4.07-4.02 (m, 1H), 3.87-3.79 (m, 2H), 3.70-3.63 (m, 1H), 2.67-2.58 (m, 1H), 2.37-2.28 (m, 1H), MS (ES): m/z = 469 [M + H]. | 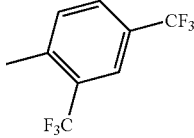 |
| 95 | (S)-[1-(5-Bromopyrimidin-2-yl)-pyrrolidin-3-yl]-(5-chloro-2-trifluoromethylbenzyl)-amine hydrochloride<br>$^1$H NMR (400 MHz, MeOH-d4) δ 8.41 (s, 1H), 7.86 (s, 1H), 7.85 (d, 1H, J=8.4 Hz), 7.69 (d, 1H, J=8.8 Hz), 4.49-4.40 (m, 2H), 4.13-4.10 (m, 1H), 4.02-3.97 (m, 1H), 3.84-3.72 (m, 2H), 3.67-3.61 (m, 1H), 2.61-2.52 (m, 1H), 2.30-2.22 (m, 1H), MS (ES): m/z = 435 [M + H]. | 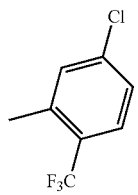 |
| 96 | (S)-[1-(5-Bromopyrimidin-2-yl)-pyrrolidin-3-yl]-(5-fluoro-2-trifluoromethylbenzyl)-amine hydrochloride<br>$^1$H NMR (400 MHz, MeOH-d4) δ 8.42 (s, 2H), 7.93 (dd, 1H, J= 8.8, 5.6 Hz), 7.59 (dd, 1H, J=8.4, 2.4 Hz), 7.47-7.42 (m, 1H), 4.55-4.46 (m, 2H), 4.21-4.18 (m, 1H), 4.05-4.00 (m, 1H), 3.86-3.76 (m, 2H), 3.67-3.62 (m, 1H), 2.65-2.56 (m, 1H), 2.34-2.26 (m, 1H), MS (ES): m/z = 419 [M + H]. | 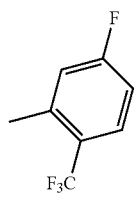 |
| 97 | (S)-[1-(5-Bromopyrimidin-2-yl)-pyrrolidin-3-yl]-(2,5-dichlorobenzyl)-amine hydrochloride<br>MS(ES): m/z = 401 [M + H]. | 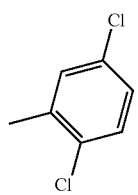 |

Example 98

(S)-(2,4-Dichlorobenzyl)-[1-(5-vinylpyridin-2-yl)-pyrrolidin-3-yl]-amine

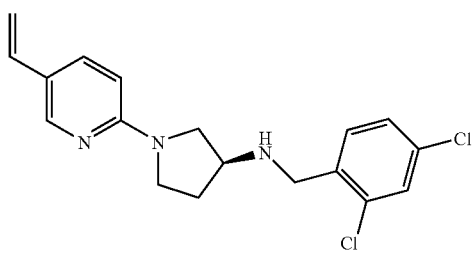

Dissolve (S)-(2,4-dichlorobenzyl)-[1-(5-iodopyridin-2-yl)-pyrrolidin-3-yl]-amine hydrochloride (200 mg, 0.41 mmol) in DMF (7 mL) and triethylamine (60 μL). Add tetrakis(triphenylphosphine)palladium (0) (24 mg, 0.021 mmol) and tributyl(vinyl)tin (150 μL, 0.49 mmol). Heat the mixture at 65° C. overnight. Cool to room temperature, dilute with 1 N HCl (15 mL). Wash the mixture with dichloromethane (3×). Basify the aqueous solution to about pH=9 by adding solid potassium carbonate. Extract with dichloromethane (3×), dry (magnesium sulfate), concentrate and chromatograph on silica gel, eluting with 10:90 to 1:1 ethyl acetate:hexanes, to give the title compound as a residue. Dissolve the residue in methanol, add 1 N HCl in methanol (1 mL). Concentrate and dry in a vacuum oven at 60° C. to give the title compound as its hydrochloride salt (97 mg, 56%): $^1$H NMR (400 MHz, MeOH-d4) δ8.30 (dd, 1H, J=8.8, 2.0 Hz), 7.97 (d, 1H, J=2.4 Hz), 7.71 (d, 1H, J=8.0 Hz), 7.68 (d, 1H, J=1.6 Hz), 7.50 (dd, 1H, J=8.0, 2.2 Hz), 7.16 (d, 1H, J=9.2 Hz), 6.70 (dd, 1H, J=17.6, 11.2 Hz), 5.87 (d, 1H, J=17.6 Hz), 5.40 (d, 1H, J=11.2 Hz), 4.55-4.47 (m, 2H), 4.34-4.28 (m, 1H), 4.18-4.13 (m, 1H), 3.97-3.91 (m, 2H), 3.80-3.74 (m, 1H), 2.77-2.68 (m, 1H), 2.55-2.46 (m, 1H), MS (ES): m/z 348 [M+H].

Example 99

(S)-(2,4-Dichlorobenzyl)-[1-(4-ethynylpyridin-2-yl)-pyrrolidin-3-yl]-amine

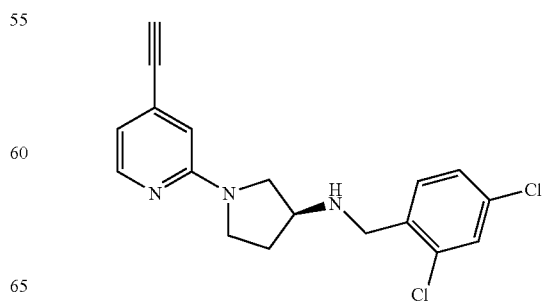

The title compound is prepared essentially as described in Example 86 to give the title compound as its hydrochloride salt (30 mg, 15%). ¹H NMR (400 MHz, MeOH-d4) δ8.00 (d, 1H, J=5.2 Hz), 7.55 (s, 1H), 7.54 (d, 1H, J=5.2 Hz), 7.38 (dd, 1H, J=8.0, 2.0 Hz), 6.71 (s, 2H), 6.64 (dd, 1H, J=5.2, 1.2 Hz), 6.60 (s, 1H), 4.18-4.11 (m, 2H), 3.78-3.76 (m, 2H), 3.67-3.61 (m, 1H), 3.52-3.44 (m, 2H), 2.43-2.37 (m, 1H), 2.16-2.08 (m, 1H), MS (ES): m/z=346 [M+H].

The following compounds are prepared essentially as described in Example 28.

| EX | Compound | R⁴ |
|---|---|---|
| 100 | (3R, S)-(4R, S)-trans-1-(5-bromopyrimidin-2-yl)-4-(2,4-dichlorobenzylamino)-pyrrolidin-3-ol hydrochloride<br>¹H NMR (400 MHz, MeOH-d4) δ 8.43 (2H, s), 7.63-7.69 (2H, m), 7.49 (1H, dd, J=8.31, 1.96 Hz), 4.64-4.69 (2H, m), 4.49 (1H, d, J=13.45 Hz), 4.12 (1H, dd, J=12.47, 7.34 Hz), 4.05 (1H, dd, J=11.98, 6.60 Hz), 3.90-3.95 (1H, m), 3.76 (1H, dd, J=12.47, 5.87 Hz), 3.47 (1H, dd, J=11.86, 5.50 Hz), MS (ES): m/z = 418 [M+]. | —OH |
| 101 | [1-(5-Bromopyrimidin-2-yl)-4-fluoropyrrolidin-3-yl]-(2,4-dichlorobenzyl)-amine hydrochloride<br>¹H NMR (400 MHz, MeOH-d4) δ 8.42 (2H, s), 7.66 (1H, d, J=8.31 Hz), 7.63 (1H, d, J=2.20 Hz), 7.47 (1H, dd, J=8.31, 2.20 Hz), 5.61 (1H, dt, J=53.80, 3.18 Hz), 4.39-4.50 (2H, m), 4.23-4.28 (1H, m), 4.12-4.23 (1H, m), 4.01-4.11 (1H, m), 3.83 (1H, ddd, J=40.23, 14.31, 3.18 Hz), 3.53-3.59 (1H, m), MS (ES): m/z = 421 [M + H]. | —F |
| 102 | [1-(5-Bromopyrimidin-2-yl)-4-methylpyrrolidin-3-yl]-(2,4-dichlorobenzyl)-amine hydrochloride<br>¹H NMR (400 MHz, MeOH-d4) δ 8.43 (2H, s), 7.70 (1H, d, J=8.31 Hz), 7.67 (1H, d, J=2.20 Hz), 7.50 (1H, dd, J=8.31, 2.20 Hz), 4.49 (2H, s), 4.03-4.15 (2H, m), 3.78-3.84 (1H, m, J=11.62, 6.72 Hz), 3.72-3.77 (1H, m, J=11.49, 6.60 Hz), 3.54-3.59 (1H, m, J=11.49, 3.91 Hz), 2.85-2.96 (1H, m, J=10.58, 6.72, 6.42 Hz), 1.24 (3H, d, J=7.09 Hz), MS (ES): m/z = 417 [M + H]. | —CH₃ |

The following compounds of Examples 103-106 are prepared essentially as described in Example 1:

Example 103

(R,S)-[1-(5-Bromopyridin-2-yl)-3-methylpyrrolidin-3-yl]-(2,4-dichlorobenzyl)-amine

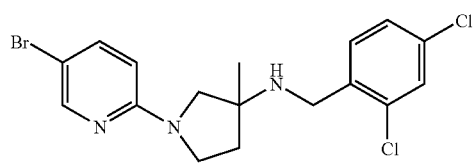

Its hydrochloride salt gives ¹H NMR (400 MHz, CDCl₃) δ 8.15 (1H, d, J=2.69 Hz), 7.49 (1H, dt, J=5.87, 2.93 Hz), 7.41 (1H, dd, J=8.07, 2.93 Hz), 7.35 (1H, d, J=2.69 Hz), 7.17-7.23 (1H, m), 6.23 (1H, dd, J=8.93, 3.06 Hz), 3.83-3.93 (2H, m), 3.55-3.63 (1H, m), 3.45-3.54 (2H, m), 3.35 (1H, dd, J=10.39, 2.81 Hz), 2.08-2.19 (1H, m), 1.91-2.02 (1H, m), 1.41 (3H, d, J=2.93 Hz), MS (ES): m/z=415 [M+].

Example 104

(R,S)-(2,4-Dichlorobenzyl)-[1-(6-fluoropyridin-3-yl)-3-methylpyrrolidin-3-yl]-amine

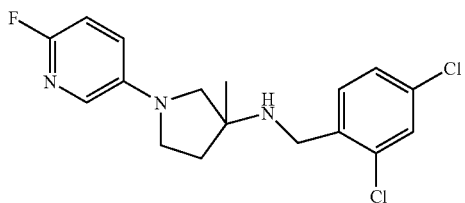

Its hydrochloride salt gives ¹H NMR (300 MHz, CDCl₃) δ 7.37-7.43 (1H, m), 7.30-7.37 (1H, m), 7.14-7.30 (2H, m), 6.83-6.92 (1H, m), 6.77 (1H, dd, J=8.38, 3.30 Hz), 3.84 (2H, s), 3.37-3.50 (1H, m), 3.24-3.37 (2H, m), 3.16 (1H, d, J=9.04 Hz), 2.05-2.19 (1H, m), 1.88-2.02 (1H, m), 1.30-1.45 (3H, m, J=1.51 Hz), MS (ES): m/z=354 [M+].

Example 105 and Example 106

(3S)-[1-(2,4-Dichlorophenyl)-ethyl]-1-(6-fluoropyridin-3-yl)-pyrrolidin-3-yl-amine

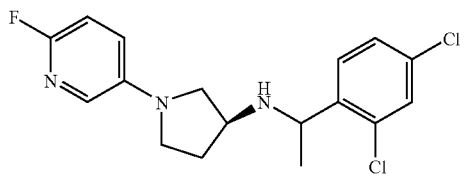

Isomers are separated on silica gel, eluting with 0:100 to 45:55 ethyl acetate:2-methylpentane. EXAMPLE 105 Isomer-1, its hydrochloride salt gives: $^1$H NMR (400 MHz, MeOH-d4) δ 7.74 (1H, d, J=8.56 Hz), 7.65 (1H, d, J=1.96 Hz), 7.54 (1H, dd, J=8.56, 2.20 Hz), 7.44-7.52 (1H, m), 7.25 (1H, m), 6.95 (1H, dd, J=8.93, 2.81 Hz), 3.98 (1H, m), 3.54-3.66 (3H, m), 3.24-3.34 (2H, m), 2.43-2.54 (1H, m), 2.44-2.25 (1H, m), 1.73 (3H, d, J=6.85 Hz), MS (ES): m/z=354 [M+].

EXAMPLE 106 Isomer-2, its hydrochloride salt gives: $^1$H NMR (400 MHz, MeOH-d4) δ 7.74 (1H, d, J=8.31 Hz), 7.66 (1H, d, J=2.20 Hz), 7.55 (1H, dd, J=8.44, 2.08 Hz), 7.46-7.51 (1H, m), 7.26 (1H, m), 6.94 (1H, dd, J=8.80, 2.93 Hz), 3.99 (1H, m), 3.55-3.65 (3H, m), 3.26-3.34 (2H, m), 2.46-2.55 (1H, m), 2.18-2.27 (1H, m), 1.74 (3H, d, J=6.85 Hz), MS (ES): m/z=354 [M+].

Example 107

(S)-(2,4-Dichlorobenzyl)-[1-(5-methylpyrimidin-2-yl)-pyrrolidin-3-yl]-amine

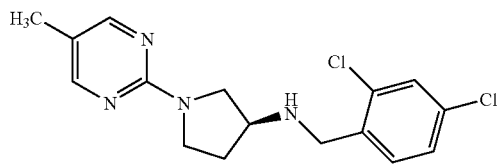

Add trimethylaluminium (2 N in hexanes, 190 μL, 0.32 mmol) and tetrakis(triphenylphosphine)palladium (0) (26 mg, 0.022 mmol) to (S)-[1-(5-bromopyrimidin-2-yl)-pyrrolidin-3-yl]-(2,4-dichlorobenzyl)-amine in dry THF (1.5 mL) and heat at 65° C. for 2 h, then add extra trimethylaluminium (2 N in hexanes, 190 μL, 0.32 mmol) and tetrakis(triphenylphosphine)palladium (0) (26 mg, 0.022 mmol) and heat at 65° C. for 30 min and 48 h at room temperature. Add water and extract with chloroform. Combine the organic layers and wash with saturated aqueous sodium chloride, dry (magnesium sulfate), concentrate and dissolve the residue in methanol (2 mL) and deposit onto an SCX-2 cartridge; eluting with methanol, then with 2 N ammonia in methanol. Concentrate the ammonia washing and chromatograph the residue by preparative mass guided chromatography to give the title compound as a residue. Treatment of the residue essentially as described in Example 1 gives the title compound as its hydrochloride. $^1$H NMR (300 MHz, CDCl$_3$) δ 8.16 (2H, s), 7.37 (2H, dd, J=5.09, 3.01 Hz), 7.21 (1H, dd, J=8.29, 2.07 Hz), 3.90 (2H, d, J=4.90 Hz), 3.68-3.83 (2H, m), 3.58 (1H, m), 3.39-3.51 (2H, m), 2.14-2.25 (1H, m), 2.12 (3H, s), 1.84-1.96 (1H, m), MS (ES): m/z=337 [M+].

Example 108

(S)-(2,4-Dichlorobenzyl)-[1-(5-phenylpyridin-2-yl)-pyrrolidin-3-yl]-amine

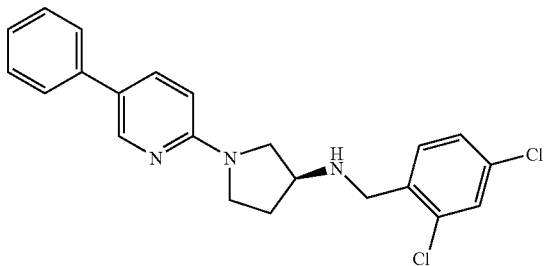

Dissolve a mixture of (S)-[1-(5-bromopyridin-2-yl)-pyrrolidin-3-yl]-(2,4-dichlorobenzyl)-amine (330 mg, 0.82 mmol), phenylboronic acid (100 mg, 0.82 mmol), tetakis (triphenylphosphine)palladium (0) (50 mg, 0.04 mmol), 2 N sodium carbonate solution (0.5 mL, 3.3 mmol) in 15:85 ethylene glycol dimethyl ether:methanol (8 mL) and heat in microwave (CEM Discover, 200W) at 80° C. for 20 min. Concentrate to a residue and dissolve in chloroform and wash with saturated aqueous sodium chloride, dry (magnesium sulfate), concentrate, and chromatograph on silica gel, eluting with 0:100 to 10:90 methanol:chloroform, then second column eluting with 0:100 to 50:50 ethyl acetate:2-methylpentane) to give the title compound as a residue. Treatment of the residue essentially as described in Example 1 gives the title compound as its hydrochloride. $^1$H NMR (400 MHz, DMSO-d6) δ 8.32 (1H, d, J=1.96 Hz), 8.12 (1H, dd, J=9.05, 2.20 Hz), 7.71-7.77 (2H, m), 7.64 (2H, d, J=7.58 Hz), 7.54 (1H, dd, J=8.31, 2.20 Hz), 7.47 (2H, t, J=7.58 Hz), 7.37 (1H, d, J=7.34 Hz), 6.93 (1H, d, J=9.05 Hz), 4.36 (2H, d, J=4.65 Hz), 4.09-4.16 (1H, m), 3.91-4.00 (2H, m), 3.82-3.89 (1H, m), 3.71-3.80 (1H, m), 2.50-2.56 (1H, m), 2.37-2.45 (1H, m), MS (ES): m/z=398 [M+].

Example 109

(S)-(2,4-Dichlorobenzyl)-(1-isoquinolin-3-ylpyrrolidin-3-yl)-amine

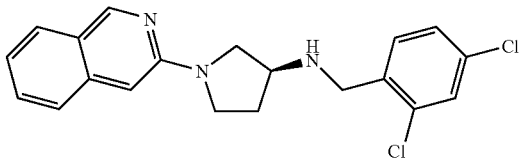

Add trifluoromethanesulfonic anhydride (383 μL, 2.3 mmol) dropwise to a suspension of isoquinolin-3-ol (274 mg, 1.89 mmol) and triethylamine (524 μL, 3.8 mmol) in dichloromethane (12 mL). Stir for 40 min, then load onto a silica column and elute with dichloromethane to give trifluoromethanesulfonic acid isoquinolin-3-yl ester as a white solid (505 mg, 97%).

Add trifluoromethanesulfonic acid isoquinolin-3-yl ester (505 mg, 1.82 mmol) to a solution of S-(2,4-dichlorobenzyl)-pyrrolidin-3-yl-amine dihydrochloride (57 mg, 1.8 mmol) and diisopropylethylamine (1.3 mL, 7.3 mmol) in N-methylpyrrolidine (3 mL). Heat the resulting mixture for 18 h at 160° C. Cool and add 1 N HCl (10 mL) and water (100 mL). Extract three times with dichloromethane. Extract the combined organic washes with 0.25 N HCl. Discard the organic washes. Basify all aqueous layers to pH>10 with 2 N NaOH and extract three times with dichloromethane. Dry (sodium sulfate), concentrate and chromatography on silica gel eluting with 1:1 ethyl acetate:hexanes to give the title compound. Dissolve the title compound in 1 N HCl in methanol and concentrate to give the hydrochloride of the title compound as a yellow solid (220 mg, 27%). MS (ES): m/z=372 [M+H]; Anal. Calc'd for C$_{20}$H$_{21}$Cl$_4$FN$_3$: C, 53.96, H, 4.75, N, 9.44; Found: C, 53.55; H, 4.76; N, 9.32.

Example 110

(S)-[1-(5-Bromopyrimidin-2-yl)-pyrrolidin-3-yl]-(2,4-dichlorobenzyl)-amine

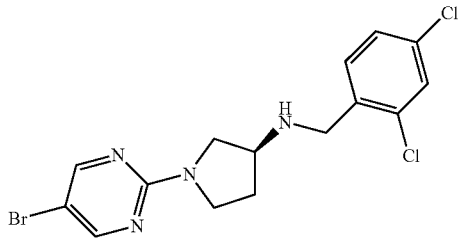

Combine 2-chloro-5-bromopyrimidine (20.0 g, 1.0 eq) and isopropanol (200 mL). Add (S)-3-aminopyrrolidine (8.91 g, 1.0 eq) dropwise over about 30 minutes. Add isopropanol (10 mL) and heat to 50° C.-60'. After 4 hours, cool to 20° C.-25° C. over about 1 hour, stir for about 1 hour, and then collect the solid by filtration. Rinse the solid with isopropanol (2×25 mL) and dry under vacuum at about 40° C. to give (S)-1-(5-bromopyrimidin-2-yl)-pyrrolidine-3-amine as its hydrochloride salt.

Combine (S)-1-(5-bromopyrimidin-2-yl)-pyrrolidine-3-amine (10.0 g, 35.84 mmol) and 30% aqueous sodium hydroxide (1.18 equiv., 4 mL) in water (30 mL), THF (75 mL), and toluene (75 mL). Separate the layers, extract the aqueous layer with 1:1 THF:toluene (50 mL). Combine the organic layers and extract with water (10 mL). Evaporate the organic layer at reduced pressure to give a residue. Combine the residue and toluene (75 mL) and evaporate at reduced pressure to give a residue. Again, combine the residue and toluene (75 mL) and evaporate at reduced pressure to give a residue Combine the residue and toluene (12.9 g) and dry THF (53.2 g), add 2,4-dichlorobenzaldehyde (0.94 equivalent, 33.6 mmol, 6.0 g), and stir. After 1 hour, add sodium triacetoxyborohydride (65.9 mmol, 2.5 equiv., 14.4 g) in 5 portions over about 50 minutes. After 22 hours, slowly add water (16 mL), Stir for 2 hours and then basify to pH=14 by addition of 30% aqueous sodium hydroxide (20 mL). Separate the aqueous layer and extract with 1/1 toluene/THF (120 mL). Combine the organic layers and extract with water (30 mL). Evaporate the solvents at reduced pressure to give a residue. Combine the residue and isopropanol (130 mL) and evaporate at reduced pressure to give a residue. Twice more, combine the residue and isopropanol (130 mL) and evaporate at reduced pressure to give a mass of about 90 g. Slowly cool to room temperature and agitate for about 3 hours to give a solid. Collect the solid by filtration, rinse with isopropanol (10 mL), and dry at 40° C. under vacuum for 15 hours to give the title compound.

Combine the title compound (35 g, 87.06 mmol) and isopropanol (280 mL). Add water (20 eq., 1.7 moles, 31.34 gr) and heat to about 62° C. with stirring until a clear solution is obtained. Add methanesulfonic acid (2 eq., 174.08 mmol, 16.73 g in 70 mL isopropanol) drop-wise over about 2 minutes. Cool to 45° C. over about 30 minutes. After 40 minutes, cool to room temperature and continue stirring. After 1 hour, collect the solid by filtration, rinse with isopropanol (70 mL), and dry at 20° C. under reduced pressure (200 mbar) to give the title compound as its mesylate salt hemihydrate.

Example 111

(3S)-[1-(6-Bromopyridin-2-yl)-pyrrolidin-3-yl]-(2,4-dichlorobenzyl)-amine

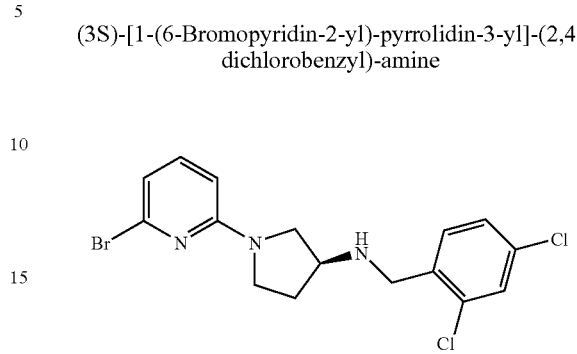

Add 2,6-dibromopyridine (500 mg, 2.11 mmol), pyrrolidin-3-ylcarbamic acid tert-butyl ester (372 mg, 2.00 mmol), tris(dibenzylideneacetone)dipalladium (0) (193 mg, 0.21 mmol), 2,2'-bis(diphenylphosphino)-1,1'-binaphthyl (526 mg, 0.84 mmol), and cesium carbonate (1.37 g, 4.21 mmol) to a dry flask under nitrogen. Add degassed anhydrous toluene (10 mL) to the flask. Heat at 100° C. for one hour. Cool to room temperature and dilute with dichloromethane, filter through a pad of Celite®, concentrate to give a residue. Chromatograph the residue on silica gel eluting with 10:90 to 20:80 ethyl acetate:hexanes to give (3S)-[1-(6-bromopyridin-2-yl)-pyrrolidin-3-yl]-carbamic acid tert-butyl ester (260 mg, 38%). $^1$H NMR (400 MHz, MeOH-d4) δ 7.31 (t, 1H, J=8.0 Hz), 6.66 (d, 1H, J=8.0 Hz), 6.36 (d, 1H, J=8.0 Hz), 4.22-4.16 (m, 1H), 3.68-3.64 (m, 1H), 3.56-3.49 (m, 1H), 3.47-3.41 (m, 1H), 3.26-3.22 (m, 1H), 2.26-2.18 (m, 1H), 1.98-1.90 (m, 1H), 1.44 (s, 9H).

Combine (3S)-[1-(6-bromopyridin-2-yl)-pyrrolidin-3-yl]-carbamic acid tert-butyl ester (260 mg, 0.76 mmol) and dichloromethane (10 mL). Add trifluoroacetic acid (2 mL) and stir at room temperature for 4 hours. Concentrate and dissolve in methanol. Load onto Dowex® 1×2-200 column and elute with methanol. Concentrate and add acetone to give a solid. Filter the solid to give (3S)-1-(6-bromopyridin-2-yl)-pyrrolidin-3-ylamine hydrochloride (187 mg, 88%). $^1$H NMR (400 MHz, MeOH-d4) δ 7.39 (t, 1H, J=7.6 Hz), 6.77 (d, 1H, J=7.6 Hz), 6.47 (d, 1H, J=7.6 Hz), 4.04-3.99 (m, 1H), 3.80-3.75 (m, 1H), 3.66-3.59 (m, 2H), 3.56-3.50 (m, 1H), 2.52-2.43 (m, 1H), 2.21-2.13 (m, 1H).

Dissolve (3S)-1-(6-bromopyridin-2-yl)-pyrrolidin-3-ylamine hydrochloride (131 mg, 0.47 mmol) in methanol. Add triethylamine (200 μL, 1.44 mmol) and 2,4-dichlorobenzaldehyde (116 mg, 0.66 mmol). Stir at room temperature overnight. Add sodium borohydride (100 mg, 2.63 mmol) and stir 2 hours. Pour onto a column of Dowex® 50wx4-200 and wash with methanol. Elute with 10:90 triethylamine:methanol, concentrate to give a residue. Chromatograph the residue on silica gel eluting with 100:0 to 40:60 ethyl acetate:hexanes to give the title compound. Combine the title compound and ethyl acetate and add 1 N hydrochloric acid in methanol (1.5 mL). Concentrate to dryness to give the hydrochloride salt of the title compound (174 mg, 85%). $^1$H NMR (400 MHz, MeOH-d4) δ 7.67 (d, 1H, J=2.0 Hz), 7.64 (d, 1H, J=8.0 Hz), 7.49 (dd, 1H, J=8.0, 2.0 Hz), 7.40 (t, H, J=8.0 Hz), 6.79 (d, 1H, J=8.0 Hz), 6.49 (d, 1H, J=8.0 Hz), 4.46 (s, 2H), 4.17-4.11 (m, 1H), 3.95-3.91 (m, 1H), 3.79-3.75 (m, 1H), 3.73-3.66 (m, 1H), 3.54-3.48 (m, 1H), 2.65-2.56 (m, 1H), 2.38-2.29 (m, 1H); MS (ES): m/z=400 [M+H].

Example 112

(3S)-[1-(5-Bromopyrimidin-2-yl)-pyrrolidin-3-yl]-(2-chloro-4-trifluoromethylbenzyl)-amine

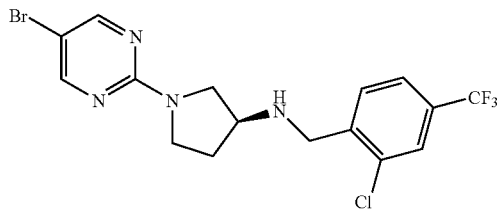

Dissolve 2-chloro-4-trifluoromethylbenzonitrile (405 mg, 1.97 mmol) in anhydrous toluene (7 mL) and cool in a dry ice/ethanol bath. Add diisobutylaluminum hydride (DIBAL) (3.94 mL, 3.94 mmol, 1.0 M in toluene) slowly. Stir 30 min. Warm to room temperature, add acetic acid (2 mL) and wafer (10 mL) and stir for 2 hours. Extract the aqueous layer with ethyl acetate twice. Wash the organic layer with potassium sodium tartrate solution (Rochelle salt) twice. Dry (magnesium sulfate), filter, and concentrate to give a residue. Chromatograph the residue on silica gel eluting with a gradient of 100:0 to 1:1 hexanes:dichloromethane to give 2-chloro-4-trifluoromethylbenzaldehyde (123 mg, 30%). $^1$H NMR (400 MHz, CDCl$_3$) δ 10.52 (s, 1H), 8.05 (d, 1H, J=8.0 Hz), 7.75 (s, 1H), 7.66 (d, 1H, J=8.0 Hz).

Using the method essentially as described in Example 111 using 2-chloro-4-trifluoromethylbenzaldehyde and 1-(5-bromopyrimidin-3-yl)-pyrrolidin-3-ylamine hydrochloride as starting materials to give the title compound. $^1$H NMR (hydrochloride salt) (400 MHz, MeOH-d4) δ 8.41 (s, 2H), 7.92 (s, 1H), 7.83 (d, 1H, J=8.0 Hz), 7.77 (d, 1H, J=8.0 Hz), 4.56-4.48 (m, 2H), 4.16-4.12 (m, 1H), 4.04-3.99 (m, 1H), 3.86-3.79 (m, 2H), 3.69-3.62 (m, 1H), 2.63-2.55 (m, 1H), 2.36-2.29 (m, 1H); MS (ES): m/z=435 [M+H].

Example 113

(3S)-[1-(5-Bromopyridin-3-yl)-pyrrolidin-3-yl]-(2,4-dichlorobenzyl)-amine

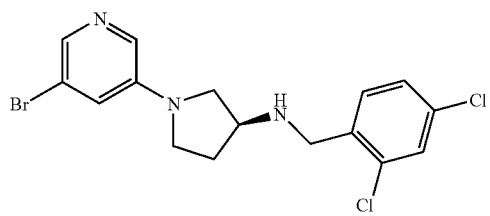

Using 3,5-dibromopyridine and the method essentially as described in Example 111 gives the title compound (74 mg). Combine the title compound and methanol and add fumaric acid (21 mg, 0.18 mmol) in methanol. Concentrate and add acetonitrile. Stir overnight and filter the solid to give the fumarate salt of the title compound (70 mg, 73%). $^1$H NMR (400 MHz, MeOH-d4) δ 7.89 (m, 2H), 7.55-7.53 (m, 2H), 7.38 (dd, 1H, J=8.4, 2.4 Hz), 7.19 (d, 1H, J=2.4 Hz), 6.71 (s, 2H), 4.12 (s, 2H), 3.77-3.75 (m, 1H), 3.64-3.59 (m, 1H), 3.57-3.51 (m, 1H), 3.40-3.33 (m, 2H), 2.42-2.36 (m, 1H), 2.13-2.06 (m, 1H); MS (ES): m/z=400 [M+H].

Example 114

(3S)-[1-(5-Bromopyrimidin-2-yl)-pyrrolidin-3-yl]-(2,6-dichloropyridin-3-ylmethyl)-amine

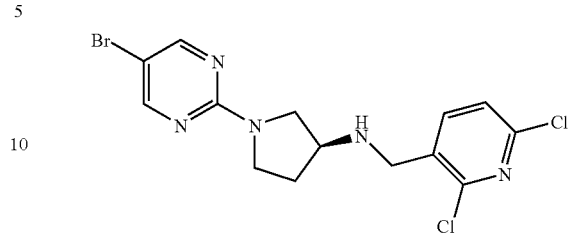

Dissolve 2,6-dichloronicotinic acid (1000 mg, 5.21 mmol) in anhydrous tetrahydrofuran (5 mL). Cool to 0° C. Add borane-tetrahydrofuran complex (7.82 mL, 7.82 mmol, 1.0 M in tetrahydrofuran) slowly. Stir the mixture at room temperature overnight. Add water (1 mL) and potassium carbonate, stir for 2 hours, filter and concentrate to give a residue. Chromatograph the residue on silica gel eluting with 10:90 to 20:80 ethyl acetate:hexanes to give (2,6-dichloropyridin-3-yl)-methanol (876 mg, 94%). $^1$H NMR (400 MHz, MeOH-d4) δ 7.96 (d, 1H, J=8.0 Hz), 7.45 (d, 1H, J=8.0 Hz), 4.64 (s, 2H).

Dissolve (2,6-dichloropyridin-3-yl)-methanol (876 mg, 4.92 mmol) in dichloromethane (20 mL). Add pyridium chlorochromate (2.12 g, 9.84 mmol). Stir for 2 hours. Add diethyl ether and stir for 20 minutes. Filter the mixture through a pad of Celite® and silica gel and concentrate to give 2,6-dichloropyridine-3-carbaldehyde (575 mg, 66%): $^1$H NMR (400 MHz, CDCl$_3$) δ 10.39 (s, 1H), 8.18 (d, 1H, J=8.0 Hz), 7.43 (d, 1H, J=8.0 Hz).

Using 1-(5-bromopyrimidin-3-yl)-pyrrolidin-3-ylamine hydrochloride and the method essentially as described in Example 111 gives the title compound as the hydrochloride salt (130 mg, 30%). $^1$H NMR (400 MHz, MeOH-d4) δ 8.42 (s, 2H), 8.05 (d, 1H, J=7.6 Hz), 7.58 (d, 1H, J=7.6 Hz), 4.49-4.41 (m, 2H), 4.16-4.12 (m, 1H), 4.03-3.98 (m, 1H), 3.86-3.79 (m, 1H), 3.73-3.66 (m, 2H), 3.69-3.63 (m, 1H), 2.63-2.54 (m, 1H), 2.36-2.27 (m, 1H); MS (ES): m/z=402 [M+H].

Example 115

(3S)-[1-(5-Bromopyrimidin-2-yl)-pyrrolidin-3-yl]-(4-chloro-2-trifluoromethylbenzyl)-amine

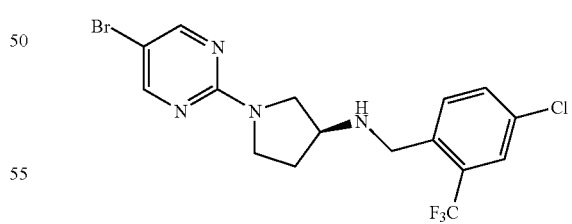

Add 4-chloro-1-iodo-2-trifluromethylbenzene (1500 mg, 4.89 mmol), zinc cyanide (345 mg, 2.94 mmol), and tetrakis (triphenylphosphine)palladium(0) (564 mg, 0.488 mmol) to anhydrous N,N-dimethylformamide (40 mL). Heat to 80° C. overnight. Cool to room temperature, dilute with toluene, wash with 2 N ammonium hydroxide (3×), saturated aqueous sodium chloride, dry, filter, concentrate to give a residue. Chromatograph the residue on silica gel eluting with hexanes/dichloromethane, to give 4-chloro-2-trifluoromethylbenzonitrile (630 mg, 63%): $^1$H NMR (400 MHz, CDCl$_3$) δ 7.81-7.78 (m, 2H), 7.67 (dd, 1H, J=8.4, 2.4 Hz).

Add 4-chloro-2-trifluoromethyl-benzonitrile to formic acid (96%) (15 mL) and water (3 mL). Add nickel-aluminum alloy (1260 mg). Heat at 100° C. overnight. Dilute with ethyl acetate and filter through Celite®. Extract the filtrate with 1 N sodium hydroxide and saturated aqueous sodium chloride, dry (sodium sulfate), filter, and concentrate to give 4-chloro-2-trifluoromethylbenzaldehyde (555 mg, 87%): $^1$H NMR (400 MHz, MeOH-d4) δ 10.29 (m, 1H), 8.10 (d, 1H, J=8.4 Hz), 7.91 (d, 1H, J=1.6 Hz), 7.85 (dd, 1H, J=8.4, 1.6 Hz).

Using 1-(5-bromopyrimidin-3-yl)-pyrrolidin-3-ylamine hydrochloride and the method essentially as described in Example 111 gives the title compound as the hydrochloride salt (430 mg, 34%). $^1$H NMR (400 MHz, MeOH-d4) δ 8.41 (s, 2H), 7.89 (s, 1H), 7.82 (m, 2H), 4.52-4.43 (m, 2H), 4.21-4.15 (m, 1H), 4.05-4.00 (m, 1H), 3.86-3.76 (m, 2H), 3.68-3.61 (m, 1H), 2.64-2.56 (m, 1H), 2.35-2.28 (m, 1H); MS (ES): m/z=435 [M+H].

Example 116

(3S)-(2,4-Dichlorobenzyl)-[1-(5-ethylpyridin-2-yl)-pyrrolidin-3-yl]-amine

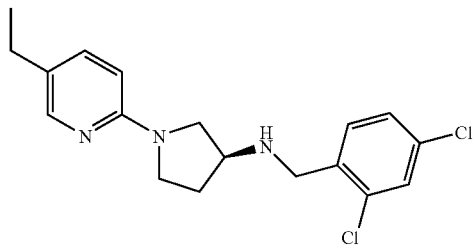

Add (2,4-dichlorobenzyl)-[1-(5-iodopyridin-2-yl)-pyrrolidin-3-yl]-amine dihydrochloride (272 mg, 0.61 mmol), triethylborane (1 mL, 1 mmol, 1.0 M in hexanes), tetrakis(triphenylphosphine)palladium(0) (25 mg, 0.031 mmol), and potassium carbonate (253 mg, 1.83 mmol) to anhydrous N,N-dimethylformamide (10 mL). Heat at 65° C. overnight. Dilute with water and extract twice with ethyl acetate. Wash the organic layer with saturated aqueous sodium chloride, dry (magnesium sulfate), filter, concentrate to give a residue. Chromatograph the residue on silica gel eluting with 10:90 to 1:1 ethyl acetate:hexanes, to give the title compound. Combine the title compound and ethyl acetate, add 1 N hydrochloric acid in methanol (1 mL), and concentrate to give the title compound as the hydrochloride salt (35 mg, 13%). $^1$H NMR (400 MHz, MeOH-d4) δ 7.98 (d, 1H, J=8.8 Hz), 7.80 (s, 1H), 7.69-7.67 (m, 2H), 7.49 (dd, 1H, J=8.0, 2.2 Hz), 7.09 (d, 1H, J=8.8 Hz), 4.50-4.42 (m, 2H), 4.25-4.22 (m, 1H), 4.10-4.05 (m, 1H), 3.90-3.84 (m, 2H), 3.74-3.68 (m, 1H), 2.71-2.61 (m, 1H), 2.64 (q, 2H, J=7.2 Hz), 2.47-2.41 (m, 1H), 1.24 (t, 3H, J=7.2 Hz); MS (ES): m/z=350 [M+H].

Example 117

(S)-(2,4-Dichlorobenzyl)-[1-(4-trifluoromethyl-pyrimidin-2-yl)-pyrrolidin-3-yl]-amine

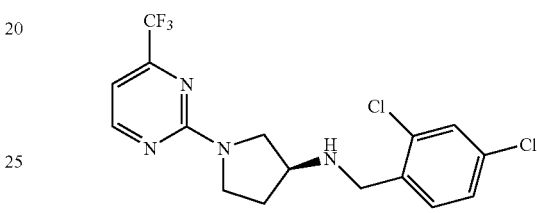

Stir a mixture of (S)-(2,4-dichlorobenzyl)-pyrrolidin-3-ylamine (266 mg, 1 mmol), 2-chloro-4-(trifluoromethyl)-pyrimidine (365 mg, 2 mmol) and polymer supported potassium carbonate (626 mg, 2 mmol) at 80° C. overnight. Filter away the polymer and pour the filtered reaction mixture onto a SCX-2 column. Elute with methanol and then elute with 2 M ammonia in methanol. Concentrate to give a residue and chromatograph on silica gel to give the title compound (258 mg, 66%). Prepare the hydrochloride salt essentially as described in EXAMPLE 1 to give the hydrochloride salt of the title compound. $^1$H NMR (400 MHz, MeOH-d$_4$) δ 8.39 (2H, m), 7.71 (1H, d, J=8.56 Hz), 7.68 (1H, d, J=1.71 Hz), 7.51 (1H, dd, J=8.31, 1.96 Hz), 4.46-4.55 (2H, m), 4.19-4.26 (1H, m), 4.09-4.14 (1H, m), 3.89-3.98 (2H, m), 3.73 (1H, m), 2.63-2.70 (1H, m), 2.39-2.48 (1H, m), MS (ES): m/z=391 [M+].

The following compounds are prepared essentially as described in Example 117.

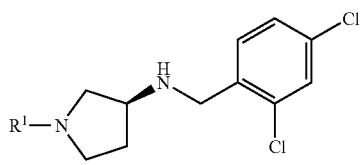

| EX | Compound | R$^1$ |
|---|---|---|
| 118 | (S)-[1-(4-Chloro-6-methylpyrimidin-2-yl)-pyrrolidin-3-yl]-(2,4-dichlorobenzyl)amine<br>$^1$H NMR (400 MHz, MeOH-d4) δ 7.72 (1H, d, J=8.3 Hz), 7.66 (1H, d, J=2.0 Hz), 7.48 (1H, dd, J=8.3, 2.2 Hz), 6.89 (1H, s), 4.45-4.53 (2H, m), 4.20-4.26 (1H, m), 4.13-4.18 (1H, m), 3.95-4.06 (2H, m), 3.78 (1H, ddd, J=11.6, 8.0, 6.6 Hz), 2.61-2.72 (1H, m), 2.41-2.52 (4H, m); MS (ES): m/z = 371 [M+]. | 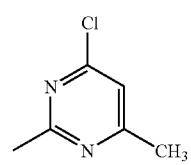 |

-continued

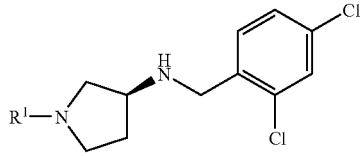

| EX | Compound | R¹ |
|---|---|---|
| 119 | [(S)-1-(4-Chloro-5-methylpyrimidin-2-yl)-pyrrolidin-3-yl]-(2,4-dichlorobenzyl)amine<br>¹H NMR (400 MHz, MeOH-d4) δ 7.89 (1H, s), 7.69-7.75 (2H, m), 7.54 (1H, dd, J=8.3, 2.2 Hz), 4.49-4.57 (2H, m), 4.11-4.22 (3H, m), 4.03-4.09 (1H, m), 3.98 (1H, ddd, J=10.8, 7.7, 7.5 Hz), 2.61 (1H, td, J=13.5, 6.2 Hz), 2.43 (3H, s), 2.32-2.42 (1H, m); MS (ES): m/z = 371 [M+]. | 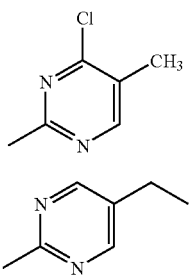 |
| 120 | (S)-(2,4-Dichlorobenzyl)-[1-(5-ethylpyrimidin-2-yl)-pyrrolidin-3-yl]amine<br>¹H NMR (400 MHz, MeOH-d4) δ 8.36 (2H, s), 7.64-7.74 (2H, m), 7.48 (1H, dd, J=8.3, 2.0 Hz), 4.43-4.53 (2H, m), 4.16-4.26 (1H, m), 4.04-4.13 (1H, m), 3.86-3.96 (2H, m), 3.70 (1H, ddd, J=10.8, 7.6, 7.3 Hz), 2.54-2.65 (3H, m), 2.36-2.46 (1H, m), 1.22 (3H, t, J=7.6 Hz); MS (ES): m/z = 351 [M+]. | 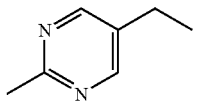 |

Example 121

1-(5-Bromopyrimidin-2-yl)-4-(2,4-dichlorobenzylamino)-pyrrolidin-3-one

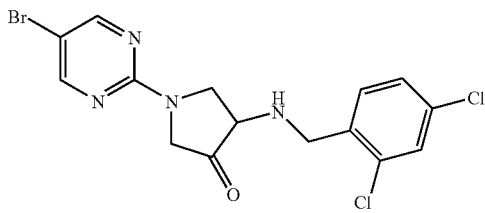

Stir a mixture of (3R,S)-(4R,S)-trans-1-(5-bromopyrimidin-2-yl)-4-(2,4-dichlorobenzylamino)-pyrrolidin-3-ol (700 mg, 1.67 mmol), di-tert-butyl dicarbonate (730 mg, 3.34 mmol), sodium chloride (672 mg, 6.41 mmol), saturated aqueous sodium hydrogen carbonate (3.5 mL) in chloroform (8 mL) at 85° C. overnight. Add water, extract with chloroform three times, combine the organics and wash with saturated aqueous sodium chloride, dry (magnesium sulfate), filter and concentrate. Chromatograph on silica gel to give [(3R,S)-(4R,S)-trans-1-(5-bromopyrimidin-2-yl)-4-hydroxypyrrolidin-3-yl]-(2,4-dichlorobenzyl)carbamic acid tert-butyl ester (740 mg, 85%).

To a solution of oxalyl chloride (810 μL, 1.62 mmol) in dry dichloromethane, cooled down to −70° C., add a solution of dry dimethylsulfoxide (115 μL, 1.62 mmol) in dry dichloromethane (2 mL). Stir for 10 minutes then add a solution of [(3R,S)-(4R,S)-trans-1-(5-bromopyrimidin-2-yl)-4-hydroxypyrrolidin-3-yl]-(2,4-dichlorobenzyl) carbamic acid tert-butyl ester (350 mg, 0.675 mmol) in dry dichloromethane (7 mL). Stir for 30 minutes at −70° C. then add triethylamine (564 μL, 4.05 mmol). Stir for 1 hour at −70° C. then add water and extract with dichloromethane. Combine the organics, wash with saturated aqueous sodium chloride, dry (magnesium sulfate), filter, and concentrate to give a residue. Chromatograph the residue on silica gel to give 1-(5-bromopyrimidin-2-yl)-4-oxopyrrolidin-3-yl]-(2,4-dichlorobenzyl) carbamic acid tert-butyl ester (300 mg, 86%).

Dissolve 1-(5-bromopyrimidin-2-yl)-4-oxopyrrolidin-3-yl]-(2,4-dichlorobenzyl) carbamic acid tert-butyl ester (100 mg, 0.19 mmol) in a minimum amount of dichloromethane and add 1 M hydrogen chloride in diethyl ether (1 mL, 1 mmol) and stir at room temperature overnight to give a solid. Filter and dry under vacuum to give the title compound as the hydrochloride salt (87 mg, 100%). ¹H NMR (300 MHz, DMSO-d₆) δ 8.60 (2H, s), 7.74-7.85 (2H, m), 7.57 (1H, dd, J=8.29, 2.07 Hz), 4.52-4.64 (2H, m), 4.40 (1H, d, J=13.56 Hz), 4.26 (1H, m), 3.80-3.66 (3H, m); MS (ES): m/z=417 [M+H].

Example 122

(S)-(2,4-Dichlorobenzyl)-[1-(5-ethynylpyrimidin-2-yl)-pyrrolidin-3-yl]-amine

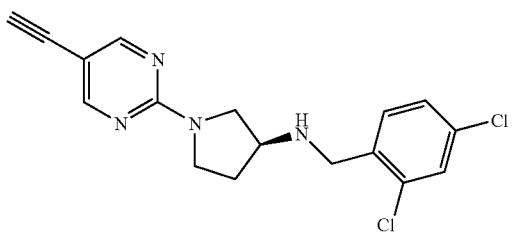

In a sealed vessel, heat a mixture of (S)-(2,4-dichlorobenzyl)-[1-(5-bromopyrimidin-2-yl)-pyrrolidin-3-yl]-amine (404 mg, 1.01 mmol), (trimethylsilyl)acetylene (250 μL, 1.76 mmol), dichlorobis(triphenylphosphine)palladium (II) (71.4 mg, 0.10 mmol), copper(I) iodide (20.7 mg, 0.11 mmol) and triethylamine (3 mL) at 100° C. for 4 hours. Cool to room temperature and dilute with water (30 mL). Filter through a pad of Celite®, washing with ethyl acetate. Extract the aqueous with additional ethyl acetate (3×50 mL) and wash the combined organics with saturated aqueous sodium chloride (50 mL). Concentrate and dissolve the residue in dichloromethane, filter, and concentrate to give a residue. Chromatograph the residue on silica gel to give (S)-(2,4-dichlorobenzyl)-[1-(5-trimethylsilanylethynylpyrimidin-2-yl)-pyrrolidin-3-yl]-amine as a yellow oil (337 mg, 80%).

Add tetrabutylammonium fluoride (1.0 mL, 1.0 mmol, 1.0 M solution in tetrahydrofuran) to a stirred solution of (S)-(2,4-dichlorobenzyl)-[1-(5-trimethylsilanylethynylpyrimidin-2-yl)-pyrrolidin-3-yl]-amine (327 mg, 0.78 mmol) in tetrahydrofuran (10 mL) at 0° C. Warm to room temperature and stir for 1 hour and concentrate to give a residue. Dilute the residue with water (10 mL), extract with ethyl acetate (3×25 mL). Extract the combined organic layers with saturated aqueous sodium chloride (10 mL), concentrate to give a residue. Dissolve the residue in dichloromethane, filter, concentrate to give a residue, and chromatograph the residue on silica gel followed by chromatography on SCX-2 to give the title compound as a yellow gum (194 mg, 72%).

Combine the title compound in diethyl ether (4 mL) and methanol (2 mL). Add succinic acid (66.6 mg, 0.56 mmol) and stir for 2 hours. Concentrate, add dichloromethane, and concentrate to give the title compound as the succinate salt (241 mg, 93%). $^1$H NMR (400 MHz, DMSO-$d_6$) 8.44 (2H, s), 7.50-7.58 (2H, m), 7.40 (1H, dd, J=8.31, 1.96 Hz), 4.25 (1H, s), 3.80 (2H, s), 3.57-3.67 (2H, m), 3.45-3.55 (1H, m), 3.33-3.43 (2H, m), 2.40 (4H, s), 2.03-2.13 (1H, m), 1.84-1.93 (1H, m); MS (ES): m/z=347 [M+].

Example 123

(S)-2-[3-(2,4-Dichlorobenzylamino)-pyrrolidin-1-yl]-pyrimidine-5-carbonitrile

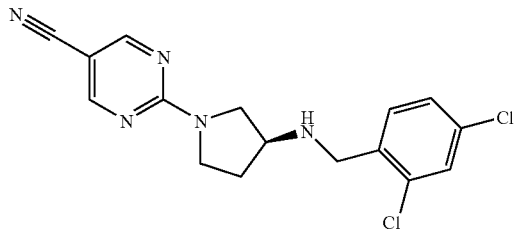

Add zinc cyanide (104 mg, 0.88 mmol) and tetrakis(triphenylphosphine) palladium(0) (209 mg, 0.18 mmol) to a stirred solution of (S)-(2,4-dichlorobenzyl)-[1-(5-bromopyrimidin-2-yl)-pyrrolidin-3-yl]-amine (359 mg, 0.89 mmol) in N,N-dimethylformamide (5 mL). Heat at 65° C. for 4 hours. Cool to room temperature and add 2 M aqueous ammonia solution (30 mL). Extract with ethyl acetate (3×50 mL), extract the combined organic layers with water (5×50 mL) followed by saturated aqueous sodium chloride (50 mL). Concentrate to give a residue. Dissolve the residue in dichloromethane, filter, and concentrate to give a residue. Chromatograph the residue on silica gel to give the title compound as a white solid (111 mg, 36%). $^1$H NMR (400 MHz, CDCl$_3$) δ 8.50 (2H, m), 7.32-7.40 (2H, m), 7.20-7.27 (1H, m), 3.86-3.94 (2H, m), 3.75-3.83 (2H, m), 3.63-3.71 (1H, m), 3.48-3.55 (2H, m), 2.20 (1H, m), 1.95 (1H, m); MS (ES): m/z=348 [M+].

Example 124

(S)-(2,4-Dichlorobenzyl)-[1-(5-fluoro-4-methoxypyrimidin-2-yl)-pyrrolidin-3-yl]amine

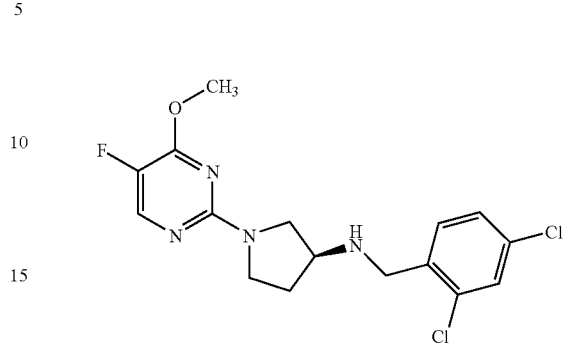

Dissolve (S)-[1-(4-chloro-5-fluoropyrimidin-2-yl)-pyrrolidin-3-yl]-(2,4-dichlorobenzyl)-amine (318 mg, 0.84 mmol) in dry 1,2-dimethoxyethane (20 mL) and add dropwise sodium methoxide in methanol (25% w/v, 1.9 mL, 8.46 mmol). Stir at 70° C. overnight. Add aqueous 2 N hydrochloric acid to a pH of about 6-7 and extract with 30:70 isopropanol:chloroform. Combine the organic layers, wash with saturated aqueous sodium chloride, dry (magnesium sulphate), filter, and concentrate to give a residue. Chromatograph the residue on silica gel to give the title compound (130 mg, 41%). Dissolve the title compound in methanol and add 1 M hydrogen chloride in diethyl ether (350 μL, 0.35 mmol), triturate, and concentrate to give the hydrochloride salt of the title compound. $^1$H NMR (400 MHz, MeOH-d4) δ 7.96 (1H, s), 7.65-7.76 (2H, m), 7.51 (1H, dd, J=8.2, 1.6 Hz), 4.45-4.56 (2H, m), 4.17 (2H, d, J=6.4 Hz), 3.99-4.10 (2H, m), 3.85-3.95 (4H, m), 2.61 (1H, d, J=6.4 Hz), 2.39 (1H, d, J=6.1 Hz); MS (ES): m/z=371 [M+].

Example 125

(S)-(2,4-Dichlorobenzyl)-[1-(5-fluoro-4-methylpyrimidin-2-yl)-pyrrolidin-3-yl]amine

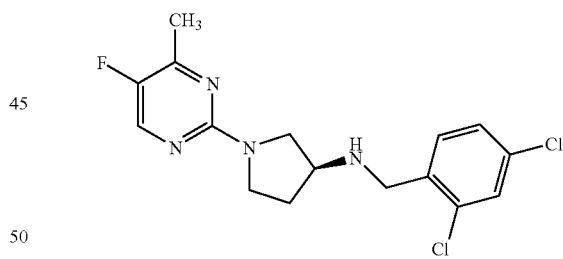

Dissolve (S)-[1-(4-chloro-5-fluoropyrimidin-2-yl)-pyrrolidin-3-yl]-(2,4-dichlorobenzyl)-amine (318 mg, 0.84 mmol) in dry tetrahydrofuran (7.5 mL) and add trimethylaluminium (510 μL, 1.01 mmol, 2 M in hexanes) and tetrakis(triphenylphosphine)palladium(0) (68 mg, 0.06 mmol). Stir at 70° C. overnight. Quench by addition of water and extract with chloroform. Combine the organic layers and wash with saturated aqueous sodium chloride, dry (magnesium sulfate), filter and chromatograph on silica gel. Dissolve the residue in methanol (2 mL) and deposit onto SCX cartridge, eluting with methanol, then 2 M ammonia in methanol. Concentrate the ammonia washing to give the title compound (180 mg, 60%). $^1$H NMR (400 MHz, MeOH-d4) δ 7.88 (1H, d, J=6.4 Hz), 7.43-7.54 (2H, m), 7.27-7.37 (1H, m), 3.84-3.96 (4H, m), 3.67-3.78 (1H, m), 3.55-3.64 (1H, m), 3.43-3.53 (1H, m), 2.41 (3H, s), 2.14-2.26 (1H, m), 1.89-2.00 (1H, m); MS (ES): m/z=355 [M+].

Example 126 and Example 127

1-(5-Bromopyrimidin-2-yl)-3-methylpyrrolidin-3-yl]-(2,4-dichlorobenzyl)-amine

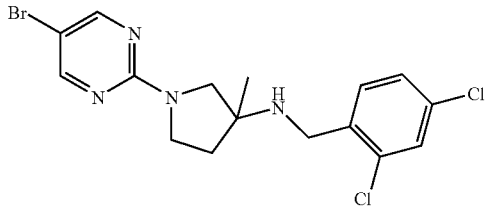

The title compound is prepared essentially as described in Example 28. The isomers are separated by chiral chromatography.

EXAMPLE 126-Isomer-1 as the hydrochloride: $^1$H NMR (400 MHz, MeOH-d4) δ 8.42 (2H, s), 7.62-7.68 (2H, m), 7.49 (1H, dd, J=8.3, 2.2 Hz), 4.42-4.49 (2H, m), 3.95 (1H, d, J=12.2 Hz), 3.87 (1H, ddd, J=11.7, 8.6, 5.1 Hz), 3.79 (1H, d, J=12.2 Hz), 3.70 (1H, dt, J=11.7, 7.7 Hz), 2.45-2.54 (1H, m), 2.37 (1H, ddd, J=13.3, 8.2, 5.1 Hz), 1.70 (3H, s); MS (ES): m/z=417 [M+H].

EXAMPLE 127-Isomer-2 as the hydrochloride: $^1$H NMR (400 MHz, MeOH-d4) δ 8.42 (2H, s), 7.62-7.68 (2H, m), 7.49 (1H, dd, J=8.3, 2.0 Hz), 4.42-4.49 (2H, m), 3.95 (1H, d, J=12.2 Hz), 3.87 (1H, ddd, J=11.8, 8.5, 5.1 Hz), 3.79 (1H, d, J=12.2 Hz), 3.70 (1H, dt, J=11.6, 7.7 Hz), 2.45-2.54 (1H, m), 2.37 (1H, ddd, J=13.3, 8.2, 5.1 Hz), 1.70 (3H, s), MS (ES): m/z=417 [M+H].

The following compounds are prepared essentially as described in Example 1.

| EX | Compound | R$^1$ | R$^2$ |
|---|---|---|---|
| 128 | (S)-(2,4-Dichlorobenzyl)-(1-pyrimidin-5-yl-pyrrolidin-3-yl)-amine<br>$^1$H NMR (400 MHz, CDCl$_3$) δ 8.57 (1H, s), 8.04 (2H, s), 7.32-7.41 (2H, m), 7.23 (1H, dd, J=8.3, 2.2 Hz), 3.87-3.95 (2H, m), 3.47-3.58 (3H, m), 3.35 (1H, td, J=8.5, 6.0 Hz), 3.13-3.20 (1H, m), 2.25 (1H, ddd, J=18.9, 7.6, 6.0 Hz), 1.93-2.02 (1H, m); MS (ES): m/z = 323 [M+]. | 5-pyrimidinyl | 2,4-dichlorophenyl |
| 129 | (S)-[1-(4-Bromothiazol-2-yl)-pyrrolidin-3-yl]-(2-chloro-4-fluorobenzyl)-amine<br>$^1$H NMR (300 MHz, CDCl$_3$) δ 7.38 (1H, dd, J=8.66, 5.84 Hz), 7.12 (1H, dd, J=8.57, 2.54 Hz), 6.95 (1H, td, J=8.37, 2.64 Hz), 6.35 (1H, s), 3.89 (2H, s), 3.38-3.69 (4H, m), 3.31-3.37 (1H, m), 2.19-2.30 (1H, m), 1.85-2.05 (1H, m); MS (ES): m/z = 390 [M+]. | 4-bromothiazol-2-yl | 2-chloro-4-fluorophenyl |

The following compounds are prepared essentially as described in Example 28.

| EX | Compound | R$^1$ |
|---|---|---|
| 130 | (S)-(2,4-Dichlorobenzyl)-[1-(5-nitrothiophen-2-yl)-pyrrolidin-3-yl]-amine<br>$^1$H NMR (400 MHz, DMSO-d$_6$) δ 7.95 (1H, d, J=4.89 Hz), 7.85 (1H, d, J=8.31 Hz), 7.77 (1H, s), 7.58 (1H, d, J=8.31 Hz), 6.13 (1H, d, J=4.89 Hz), 4.34 (2H, s), 4.09-4.19 (1H, m), 3.79-3.90 (2H, m), 3.66-3.77 (1H, m), 3.49-3.57 (1H, m), 2.51-2.54 (2H, m); MS (ES): m/z = 372 [M+]. | 5-nitrothiophen-2-yl |

-continued

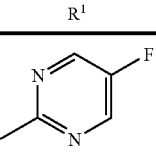

| EX | Compound | R¹ |
|---|---|---|
| 131 | (S)-(2,4-Dichlorobenzyl)-[1-(5-fluoropyrimidin-2-yl)-pyrrolidin-3-yl]-anime<br>¹H NMR (400 MHz, DMSO-d₆) δ 8.48 (2H, s), 7.90 (1H, d, J=8.56 Hz), 7.76 (1H, d, J=2.20 Hz), 7.57 (1H, dd, J= 8.44, 2.08 Hz), 4.26-4.37 (2H, m), 3.95-4.04 (1H, m), 3.86-3.94 (1H, m), 3.69-3.82 (2H, m), 3.51 (1H, m), 2.40 (2H, m); MS (ES): m/z = 341 [M+]. | 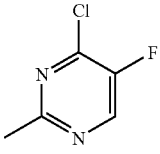 |
| 132 | (S)-[1-(4-Chloro-5-fluoropyrimidin-2-yl)-pyrrolidin-3-yl]-(2,4-dichlorobenzyl)-amine<br>¹H NMR (300 MHz, CDCl₃) δ 7.85 (1H, d, J=5.09 Hz), 7.39 (1H, d, J=2.07 Hz), 7.32-7.36 (1H, m), 7.21-7.25 (1H, m), 3.75-3.91 (5H, m), 3.58 (1H, dd, J=12.24, 2.64 Hz), 3.41-3.51 (1H, m), 2.06-2.19 (1H, m), 1.84-1.98 (1H, m); MS (ES): m/z = 375 [M+]. | 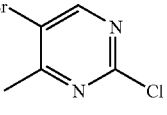 |
| 133 | (S)-[1-(5-Bromo-2-chloropyrimidin-4-yl)-pyrrolidin-3-yl]-(2,4-dichlorobenzyl)-amine<br>¹H NMR (400 MHz, CDCl₃) δ 8.12 (1H, s), 7.39 (1H, d, J=1.96 Hz), 7.35 (1H, d, J=8.31 Hz), 7.23 (1H, dd, J= 8.19, 2.08 Hz), 3.91-4.03 (3H, m), 3.86-3.91 (2H, m), 3.70 (1H, m), 3.42 (1H, m), 2.05-2.15 (1H, m), 1.88 (1H, m); MS (ES): m/z = 437 [M + H]. | 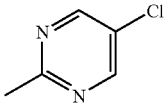 |
| 134 | (S)-[1-(5-Chloropyrimidin-2-yl)-pyrrolidin-3-yl]-(2,4-dichlorobenzyl)-amine<br>¹H NMR (hydrochloride) (400 MHz, DMSO-d6) δ 8.46 (2H, s), 7.89 (1H, d, J=8.31 Hz), 7.76 (1H, d, J=2.20 Hz), 7.57 (1H, dd, J=8.31, 2.20 Hz), 4.32 (2H, s), 4.01 (1H, dt, J=11.92, 5.90 Hz), 3.87-3.94 (1H, m), 3.78-3.84 (1H, m), 3.74 (1H, m), 3.52 (1H, m), 2.34-2.46 (2H, m); MS (ES): m/z = 358 [M + H]. | 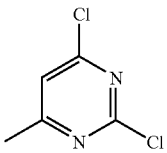 |
| 135 | (S)-(2,4-Dichlorobenzyl)-[1-(2,6-dichloropyrimidin-4-yl)-pyrrolidin-3-yl]amine<br>¹H NMR (400 MHz, DMSO-d₆) δ 7.89 (1H, d, J=8.31 Hz), 7.76 (1H, d, J=2.20 Hz), 7.57 (1H, dd, J=8.31, 2.20 Hz), δ 7.01 (1H, s), 4.35 (2H, s), 4.02 (1H, s), 3.88-3.94 (2H, m), 3.72-3.79 (1H, m), 3.51-3.59 (1H, m), 2.32-2.42 (2H, m); MS (ES): m/z = 393 [M + H]. | |

Example 136

6-[3-(2,4-Dichlorobenzylamino)-pyrrolidin-1-yl]-nicotinonitrile

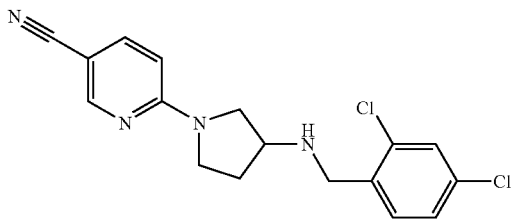

Stir a solution of 6-(3-aminopyrrolidin-1-yl)-nicotinonitrile (200 mg, 1.06 mmol) and 2,4-dichlorobenzaldehyde (371 mg, 2.12 mmol) in methanol (10 mL) for 1 hour. Add 10% sodium borohydride on alumina (400 mg) in one portion and stir for 2 hours. Dilute with dichloromethane (50 mL) and filter through a pad of Celite®. Concentrate to give a residue. Dissolve the residue in 5:95 methanol:dichloromethane and filter through a plug of silica gel. Concentrate to a residue and chromatograph by reverse phase chromatography, eluting with acetonitrile (0.1% trifluoroacetic acid):water (0.1% trifluoroacetic acid). Chromatograph on a SCX column eluting with methanol and then a 1:1 solution of 2.0 M ammonia in methanol:dichloromethane to give the title compound (55 mg, 15%). ¹H NMR (400 MHz, CDCl₃) δ 8.39 (d, 1H, J=1.8 Hz), 7.57-7.54 (m, 1H), 7.38-7.33 (m, 2H), 7.23-7.20 (m, 1H), 6.32 (d, 1H, J=8.8 Hz), 3.90 (s, 2H), 3.80-3.25 (m, 4H), 2.30-2.19 (m, 1H), 2.05-1.90 (m, 1H), 1.76 (br s, 1H); MS (ES): m/z=347.1, 349.0 [M+H]⁺.

Example 137

(3S)-[1-(5-Bromopyrimidin-2-yl)-pyrrolidin-3-yl]-(2,4,5-trichlorobenzyl)-amine

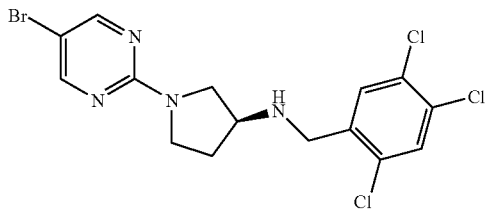

Add 1-iodo-2,4,6-trichlorobenzene (1500 mg, 4.88 mmol), zinc cyanide (345 mg, 2.94 mmol) and tetrakis(triphenylphosphine)palladium(0) (282 mg, 0.244 mmol) to anhydrous DMF (30 mL). Heat to 85° C. overnight. Cool to room temperature, dilute with toluene, wash with 2 N ammonium hydroxide (3×) and saturated aqueous sodium chloride and concentrate. Purify by silica gel chromatography, eluting with hexanes/dichloromethane to give 2,4,6-trichlorobenzonitrile (850 mg, 84%): $^1$H NMR (400 MHz, CDCl$_3$) δ 7.76 (s, 1H), 7.65 (s, 1H).

Add 2,4,6-trichlorobenzonitrile (206 mg, 1.0 mmol) to 96% formic acid (5 mL, 96%) and water (1 mL). Add nichol/aluminum alloy (206 mg) to the mixture. Heat at 100° C. for 4 hours. Dilute with ethyl acetate and filter through Celite®. Extract the filtrate with 1 N sodium hydroxide and saturated aqueous sodium chloride, dry (sodium sulfate), filter, and concentrate to give 2,4,6-trichlorobenzaldehyde (195 mg, 93%). $^1$H NMR (400 MHz, CDCl$_3$) δ 10.36 (s, 1H), 7.99 (s, 1H), 7.61 (s, 1H).

Using 1-(5-bromopyrimidin-3-yl)-pyrrolidin-3-ylamine hydrochloride and the method of Example 111 gives the title compound as the hydrochloride salt. $^1$H NMR (400 MHz, MeOH-d4) δ 8.41 (s, 2H), 7.84 (s, 1H), 7.83 (s, 1H), 4.43-4.41 (m, 2H), 4.13-4.11 (m, 1H), 4.01-3.97 (m, 1H), 3.86-3.77 (m, 2H), 3.68-3.62 (m, 1H), 2.60-2.55 (m, 1H), 2.32-2.26 (m, 1H); ES (MS): m/z=435 [M+H].

Example 138

(3S)-(3,5-Bis-trifluoromethylbenzyl)-[1-(6-fluoropyridin-3-yl)-pyrrolidin-3-yl]-amine

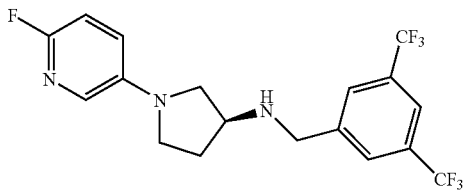

Using 3,5-bis-trifluoromethylbenzaldehyde and the method of Example 71 gives the title compound as the hydrochloride salt (60 mg, 67%). $^1$H NMR (400 MHz, MeOH-d4) δ 8.29 (s, 2H), 8.16 (s, 1H), 7.58 (m, 1H), 7.36 (m, 1H), 7.02 (dd, 1H, J=8.8, 2.8 Hz), 4.59 (s, 2H), 4.25-4.19 (m, 1H), 3.76-3.66 (m, 3H), 3.44-3.37 (m, 1H), 2.70-2.61 (m, 1H), 2.43-2.35 (m, 1H); ES (MS): m/z=408 [M+H].

Example 139

(S)-[1-(6-Fluoropyridin-3-yl)-pyrrolidin-3-yl]-naphthalen-1-ylmethylamine

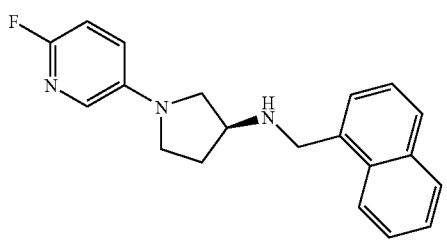

Using 1-naphthylaldehyde and the method of Example 51 gives the title compound as the hydrochloride salt $^1$NMR (400 MHz, DMSO-d6) δ 9.61 (br, 2H), 8.26 (d, J=8.4 Hz, 1H), 8.02 (d, J=8.17.6 Hz, 2H), 7.82 (d, J=6.4 Hz, 1H), 7.63 (m, 3H), 7.52 (m, 1H), 7.23 (ddd, J=8.8, 7.0, 3.2 Hz, 1H), 7.04 (dd, J=8.8, 3.2 Hz, 1H), 4.74 (br, 2H), 4.16 (m, 1H), 3.8-3.4 (m, 3H), 3.31 (m, 1H), 2.4 (m, 2H); MS (ES): m/z 322 [M+H].

The compounds of the present invention can be administered alone or in the form of a pharmaceutical composition, that is, combined with pharmaceutically acceptable excipient(s). In practice, the compounds of formula I are usually administered in the form of pharmaceutical compositions, that is, in admixture with pharmaceutically acceptable excipient(s) the proportion and nature of which are determined by the properties of the selected compound of formula I, the chosen route of administration, and standard pharmaceutical practice.

In another embodiment, the present invention provides pharmaceutical compositions comprising a compound of the formula I and a pharmaceutically acceptable excipient. Also, the present invention provides a pharmaceutical composition comprising the compound (S)-benzyl-[1-(5-trifluoromethylpyrid-2-yl)-pyrrolidin-3-yl]-amine and the pharmaceutically acceptable salts thereof (simply referred to in the description of compositions and methods as (S)-benzyl-[1-(5-trifluoromethylpyrid-2-yl)-pyrrolidin-3-yl]-amine) and a pharmaceutically acceptable excipient.

In effecting treatment of a patient afflicted with disorders described above, a compound of formula I or (S)-benzyl-[1-(5-trifluoromethylpyrid-2-yl)-pyrrolidin-3-yl]-amine can be administered in any form and route which makes the compound bioavailable. The compounds of formula I or (S)-benzyl-[1-(5-trifluoromethylpyrid-2-yl)-pyrrolidin-3-yl]-amine can be administered by a variety of routes, including oral and parenteral routes. For example, compounds of formula I or (S)-benzyl-[1-(5-trifluoromethylpyrid-2-yl)-pyrrolidin-3-yl]-amine can be administered orally, by inhalation, subcutaneously, intramuscularly, intravenously, transdermally, intranasally, rectally, occularly, topically, sublingually, and buccally. Oral administration is generally preferred. However, oral administration is not the only route or even the only preferred route. For example, transdermal administration may be very desirable for some patients and the intravenous route may be preferred as a matter of convenience or to provide suitable availability.

One skilled in the art can readily select the proper form and route of administration depending upon the particular characteristics of the compound selected, the disorder or condition to be treated, the stage of the disorder or condition, and other relevant circumstances. (*Remington's Pharmaceutical Sciences*, 18th Edition, Mack Publishing Co. (1990)). The pharmaceutical compositions of the present invention may be adapted for these various routes and may be administered to the patient, for example, in the form of tablets, capsules, cachets, papers, lozenges, wafers, elixirs, ointments, transdermal patches, aerosols, inhalants, suppositories, solutions, and suspensions.

The pharmaceutical compositions of the present invention are prepared in a manner well known in the pharmaceutical art using pharmaceutically acceptable excipients(s). Typically they will contain at least 1% of the compound of the present invention, the active ingredient, but may be varied depending upon the particular form and may conveniently be between 1% to about 70% of the weight of the dosage unit. The term "pharmaceutically acceptable excipient" refers to those typically used in preparing compositions and should be pharmaceutically pure and non-toxic in the amounts used, are suitable for use with each other and a compound of formula I or (S)-benzyl-[1-(5-trifluoromethylpyrid-2-yl)-pyrrolidin-3- yl]-amine. They generally are a solid, semi-solid, or liquid material which can serve as a vehicle or medium for the active ingredient. Some examples of pharmaceutically acceptable excipients are found in *Remington's Pharmaceutical Sciences,* 18th Edition, Mack Publishing Co. (1990) and *Handbook of Pharmaceutical Excipients,* Third Edition, Pharmaceutical Press (2000) and include diluents, vehicles, solvents, carriers, binders, disintegrants, lubricants, glidants, sweetening agents, flavoring agents, gel bases, sustained release matrices, stabilizing agents, preservatives, suspending agents, ointment bases, emulsifiers, dyes, propellants, coating agents, and others.

The present pharmaceutical compositions are preferably formulated in a unit dosage form, each dosage containing from about 0.1 mg to about 600 mg, more preferably about 5 mg to about 300 mg of the compound formula I or (S)-benzyl-[1-(5-trifluoromethylpyrid-2-yl)-pyrrolidin-3-yl]-amine.
The term "unit dosage form" refers to a physically discrete unit suitable as unitary dosages for the patient, each unit containing a predetermined quantity of active ingredient, in association with a suitable pharmaceutical excipient, by which one or more is calculated to produce the desired therapeutic effect.

The present invention provides methods of treatment of conditions associated with metabotropic glutamate receptors, comprising administering to a patient in need thereof an effective amount of a compound of formula I. Also provided are methods of treatment of conditions associated with metabotropic glutamate receptors, comprising administering to a patient in need thereof an effective amount of the compound (S)-benzyl-[1-(5-trifluoromethylpyrid-2-yl)-pyrrolidin-3-yl]-amine.

The term "conditions associated with metabotropic glutamate receptors" includes disorders, such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia and Alzheimer's disease), Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, seizures, migraine, urinary incontinence, substance tolerance, substance withdrawal (including, substances such as opiates, nicotine, tobacco products, alcohol, benzodiazepines, cocaine, sedatives, hypnotics, etc.), psychosis (including schizophrenia), anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute, chronic, persistent, intractable, neuropathic, and post-traumatic pain, especially inflammatory pain, arthritic pain, and burn pain), tardive dyskinesia, sleep disorders (including narcolepsy), attention deficit/hyperactivity disorder, and conduct disorder.

Many of the disorders which can be treated according to the present invention, such as cognitive disorders, are not uniformly described and classified in the art. Thus the term "cognitive disorders" is meant to encompass any disorder characterized by a deficit in one or more cognitive domain, including but not limited to short term memory, long term memory, working memory, executive function, and attention, and includes such disorders as age-related cognitive decline and mild cognitive impairment.

Where disorders which can be treated according to the present invention are described according to established and accepted classifications, these classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision, (ICD-10) provides classifications for many of the disorders described herein. In one of the available sources, *Dorland's Medical Dictionary* (23rd Ed., 1982, W. B. Saunders Company, Philadelphia, Pa.), migraine is defined as a symptom complex of periodic headaches, usually temporal and unilateral, often with irritability, nausea, vomiting, constipation or diarrhea, and photophobia. As used herein the term "migraine" includes to these periodic headaches, both temporal and unilateral, the associated irritability, nausea, vomiting, constipation or diarrhea, photophobia, and other associated symptoms and especially the associated pain.

The skilled artisan will recognize that there are alternative nomenclatures, nosologies, and classification systems for conditions described herein and that these systems evolve with medical and scientific progress. Where general terms are used herein to describe conditions associated with metabotropic glutamate receptors it is understood that the more specifically described conditions mentioned in the various diagnostic manuals and other materials included within the scope of this invention. For example, it is understood that the treatment of migraine contemplates the treatment of pain associated with migraine. Further for example, it is understood that mood disorders includes all the more specific depression disorders, dysthymic disorders, bipolar disorders, cyclothymic disorders, and other mood disorders as they are categorized in the art.

The present invention provides compounds of formula I for use as a medicament. Also, the present invention provides (S)-benzyl-[1-(5-trifluoromethylpyrid-2-yl)-pyrrolidin-3-yl]-amine for use as a medicament. The present invention also provides present compounds of formula I for use in the manufacture of a medicament to treat conditions associated with metabotropic glutamate receptors. Also provided is (S)-benzyl-[1-(5-trifluoromethylpyrid-2-yl)-pyrrolidin-3-yl]-amine for the manufacture of a medicament to treat conditions associated with metabotropic glutamate receptors.

As used herein the term "patient" refers to a mammal, such as a mouse, guinea pig, rat, dog, or human. It is understood that the preferred patient is a human.

As used herein terms "treat" "treatment" and "treating" are intended to include improvement of the conditions described herein. Also, it is also recognized that one skilled in the art may affect the disorders by treating a patient presently afflicted with the disorders or by prophylactically treating a patient believed to be susceptible to such disorders with an effective amount of the compound of formula I or (S)-benzyl-[1-(5-trifluoromethylpyrid-2-yl)-pyrrolidin-3-yl]-amine and the pharmaceutically acceptable salts thereof. Thus, the terms "treat" "treatment" and "treating" are intended to refer to all processes wherein there may be a slowing, interrupting, arresting, controlling, or stopping of the progression of the disorders described herein, but does not necessarily indicate a total elimination of all symptoms, and is intended to include prophylactic and therapeutic treatment of such disorders.

As used herein, the term "effective amount" refers to the amount of compound of formula I or (S)-benzyl-[1-(5-trifluoromethylpyrid-2-yl)-pyrrolidin-3-yl]-amine and the pharmaceutically acceptable salts thereof, which is effective, upon single or multiple dose administration to a patient, in treating the patient suffering from the named disorder. An effective amount can be readily determined by the attending diagnostician, as one skilled in the art, by the use of known techniques and by observing results obtained under analogous circumstances. In determining the effective amount, dose, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances. An effective amount of the present use invention, including a compound of formula I, is expected to vary from about 0.1 milligram per kilogram of body weight per day (mg/kg/day) to about 20 mg/kg/day. Preferred amounts can be determined by one skilled in the art.

In preferred embodiment the present invention provides a method for treating migraine, comprising: administering to a patient in need thereof an effective amount of a compound of formula I.

In another preferred embodiment the present invention provides a method for treating migraine, comprising: administering to a patient in need thereof an effective amount of a compound selected from the list consisting of (S)-benzyl-[1-(5-trifluoromethylpyrid-2-yl)-pyrrolidin-3-yl]-amine, 4-chlorobenzyl-[1-quinol-2-yl-pyrrolidin-3-yl]-amine, 4-bromobenzyl-[1-quinol-2-yl-pyrrolidin-3-yl]-amine, and 4-methylbenzyl-[1-quinol-2-yl-pyrrolidin-3-yl]-amine, and the pharmaceutically acceptable salts thereof. Also, included in the method of treating migraine are compounds when $R^2$ is 4-chlorophenyl, 4-bromophenyl, or 4-methylphenyl then $R^1$ is other than quinolin-2-yl; when $R^2$ is 4-halophenyl or 4-alkylphenyl then $R^1$ is other than quinolin-2-yl; when $R^2$ is phenyl optionally having one substituent, then $R^1$ is other than quinolin-2-yl optionally having one substituent; when $R^2$ is phenyl then $R^1$ is other than quinolyl; and when $R^2$ is phenyl then $R^1$ is other than quinolyl or isoquinolyl.

In a preferred embodiment the present invention provides a method for treating pain, comprising: administering to a patient in need thereof an effective amount of a compound of formula I.

In another preferred embodiment the present invention provides a method for treating pain, comprising: administering to a patient in need thereof an effective amount of a compound selected from the list consisting of (S)-benzyl-[1-(5-trifluoromethylpyrid-2-yl)-pyrrolidin-3-yl]-amine, 4-chlorobenzyl-[1-quinol-2-yl-pyrrolidin-3-yl]-amine, 4-bromobenzyl-[1-quinol-2-yl-pyrrolidin-3-yl]-amine, and 4-methylbenzyl-[1-quinol-2-yl-pyrrolidin-3-yl]-amine and the pharmaceutically acceptable salts thereof. Also, included in the method of treating pain are compounds wherein when $R^2$ is 4-halogenphenyl or 4-alkylphenyl then $R^1$ is quinolin-2-yl; when $R^2$ is phenyl having one substituent, then $R^1$ is quinolin-2-yl; and compounds wherein $R^1$ is quinolin-2-yl and quinolyl.

In a preferred embodiment the present invention provides a method for treating depression, comprising: administering to a patient in need thereof an effective amount of a compound of formula I.

In a preferred embodiment the present invention provides a method for treating schizophrenia, comprising: administering to a patient in need thereof an effective amount of a compound of formula I.

The activity of the compounds of the present invention can be determined by a variety of in vitro and in vivo methods including by the assay below.

Example A

Antagonism of Glutamate-Induced Increase in Intracellular Calcium with a mGluRs Expressing Cell Line Introduce human mGluR3 and the promiscuous G-protein, Galpha15 ($G_{\alpha15}$) into AV12 cells (an adenovirus-transformed Syrian hamster cell line) that stably express RGT (Rat Glutamate Transporter) and GLT (Glutamate Like Transporter). Maintain the expression of these four exogenous genes by culturing the cells in DMEM (Gibco, 11960-051) supplemented with 5% dialyzed fetal bovine serum, 2 mM glutamine, 1 mM sodium pyruvate, 10 mM HEPES, 100 µg/mL G418, 1 µg/mL puromycin, 1 µg/mL blastocidin, and 100 µg/mL zeocin. Passage confluent cultures weekly. The expression of $G_{\alpha15}$ allows the change of the signaling pathway of the mGlu$_3$ receptor to one that can be easily monitored through the release of intracellular calcium before and after the addition of drugs on a Fluorometric Imaging Plate Reader (i.e. FLIPR, Molecular Devices). Use the following buffers throughout as the Assay Buffer: HBSS (BioWhittaker, 10-527F) supplemented with 20 mM HEPES (Biowhittaker, 17-737E) at pH 7.4. Prepare a stock solution of 4 mM Fluo-3AM (Molecular Probes, F-1241), a calcium sensitive dye by adding 2.21 mL of 20% pluronate in DMSO to a vial containing 10 mg of Fluo-3AM. Sonicate the solution for 30 minutes to facilitate solubilization of the Fluo-3AM and then store at −20° C. Prepare the working solution of 8 µM Fluo-3AM by diluting the stock Fluo-3AM (4 mM) 500-fold into Assay Buffer. Harvest cells 24 h prior to assay using Hank's based cell dissociation solution (Specialty Media, a division of Cell & Molecular Technologies, S-004-B) and plate at a density of 50,000 cells per well in a 96-well poly-D-lysine treated black walled, clear bottom plate (Becton Dickinson, 356640). Incubate cells with 8 µM Fluo-3AM (50 µL per well) for 2 hours at 25° C. Following the dye-loading of the cells, remove the 8 µM Fluo-3AM and replace with Assay Buffer pre-warmed to 37° C. (50 µL per well). Ready the cells for assay on the FLIPR. Set the stage of the FLIPR to 34.5° C. prior to initiation of the assay. Perform a two addition FLIPR assay. Pre-warm the reagents for both additions (compounds and glutamate) to 37° C. prior to initiation of the assay. Add the test compound to the cell plate (50 µL per well) after taking an initial fluorescent read of the cell plate for 10 seconds. Test compounds in a 10 point concentration response curve starting at a final concentration on the cells of 12.5 µM with 3-fold dilutions in Assay Buffer/1.25% DMSO. Collect data every second for the first 30 seconds and then every 3 seconds until the second addition made at 2 minutes. Perform the second addition of 100 µM glutamate in Assay Buffer (100 µL per well for a final glutamate concentration of 50 µM on the cells) 2 minutes after the addition of compound. Collect the second addition data every second for 30 seconds and then every 3 seconds until the end of the run at total time of 3.25 minutes. Measure the response as maximal peak height in Relative Fluorescent Units (RFUs). Define the assay window as the maximal response obtained by 50 µM glutamate minus the response obtained by buffer alone. Express the results as a percent of the assay window.

Data from such an experiment with representative compounds of the present invention is presented in the table below.

| Example | IC$_{50}$ (nM) | ±SE (n) |
|---|---|---|
| 1 | 191 | 39(3) |
| 6 | 3907 | —(1) |
| 23 | 607 | 10(2) |
| 28 | 340 | 110(3) |
| 59 | 5776 | —(1) |
| 87 | 143 | 42(2) |
| 101 | 4927 | —(1) |
| 108 | 2268 | —(1) |
| 112 | 1649 | —(1) |
| 121 | 1679 | —(1) |
| 123 | 1182 | 240(2) |
| 134 | 77 | —(1) |

Example B

Rat Dural Plasma Protein Extravasation (PPE) Model

Prepare 100 μg/ml stock solution of test compound in a DMSO/saline (20%/80% v/v) solution and make subsequent dilutions with saline. Dose male Sprague-Dawley rats from Harlan Laboratories (250-350 g) with test compound or saline vehicle by oral gavage (2 mL/kg) or intravenous tail-vein injection (1 mL/kg) 45 minutes prior to administration of anesthesia and placement in a stereotaxic frame for implantation of stimulating electrodes. The rats dosed via the oral route are fasted overnight prior to dosing. Fifteen minutes prior to trigeminal ganglion stimulation, the rats are anesthetized with Nembutal (60 mg/kg, ip.) and placed in a stereotaxic frame (David Kopf Instruments) with the incisor bar set at −2.5 mm. Following a mid-line sagittal scalp incision, two pairs of bilateral holes are drilled through the skull (3.2 mm posteriorly, 1.8 and 3.8 mm laterally, all coordinates referenced to bregma). Pairs of stainless steel stimulating electrodes (Rhodes Medical Systems, Inc.), insulated except at the tips, are lowered through the holes in both hemispheres to a depth of 9.2 mm below the dura.

A solution of fluoroscein isothiocyanate (FITC) dye-labeled bovine serum albumin (BSA) (FITC-BSA, Sigma A9771 lot#122K7460) (20 mg/kg, iv.), is injected into the femoral vein 2 minutes prior to electrical stimulation of the trigeminal ganglion stimulation to function as the marker for protein extravasation. Sixty minutes following dosing with test compound or vehicle, the left trigeminal ganglion is stimulated for 5 minutes at a current intensity of 1.0 mA (5 Hz, 5 ms duration) with a Model S48 Grass Instrument Stimulator.

Five minutes following stimulation, the rats are exsanguinated with 40 ml of saline. The exsanguination also rinses residual FITC/BSA out of the blood vessels. Remove the top of the skull to collect the dural membranes. The membrane samples are removed from both hemispheres, rinsed with water, and spread flat on microscope slides. The slides are dried for 15 minutes on a slide warmer and cover-slipped with a 70% glycerol/water solution.

A fluorescence microscope (Zeiss) equipped with a grating monochromator and a spectrophotometer is used to quantify the amount of FITC-BSA dye in each dural sample. The microscope is equipped with a motorized stage interfaced with a personal computer. This facilitates the computer-controlled movement of the stage, with fluorescence measurements at 25 points (500 μm steps) on each dural sample. The extravasation induced by electrical stimulation of the trigeminal ganglion is an ipsilateral effect (i.e. occurs only on the side of the dura in which the trigeminal ganglion was stimulated). This allows the other (unstimulated) half of the dura to be used as a control. The extravasation ratio (i.e. the ratio of the amount of extravasation in the dura from the stimulated side compared to the unstimulated side) is calculated. Animals dosed with vehicle alone or an ineffective dose of the test compound have an extravasation ratio of approximately 2, while totally effective treatments result in a ratio of approximately 1. Express the results as ID$_{100}$, the dose that gives an extravasation ratio of approximately 1, indicating a complete inhibition of plasma protein extravasation.

Data from such an experiment with a representative compound of the present invention is presented in the table below.

| Example | ID$_{100}$ (μg/mL) p.o. | (n) | ID$_{100}$ (μg/mL) i.v. | (n) |
|---|---|---|---|---|
| 28 | 3 | 3 | 3 | 3 |

We claim:
1. A compound of the formula

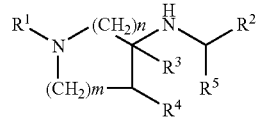

wherein
R$^1$ is selected from the group consisting of phenyl, optionally substituted with from 1 to 3 substituents independently selected from the group consisting of hydroxy, alkyl, substituted alkyl, alkenyl, alkynyl, alkoxy, cycloalkoxy, cycloalkyl, trifluoromethoxy, halogen, cyano, and nitro; and heteroaryl selected from the group consisting of thienyl, pyridyl, pyrimidyl, and thiazolyl, each heteroaryl optionally substituted with from 1 to 2 substituents independently selected from the group consisting of alkyl, alkenyl, alkynyl, alkanonyl, alkoxy, phenyl, trifluoromethyl, halogen, cyano, and nitro;
R$^2$ is selected from the group consisting of phenyl, optionally substituted with from 1 to 3 substituents independently selected from the group consisting of alkyl, substituted alkyl, alkoxy, cycloalkyl, methylenedioxy, halogen, cyano, and nitro; naphthyl, optionally substituted with from 1 to 2 substituents independently selected from the group consisting of hydroxy, alkyl, substituted alkyl, alkynyl, alkoxy, phenyl, halogen, cyano, and nitro; and heteroaryl selected from the group consisting of pyridyl, furyl, thienyl, isothiazolyl, and benzothienyl, each heteroaryl optionally substituted with from 1 to 2 substituents independently selected from the group consisting of alkyl, alkoxy, trifluoromethyl, halogen, cyano, and nitro;
R$^3$ is selected from the group consisting of hydrogen and methyl;
R$^4$ is selected from the group consisting of hydrogen, methyl, hydroxy, oxo, and fluoro;
R$^5$ is hydrogen;
n is 1; and
m is 1;
and the pharmaceutically acceptable salts thereof;
excluding the compound (S)-benzyl-[1-(5-trifluoromethylpyrid-2-yl)-pyrrolidin-3-yl]-amine.

2. A compound of claim 1 wherein $R^3$ is hydrogen and $R^4$ is hydrogen.

3. A compound of claim 2 wherein $R^2$ is phenyl.

4. A compound of claim 3 wherein $R^1$ is pyrimidyl.

5. A compound of claim 4 wherein the $R^1$ pyrimidyl is substituted with from 1 to 2 substituents independently selected from the group consisting of alkynyl, trifluoromethyl, halogen, cyano, and nitro, and the $R^2$ phenyl is optionally substituted with from 1 to 3 substituents independently selected from the group consisting of alkyl, substituted alkyl, alkoxy, cycloalkyl, halogen, cyano, and nitro.

6. A compound of claim 1 wherein $R^3$ is hydrogen, $R^4$ is hydrogen, $R^1$ is pyrimidyl substituted with from 1 to 2 substituents independently selected from the group consisting of alkynyl, trifluoromethyl, and halogen, and $R^2$ is phenyl optionally substituted with from 1 to 2 substituents independently selected from the group consisting of trifluoromethyl and halogen.

7. A compound of claim 5 wherein the $R^1$ pyrimidyl is attached in the 2-position.

8. A compound of claim 7 selected from the group consisting of [1-(5-bromopyrimidin-2-yl)-pyrrolidin-3-yl]-(2,4-dichlorobenzyl)-amine and [1-(5-chloropyrimidin-2-yl)-pyrrolidin-3-yl]-(2,4-dichlorobenzyl)-amine, and the pharmaceutically acceptable salts thereof.

9. A compound of claim 7 selected from the group consisting of (S)-[1-(5-bromopyrimidin-2-yl)-pyrrolidin-3-yl]-(2,4-dichlorobenzyl)-amine and the pharmaceutically acceptable salts thereof.

10. A compound of claim 7 wherein the compound is (S)-[1-(5-bromopyrimidin-2-yl)-pyrrolidin-3-yl]-(2,4-dichlorobenzyl)-amine hydrochloride.

11. A compound of claim 7 wherein the compound is (S)-[1-(5-bromopyrimidin-2-yl)-pyrrolidin-3-yl]-(2,4-dichlorobenzyl)-amine mesylate.

12. The compound (S)-[1-(5-bromopyrimidin-2-yl)-pyrrolidin-3-yl]-(2,4-dichlorobenzyl)-amine mesylate hemihydate.

13. A pharmaceutical composition comprising a compound of claim 1 and a pharmaceutically acceptable excipient.

14. A method of treating migraine comprising administering to a patient in need thereof an effective amount of a compound of claim 1.

15. A method of treating migraine comprising administering to a patient in need thereof an effective amount of a compound selected from the group consisting of (S)-[1-(5-bromopyrimidin-2-yl)-pyrrolidin-3-yl]-(2,4-dichlorobenzyl)-amine and the pharmaceutically acceptable salts thereof.

* * * * *